(12) United States Patent
Shirley

(10) Patent No.: US 8,367,894 B2
(45) Date of Patent: Feb. 5, 2013

(54) TRANSGENIC PLANTS WITH INCREASED STRESS TOLERANCE AND YIELD

(75) Inventor: Amber Shirley, Durham, NC (US)

(73) Assignee: BASF Plant Science GmbH (DE)

( * ) Notice: Subject to any disclaimer, the term of this patent is extended or adjusted under 35 U.S.C. 154(b) by 215 days.

(21) Appl. No.: 12/670,123

(22) PCT Filed: Aug. 1, 2008

(86) PCT No.: PCT/EP2008/060106
§ 371 (c)(1), (2), (4) Date: Jan. 22, 2010

(87) PCT Pub. No.: WO2009/016249
PCT Pub. Date: Feb. 5, 2009

(65) Prior Publication Data
US 2010/0223692 A1    Sep. 2, 2010

Related U.S. Application Data

(60) Provisional application No. 60/953,562, filed on Aug. 2, 2007.

(51) Int. Cl.
*A01H 5/00* (2006.01)
*C12N 15/82* (2006.01)

(52) U.S. Cl. .................................... 800/295; 800/278

(58) Field of Classification Search ................. None
See application file for complete search history.

(56) References Cited

U.S. PATENT DOCUMENTS

2002/0152497 A1    10/2002 Falco
2006/0135758 A1*   6/2006 Wu ........................ 536/24.3

FOREIGN PATENT DOCUMENTS

| EP | 1 033 405 A | 9/2000 |
|----|----|----|
| WO | WO 03/040344 | 5/2003 |
| WO | WO 03040344 A2 * | 5/2003 |
| WO | WO 2004/058963 | 7/2004 |
| WO | WO 2007/051866 | 5/2007 |

OTHER PUBLICATIONS

Database EMBL, "55ACACPE_UP_029_CO2_20DEC2004_012 Brassica napus AC Excell Brassica napus cDNA5', mRNA sequence." XP002503347.
Database UniProt, Jun. 1, 2001, SubName: Full=Transcriptional regulator, putative; XP002503348.
Nicolas Rouhier et al: Plant methionine sulfoxlde reductase A and B multigenic families Photosynthesis Research; Official Journal of the International Society of Photosynthesis Research, Springer, Berlin, DE, vol. 89, No. 2-3, Sep. 22, 2006, pp. 247-262 XP019453579.
Kwon Sun Jae et al: "Role of the methionine sulfoxide reductase MsrB3 in cold acclimation in Arabidopsis" Plant and Cell Physiology, vol. 48, No. 12, Dec. 2007, pp. 1713-1723.
Moskovitz Jackob et al: "Overexpression of peptide-methionine sulfoxide reductase in *Saccharomyces cerevisiae* and human T cells provides them with high resistance to oxidative stress" Porcedings of the National Academy of Sciences of the USA, vol. 95, No. 24, Nov. 24, 1998, pp. 14071-14075, XP002503434.
Romero Hernan M et al: "Investigations into the role of the plastidial peptide methionine sulfoxide reductase in response to oxidative stress in Arabidopsis" Plant Physiology, vol. 136, No. 3, Nov. 2004, pp. 3784-3794, XP002503435.

* cited by examiner

*Primary Examiner* — Vinod Kumar
(74) *Attorney, Agent, or Firm* — Patricia A. McDaniels

(57) ABSTRACT

Polynucleotides are disclosed which are capable of enhancing a growth, yield under water-limited conditions, and/or increased tolerance to an environmental stress of a plant transformed to contain such polynucleotides. Also provided are methods of using such polynucleotides and transgenic plants and agricultural products, including seeds, containing such polynucleotides as transgenes.

2 Claims, 4 Drawing Sheets

Figure 1 of 3

```
SEQ ID NO:2    (1)  ------------MASSSCFTIQSRFVSARTKLDSISKP----SLSGFACRSLTKPRNLNLSVLL----RCSMGSFNSSQ
SEQ ID NO:43   (1)  ------------MVAESVLVCRSSVVGAGLQSFVGEGAKRESAGPGRSVFLGAQVQKMGAGMSA----RSDVRPAAVPK
SEQ ID NO:8    (1)  ------------MGLSILRSTSISTPISSSKSKPIFSTLVRSSFASISPTKCVTPTTLFVSATP----FFTASPKRGFR
SEQ ID NO:6    (1)  MAMRQYAAATAAASSFRARPRARPSCLPAAALPLAPCCGVAWSRASYRASVRAMGAASSS----SSSSSSPSPQ
SEQ ID NO:4    (1)  ------------MGFNILRTTSISTPISSSKSKPIFSTLLRSSPSTIFPPKSVTPTTLFVSATP----FFTLHPKLGFR
SEQ ID NO:10   (1)  ------------MASPHAHPATRPLSSLPS----LLARSSSAATAAASSARPASLSLSCSRSRARAYCPAGRRLP

SEQ ID NO:2   (60)  KSDNVQEAAKS-D-FASISEGEWKKRLTPEQYYITRQKGTERAFTGEYWNTKTPGVYKCICCDTPLFDSSTKLDS
SEQ ID NO:43  (64)  ASGDVSEQTD----YKTFSDEEWKKRLSQQQFYVARKKGTERPFTGEYWNTKTAGTYLCVCCKTPLFSSKTKFDS
SEQ ID NO:8   (64)  GGIVAMAAGSLR----KSEEEWRAVLSPEQFRILRQKGTEFPGTGEYDKFFDEGVYNCAGCGTPLYRSLTKFNS
SEQ ID NO:6   (73)  GQAQAQAQGKPNY-STSLTDEEWRKRLITKDQYYITRQKGTEFPGTGEYDKFYEGVYHCVCCDTPLFESSTKFDS
SEQ ID NO:4   (64)  GGIVAMAAPGSLR----KSEEEWRAILSPEQFRILRQKGTEFPGTGEYDKFYEEGVYNCAGCGTPLYRSITKFNS
SEQ ID NO:10  (61)  GAVVAMSSAAPTPGVQKSEEEWEAVLTPEQFRILRRKGTEYPGTGEYDKFFSEGIYGCAGCGTPLYKSSTKFNS

SEQ ID NO:2  (133)  GTGWPSYYQPIGNNVKSKLDLSIIFMPRQEVICNAHLGHVFDDG--PRPTGKRYCLNSAALKIESLERTRE-
SEQ ID NO:43 (135)  GTGWPSYYDTIGDNVKSHMDWSIPFMPRTEVVCAVCDAHLGHVFDDG--PRPTGKRYCINSAAIDLKAEKQEERN
SEQ ID NO:8  (135)  GCGWPAFYEGIPGAINRNPDP---DGMRTEITCAACGGHLGHVFKGEGFPTPTNERHCVNSISLKFAPANS---
SEQ ID NO:6  (147)  GTGWPSYYQPIGDNVKCKLDMSIIFMPRTEVLCAVCDAHLGHVFDDG--PRPTGKRYCINSASLKLKKTQ----
SEQ ID NO:4  (135)  GCGWPAFYEGIPGAINRNPDP---DGMRTEITCAACGGHLGHVFKGEGFPTPTNERHCVNSISLKFAPANSYS--
SEQ ID NO:10 (136)  GCGWPAFYEGFPGAIKRTADP---DGRRIEITCAACEGHLGHVFKGEGFNTPTDERHCVNSISLKFVPASEEAS-
```

Figure 2 of 3

```
SEQ ID NO:12   (1)   ----------------------------------------------MMKRLSSSDSVGGLISLCPTTSTDQPNR---------RCGREFQSMLEGY
SEQ ID NO:44   (1)   MVVPSLPAFGGQNAMLRRNIDNNTDTLISLLQGSCSPRVSMQQVPRSSESLENMMG--ACGQKLPYFSSFDGPS
SEQ ID NO:14   (1)   -------MAGSGSAFSNITS---FLRTQQPSSQPLDSSLFLSAPSSAPFLGSRSMMSFDGEGGKGCNGSFFRA
SEQ ID NO:16   (1)   -------MEPGRLIFNTSGSNGQMLFMDCGAGGIAGAAGMFHRGVRPVLGGME---------E-GRGVKRPF

SEQ ID NO:12   (43)  EEEEEEAITEERGQTGLAEKKRRLNINQVKALEKNFELENKLEPERKVKLAQELGLQPRQVAVWFQNRRARWKTK
SEQ ID NO:44   (73)  VEEQEDVDEGIDEFAHHVEKKRRLSLEQVRSLERNFEVENKLEPERKMQLAKELGLRPRQVAVWFQNRRARWKTK
SEQ ID NO:14   (64)  FDMDDNGDECMDEYFHQPEKKRRLSASQVQFLEKSFEEENKLEPERKTKLAKDLGLQPRQVAIWFQNRRARWKNK
SEQ ID NO:16   (57)  FTSPDDMLEEEYYDEQLPEKKRRLTPEQVHLLERSFEEENKLEPERKTELARKLGLQPRQVAVWFQNRRARWKTK

SEQ ID NO:12   (118) QLEKDYGVLKTQYDSLRHNFDSLRRENESLLQEIGKLKAKLNGE-EEGDDVDEEENNLATMESDVSVKEEE---V
SEQ ID NO:44   (148) QLEHDYETLKKAYDRLKADFEAVTLDTNALKAEVSRLKGISNDDVKPAEFVQGKCDTTSHPASPAQSERSD---I
SEQ ID NO:14   (139) QLEKDYETLHASFESLKSNYDCLLKEKDKLKAEVASLTEKVLARGKQEGHMKQAESESEETKGLLHLQEQEPPQR
SEQ ID NO:16   (132) TLERDFDRLKASFDALRADHDALLQDNHRLRSQVVTLTEKMQDKEAPEGSFGAAADASEPEQAAAEAKASLADAE

SEQ ID NO:12   (189) SLPEQITEPPSSPPQLLEHSDSFNYRSFTDLRDLLPLKAAASSVAAAGSSDSSDSSAVLNEESSSNVTAAPATVP
SEQ ID NO:44   (220) VSSRNRTTPTIHVDPVAPEEAGAHLTMSSDSNSSEVMDADSPRTSHTSASRSTLSTSVVQPDEGLGVAQYPHFSP
SEQ ID NO:14   (214) LLLQSVSEGEGSKVSSVVGGCKQEDISSARSDILDSDSPHYTDGVHSALLEHGDSSYVFEPDQSDMSQDEEDNLS
SEQ ID NO:16   (207) EQAAAAEAFEVVQQQLHVKDEERLSPGSGGSAVLDARDALLGSGCGLAGVVDSSVDSYCFPGGAGGDEYHECVVG

SEQ ID NO:12   (264) --GGSFLQFVKMEQTEDHDDFLSGEEACGFFSDEQPPSLHWYSTVDQWN------
SEQ ID NO:44   (295) ---ENFVGPNMPEICADQSLASQVKLEEIHSFNPDQTFLLLPNWWDWA------
SEQ ID NO:14   (289) --KSLYPSYLFPKLEEDVDYSDPPESSCNFGFPEEDHVLWTWAYY---------
SEQ ID NO:16   (282) PVAGGIQSEEDDGAGSDEGCSYYPDDAAVFFAAAQGHGHHRTDDDDQQDDGQISYWMWN-
```

Figure 3 of 3

```
SEQ ID NO:18  (1)   ------------------------------------------------------------
SEQ ID NO:20  (1)   ------------------------------MDHDKTGCQSPPEGPKLCINNCGFFGSAATMNMCSKCHKAILFQQEQGARFA-
SEQ ID NO:34  (1)   --------------------------------MAEEHRCQTP-EGHRLCANNCGFLGSSATMNLCSNCYGDLCLKQQ-QASMK--
SEQ ID NO:38  (1)   --------------------------------MAEEHRCQAP-EGHRLCSNNCGFFGSPATMNLCSKCYRDIRLKEEEQAKTK--
SEQ ID NO:36  (1)   ---------------------------MAQKTEKEETDFKVP-ETITLCVNNCGVTGNPATNNMCQKCFTASTATTSGAGGAG--
SEQ ID NO:32  (1)   ---------------------------MAQREKKVEEPTELRAPEMTLCANSCGFPGNPATNNLCQNCFLAASASSS--SSS----
SEQ ID NO:44  (1)   ---------------------------MAQRDKKDQEPTELRAPEITLCANSCGFPGNPATQNLCQNCFLAATASTSPSSLS----
SEQ ID NO:22  (1)   ---------------------------MAQRDHKQEEPTELRAPEITLCANSCGFPGNPATQNLCQNCFLAGPASTS-PSSSS---
SEQ ID NO:28  (1)   ---------------------------MAQESCDLNKDEAEILKPSSSTPSPPSPATPPPPTA------
SEQ ID NO:45  (1)   MAPSPCVHGCTANCPRCHSYGHPIFGNSDLAAGGSDTSTSVFGKVGSVVIQSPAKNHAFGQACGPVFPSSSSPFR
SEQ ID NO:42  (1)   -------------------------------MATERVSQETTSQAP-EGPVMCKNLCGFFGSQATMGLCSKCYRETVMQAKMTALAE--
SEQ ID NO:30  (1)   -------------------------------MDHDKTGCQAPPEGPILCINNCGFFGSAATMNMCSKCHKDILLKQEQAKLAA----
SEQ ID NO:40  (1)   -------------------------------MDHDEAGCQAPSDHPILCVNNCGFFGSAATMNMCSKCHKDTMLNQEQSKLAA----
SEQ ID NO:26  (1)   -------------------------------MEPHDETGCQAP-ERPILCINNCGFFGSAATMNMCSKCYKDMLLKQEQDKFAA---
SEQ ID NO:24  (1)   -------------------------------MEHKEAGCQAP-EGPILCINNCGFFGSAATMNMCSKCHKEMITKQDQAKLAA----

SEQ ID NO:18  (53)  ------SAVSGGTS--------SSSNILKE---------TFAATALVDAETKS------VEPVAVSV
SEQ ID NO:20  (50)  ------STVESSLSAV------SPPSSEIGSMQSTVESSLSDVSPPSPETISISSPMIQPLV
SEQ ID NO:34  (51)  ------STIETALSGS------S--------SATVTATAVVASSVESPSAP------VESLP
SEQ ID NO:38  (56)  ------IASPATRSG-------------VSARPQKRSFP------EEPSPVAD
SEQ ID NO:36  (54)  ------AAASPSTTS-------LP------AVQSSAAA
SEQ ID NO:32  (57)  ------SPVLDKQPP-------VFPVVEKPRQ------LPPPVEEM
SEQ ID NO:44  (56)  ------SSSSSLPGV-------RP------AAPLVEPQAP------APLEAELA
SEQ ID NO:22  (37)  ------QIPEPQPP--------SA------PTPVIDRPRP------APLEAELA
SEQ ID NO:28  (76)  RIKFGPKDGEGKGPLKPIEKQPSKKRPFCFSPDETIDATVPPSTKPFGSFRSVCVTDADEARLKANREFFAPVSR
SEQ ID NO:45  (56)  ------QATQAAQATS------ATAAAVQPPAPVHETKLTCEVERTMIV------PHQSSSYQ
SEQ ID NO:42  (53)  ------SSIGNIMNGS------SSSTEKEP------VVAAAANIDIPVIP------VEPKTVSV
SEQ ID NO:30  (53)  ------SSAASILNGS------SMSLGREL------VIAAKTNS------VEPKTISV
SEQ ID NO:40  (53)  ------SSVENIVNGS------SNGNGKQ------AVATGAVAVQVEA------VEVKIVCA
SEQ ID NO:26  (52)  ------SSIDSIVNG-------SDAVME------PVVAGSNTVVAVAQ------VELQTMNV
SEQ ID NO:24  (52)  ------SPIDSIVNG-------GDGGKG------PVIAAS-VNVAVPQ------VEQKTI-V

SEQ ID NO:18  (91)  QPSSVQV-AAEVVAPEAAAAKLKEGPSRCATCNKRVGLTGFKCRCGDLFCGTHRYADIHNCSFNYHAAAQEAIAK
SEQ ID NO:20  (100) RNPSAELEVTATKTVTPPEQQQKRPNRCTTCRKRVGLTGFKCRCGTTFCGAHRYPEVHGCTFDFKSAGREEIAK
SEQ ID NO:34  (87)  QPP--------VLISPDIAAPVQANRCGACRKRVGLTGFKCRCRCGTTFCGSHRYPEKHACGEDFKAVGREEIAR
SEQ ID NO:38  (84)  PPS--------SDQTTPSEAKRVVNRCSGCRKRVGLTGFKCRCGELFCAEHRYSDRHDCSYDYKAAGREAIAR
SEQ ID NO:36  (83)  AVALIVERPTAGPVESSSKASRSSVNRCHSCRRRVGLTGFKCRCGELYCGAHRYSDRHDCSFDYKSAARDAIAR
SEQ ID NO:32  (86)  ASALATAPAPVAKTS--------AVNRCSRCRKRVGLTGFKCRCRCGHLFCGEHRYSDRHGCSYDYKSAARDAIAR
SEQ ID NO:44  (85)  RPAVDLAPATEAKPART-------SVNRCSSCRKRVGLTGFKCRCGDMFCGEHRYSDRHGCSYDYKAAAARDAIAR
SEQ ID NO:22  (68)  SKKKR-KHADAVSMAIVVEPLSSVLFVNRCNVCRKRVGLTGFKCRCRCEKLFCPRHRHSESHDCSFDYKTVGREEIAR
SEQ ID NO:28  (151) KRGFDPTDMTFGNAAAANAREEAKKWCGSCKKRVGLLGFKCRCTKFFCGKHRYPEEHGCTFDHVAFGRRIIEK
SEQ ID NO:40  (101) QDLVTPAAAAPQAVKSSIAAPSRPEPNRCGSCRKRVGLTGFKCRCGNLYCALHRYSDKHTCTYDYKAAGQEAIAK
SEQ ID NO:42  (93)  QPL-----FGSGPEGSVEAKP-KDGPKRCSSCNKRVGLTGFNCRCGDLFLCCTSLLDKHNCPFDYRTAAQDAIAK
```

Figure 3 continued

| SEQ ID NO | Position | Sequence |
|---|---|---|
| SEQ ID NO:30 | (87) | QPS------SASSAEESIEMKLPKEGPSRCNTCNKRVGLTGFKCRCENMFCANHRYSDKHNCPFDYRTAGREAISK |
| SEQ ID NO:40 | (91) | QSS------VDSSSGDSLEMKAKTGPSRCATCRKRVGLTGFSCKCGNLFCAMHRYSDKHDCPFDYRTVGQDAIAK |
| SEQ ID NO:26 | (89) | QQPADVAGPSEGVAAISKGGK--VGPNRCSACRKRVGLTGFNCRCGNLYCALHRYSDKHDCKFDYRTAARDAIAK |
| SEQ ID NO:24 | (87) | VQPMLVAETSEAAAVIPKAK---EGPDRCAACRKRVGLTGFSCRCGNMYCSVHRYSDKHDCQFDYRTAARDAIAK |
| SEQ ID NO:18 | (165) | ANPVVKAEKLDKI-- |
| SEQ ID NO:20 | (175) | ANPLVKAAKLQKI-- |
| SEQ ID NO:34 | (152) | ANPVIKGEKLRRI-- |
| SEQ ID NO:38 | (149) | ENPVIRAAKIVKV-- |
| SEQ ID NO:36 | (158) | ENPVVRAAKIVRF-- |
| SEQ ID NO:32 | (152) | DNPVVRAAKIVRF-- |
| SEQ ID NO:44 | (153) | DNPVVRAAKIVRF-- |
| SEQ ID NO:22 | (142) | ANPLIRAAKIIRI-- |
| SEQ ID NO:28 | (226) | QNPVLETDKLVDRI- |
| SEQ ID NO:45 | (176) | ANPLVVAEKVVKF-- |
| SEQ ID NO:42 | (162) | ANPVVKAEKLDKI-- |
| SEQ ID NO:30 | (157) | ANPLVKAEKLDKI-- |
| SEQ ID NO:40 | (160) | ANPIIKADKLDKI-- |
| SEQ ID NO:26 | (162) | ANPVVKADKLDKI-- |
| SEQ ID NO:24 | (159) | ANPVVRAEKLDKI-- |

US 8,367,894 B2

TRANSGENIC PLANTS WITH INCREASED STRESS TOLERANCE AND YIELD

This application is a national stage application under 35 U.S.C. §371 of PCT/EP2008/060106, filed Aug. 1, 2008, which claims benefit of U.S. provisional application Nos. 60/953,562, filed Aug. 2, 2007. The entire content of each of the above-identified applications are incorporated herein by reference.

FIELD OF THE INVENTION

This invention relates generally to transgenic plants which overexpress nucleic acid sequences encoding polypeptides capable of conferring increased stress tolerance and consequently, increased plant growth and crop yield, under normal or abiotic stress conditions. Additionally, the invention relates to novel isolated nucleic acid sequences encoding polypeptides that confer upon a plant increased tolerance under abiotic stress conditions, and/or increased plant growth and/or increased yield under normal or abiotic stress conditions.

BACKGROUND OF THE INVENTION

Abiotic environmental stresses, such as drought, salinity, heat, and cold, are major limiting factors of plant growth and crop yield. Crop yield is defined herein as the number of bushels of relevant agricultural product (such as grain, forage, or seed) harvested per acre. Crop losses and crop yield losses of major crops such as soybean, rice, maize (corn), cotton, and wheat caused by these stresses represent a significant economic and political factor and contribute to food shortages in many underdeveloped countries.

Water availability is an important aspect of the abiotic stresses and their effects on plant growth. Continuous exposure to drought conditions causes major alterations in the plant metabolism which ultimately lead to cell death and consequently to yield losses. Because high salt content in some soils results in less water being available for cell intake, high salt concentration has an effect on plants similar to the effect of drought on plants. Additionally, under freezing temperatures, plant cells lose water as a result of ice formation within the plant. Accordingly, crop damage from drought, heat, salinity, and cold stress, is predominantly due to dehydration.

Because plants are typically exposed to conditions of reduced water availability during their life cycle, most plants have evolved protective mechanisms against desiccation caused by abiotic stresses. However, if the severity and duration of desiccation conditions are too great, the effects on development, growth, plant size, and yield of most crop plants are profound. Developing plants efficient in water use is therefore a strategy that has the potential to significantly improve human life on a worldwide scale.

Traditional plant breeding strategies are relatively slow and require abiotic stress-tolerant founder lines for crossing with other germplasm to develop new abiotic stress-resistant lines. Limited germplasm resources for such founder lines and incompatibility in crosses between distantly related plant species represent significant problems encountered in conventional breeding. Breeding for tolerance has been largely unsuccessful.

Many agricultural biotechnology companies have attempted to identify genes that could confer tolerance to abiotic stress responses, in an effort to develop transgenic abiotic stress-tolerant crop plants. Although some genes that are involved in stress responses or water use efficiency in plants have been characterized, the characterization and cloning of plant genes that confer stress tolerance and/or water use efficiency remains largely incomplete and fragmented. To date, success at developing transgenic abiotic stress-tolerant crop plants has been limited, and no such plants have been commercialized.

In order to develop transgenic abiotic stress-tolerant crop plants, it is necessary to assay a number of parameters in model plant systems, greenhouse studies of crop plants, and in field trials. For example, water use efficiency (WUE), is a parameter often correlated with drought tolerance. Studies of a plant's response to desiccation, osmotic shock, and temperature extremes are also employed to determine the plant's tolerance or resistance to abiotic stresses. When testing for the impact of the presence of a transgene on a plant's stress tolerance, the ability to standardize soil properties, temperature, water and nutrient availability and light intensity is an intrinsic advantage of greenhouse or plant growth chamber environments compared to the field.

WUE has been defined and measured in multiple ways. One approach is to calculate the ratio of whole plant dry weight, to the weight of water consumed by the plant throughout its life. Another variation is to use a shorter time interval when biomass accumulation and water use are measured. Yet another approach is to use measurements from restricted parts of the plant, for example, measuring only aerial growth and water use. WUE also has been defined as the ratio of $CO_2$ uptake to water vapor loss from a leaf or portion of a leaf, often measured over a very short time period (e.g. seconds/minutes). The ratio of $^{13}C/^{12}C$ fixed in plant tissue, and measured with an isotope ratio mass-spectrometer, also has been used to estimate WUE in plants using $C_3$ photosynthesis.

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increase in water use (i.e. no change in WUE), could also increase yield. Therefore, new methods to increase both WUE and biomass accumulation are required to improve agricultural productivity.

Concomitant with measurements of parameters that correlate with abiotic stress tolerance are measurements of parameters that indicate the potential impact of a transgene on crop yield. For forage crops like alfalfa, silage corn, and hay, the plant biomass correlates with the total yield. For grain crops, however, other parameters have been used to estimate yield, such as plant size, as measured by total plant dry weight, above-ground dry weight, above-ground fresh weight, leaf area, stem volume, plant height, rosette diameter, leaf length, root length, root mass, tiller number, and leaf number. Plant size at an early developmental stage will typically correlate with plant size later in development. A larger plant with a greater leaf area can typically absorb more light and carbon dioxide than a smaller plant and therefore will likely gain a greater weight during the same period. This is in addition to the potential continuation of the micro-environmental or genetic advantage that the plant had to achieve the larger size initially. There is a strong genetic component to plant size and growth rate, and so for a range of diverse genotypes plant size under one environmental condition is likely to correlate with size under another. In this way a standard environment is used to approximate the diverse and dynamic environments encountered at different locations and times by crops in the field.

Harvest index, the ratio of seed yield to above-ground dry weight, is relatively stable under many environmental conditions and so a robust correlation between plant size and grain yield is possible. Plant size and grain yield are intrinsically linked, because the majority of grain biomass is dependent on current or stored photosynthetic productivity by the leaves and stem of the plant. Therefore, selecting for plant size, even at early stages of development, has been used as to screen for plants that may demonstrate increased yield when exposed to field testing. As with abiotic stress tolerance, measurements of plant size in early development, under standardized conditions in a growth chamber or greenhouse, are standard practices to measure potential yield advantages conferred by the presence of a transgene.

There is a need, therefore, to identify additional genes expressed in stress tolerant plants and/or plants that are efficient in water use that have the capacity to confer stress tolerance and/or increased water use efficiency to the host plant and to other plant species. Newly generated stress tolerant plants and/or plants with increased water use efficiency will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

The present inventors have discovered that transforming a plant with certain polynucleotides results in enhancement of the plant's growth and response to environmental stress, and accordingly the yield of the agricultural products of the plant is increased, when the polynucleotides are present in the plant as transgenes. The polynucleotides capable of mediating such enhancements have been isolated from *Brassica napus, Oryza sativa, Glycine max, Triticum aestivum, Hordeum vulgare, Zea mays,* and *Linum usitatissimum* and are listed in Table 1, and the sequences thereof are set forth in the Sequence Listing as indicated in Table 1.

TABLE 1

| Gene ID | Organism | Polynucleotide SEQ ID NO | Amino acid SEQ ID NO |
| --- | --- | --- | --- |
| BN51364980 | B. napus | 1 | 2 |
| OS34096188 | O. sativa | 3 | 4 |
| OS32583643 | O. sativa | 5 | 6 |
| GM53626178 | G. max | 7 | 8 |
| TA56540264 | T. aestivum | 9 | 10 |
| BN45206322 | B. napus | 11 | 12 |
| GM48923793 | G. max | 13 | 14 |
| TA55969932 | T. aestivum | 15 | 16 |
| BN47310186 | B. napus | 17 | 18 |
| BN51359456 | B. napus | 19 | 20 |
| HV62552639 | H. vulgare | 21 | 22 |
| ZM61995511 | Z. mays | 23 | 24 |
| LU61567101 | L. usitatissimum | 25 | 26 |
| LU61893412 | L. usitatissimum | 27 | 28 |
| OS39781852 | O. sativa | 29 | 30 |
| OS34701560 | O. sativa | 31 | 32 |
| OS36821256 | O. sativa | 33 | 34 |
| GM51659494 | G. max | 35 | 36 |
| GM49780101 | G. max | 37 | 38 |

TABLE 1-continued

| Gene ID | Organism | Polynucleotide SEQ ID NO | Amino acid SEQ ID NO |
| --- | --- | --- | --- |
| GM59637305 | G. max | 39 | 40 |
| TA55974113 | T. aestivum | 41 | 42 |

In one embodiment, the invention provides a transgenic plant transformed with an expression cassette comprising an isolated polynucleotide encoding a methionine sulfoxide reductase family protein selected from the group consisting of SEQ ID NO:2, SEQ ID NO:4, SEQ ID NO:6, SEQ ID NO:8, and SEQ ID NO:10, or a SeIR protein domain.

In another embodiment, the invention provides a transgenic plant transformed with an expression cassette comprising an isolated polynucleotide encoding a homeodomain leucine zipper protein having a sequence as set forth in SEQ ID NO:12, SEQ ID NO:14, or SEQ ID NO: 16.

In another embodiment, the invention provides a transgenic plant transformed with an expression cassette comprising an isolated polynucleotide encoding a zinc finger protein containing an A20 domain in combination with an AN1 domain selected from the group consisting of SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, and SEQ ID NO:44, or both AN1-like and A20-like zinc finger protein domains.

In a further embodiment, the invention concerns a seed produced by the transgenic plant of the invention, wherein the seed is true breeding for a transgene comprising the polynucleotide described above. Plants derived from the seed of the invention demonstrate increased tolerance to an environmental stress, and/or increased plant growth, and/or increased yield, under normal or stress conditions as compared to a wild type variety of the plant.

In a still another aspect, the invention concerns products produced by or from the transgenic plants of the invention, their plant parts, or their seeds, such as a foodstuff, feedstuff, food supplement, feed supplement, cosmetic or pharmaceutical.

The invention further provides the isolated polynucleotides identified in Table 1 below, and polypeptides identified in Table 1. The invention is also embodied in recombinant vector comprising an isolated polynucleotide of the invention.

In yet another embodiment, the invention concerns a method of producing the aforesaid transgenic plant, wherein the method comprises transforming a plant cell with an expression vector comprising an isolated polynucleotide of the invention, and generating from the plant cell a transgenic plant that expresses the polypeptide encoded by the polynucleotide. Expression of the polypeptide in the plant results in increased tolerance to an environmental stress, and/or growth, and/or yield under normal and/or stress conditions as compared to a wild type variety of the plant.

In still another embodiment, the invention provides a method of increasing a plant's tolerance to an environmental stress, and/or growth, and/or yield. The method comprises the steps of transforming a plant cell with an expression cassette comprising an isolated polynucleotide of the invention, and generating a transgenic plant from the plant cell, wherein the transgenic plant comprises the polynucleotide.

BRIEF DESCRIPTION OF THE DRAWINGS

FIG. 1 is an alignment of BN51364980, OS34096188, OS32583643, GM53626178, TA56540264 with a known methionine sulfoxide reductase family protein.

FIG. 2 is an alignment of BN45206322, GM48923793, and TA55969932 with a known homeodomain leucine zipper protein.

FIG. 3 is an alignment of BN47310186, BN51359456, HV62552639, ZM61995511, LU61567101, LU61893412, OS39781852, OS34701560, OS36821256, GM51659494, GM49780101, GM59637305, and TA55974113 with a known A20 and AN1 domain containing zinc finger protein.

DETAILED DESCRIPTION OF THE PREFERRED EMBODIMENTS

Throughout this application, various publications are referenced. The disclosures of all of these publications and those references cited within those publications in their entireties are hereby incorporated by reference into this application in order to more fully describe the state of the art to which this invention pertains. The terminology used herein is for the purpose of describing specific embodiments only and is not intended to be limiting. As used herein, "a" or "an" can mean one or more, depending upon the context in which it is used. Thus, for example, reference to "a cell" can mean that at least one cell can be used.

In one embodiment, the invention provides a transgenic plant that overexpresses an isolated polynucleotide identified in Table 1, or a homolog thereof. The transgenic plant of the invention demonstrates an increased tolerance to an environmental stress as compared to a wild type variety of the plant. The overexpression of such isolated nucleic acids in the plant may optionally result in an increase in plant growth or in yield of associated agricultural products, under normal or stress conditions, as compared to a wild type variety of the plant. Without wishing to be bound by any theory, the increased tolerance to an environmental stress, increased growth, and/or increased yield of a transgenic plant of the invention is believed to result from an increase in water use efficiency of the plant.

As defined herein, a "transgenic plant" is a plant that has been altered using recombinant DNA technology to contain an isolated nucleic acid which would otherwise not be present in the plant. As used herein, the term "plant" includes a whole plant, plant cells, and plant parts. Plant parts include, but are not limited to, stems, roots, ovules, stamens, leaves, embryos, meristematic regions, callus tissue, gametophytes, sporophytes, pollen, microspores, and the like. The transgenic plant of the invention may be male sterile or male fertile, and may further include transgenes other than those that comprise the isolated polynucleotides described herein.

As used herein, the term "variety" refers to a group of plants within a species that share constant characteristics that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more isolated polynucleotides introduced into a plant variety. As also used herein, the term "wild type variety" refers to a group of plants that are analyzed for comparative purposes as a control plant, wherein the wild type variety plant is identical to the transgenic plant (plant transformed with an isolated polynucleotide in accordance with the invention) with the exception that the wild type variety plant has not been transformed with an isolated polynucleotide of the invention.

As defined herein, the term "nucleic acid" and "polynucleotide" are interchangeable and refer to RNA or DNA that is linear or branched, single or double stranded, or a hybrid thereof. The term also encompasses RNA/DNA hybrids. An "isolated" nucleic acid molecule is one that is substantially separated from other nucleic acid molecules which are present in the natural source of the nucleic acid (i.e., sequences encoding other polypeptides). For example, a cloned nucleic acid is considered isolated. A nucleic acid is also considered isolated if it has been altered by human intervention, or placed in a locus or location that is not its natural site, or if it is introduced into a cell by transformation. Moreover, an isolated nucleic acid molecule, such as a cDNA molecule, can be free from some of the other cellular material with which it is naturally associated, or culture medium when produced by recombinant techniques, or chemical precursors or other chemicals when chemically synthesized. While it may optionally encompass untranslated sequence located at both the 3' and 5' ends of the coding region of a gene, it may be preferable to remove the sequences which naturally flank the coding region in its naturally occurring replicon.

As used herein, the term "environmental stress" refers to a sub-optimal condition associated with salinity, drought, nitrogen, temperature, metal, chemical, pathogenic, or oxidative stresses, or any combination thereof. The terms "water use efficiency" and "WUE" refer to the amount of organic matter produced by a plant divided by the amount of water used by the plant in producing it, i.e., the dry weight of a plant in relation to the plant's water use. As used herein, the term "dry weight" refers to everything in the plant other than water, and includes, for example, carbohydrates, proteins, oils, and mineral nutrients.

Any plant species may be transformed to create a transgenic plant in accordance with the invention. The transgenic plant of the invention may be a dicotyledonous plant or a monocotyledonous plant. For example and without limitation, transgenic plants of the invention may be derived from any of the following diclotyledonous plant families: Leguminosae, including plants such as pea, alfalfa and soybean; Umbelliferae, including plants such as carrot and celery; Solanaceae, including the plants such as tomato, potato, aubergine, tobacco, and pepper; Cruciferae, particularly the genus *Brassica*, which includes plant such as oilseed rape, beet, cabbage, cauliflower and broccoli); and *Arabidopsis thaliana*; Compositae, which includes plants such as lettuce; Malvaceae, which includes cotton; Fabaceae, which includes plants such as peanut, and the like. Transgenic plants of the invention may be derived from monocotyledonous plants, such as, for example, wheat, barley, sorghum, millet, rye, triticale, maize, rice, oats and sugarcane. Transgenic plants of the invention are also embodied as trees such as apple, pear, quince, plum, cherry, peach, nectarine, apricot, papaya, mango, and other woody species including coniferous and deciduous trees such as poplar, pine, sequoia, cedar, oak, and the like. Especially preferred are *Arabidopsis thaliana, Nicotiana tabacum*, oilseed rape, soybean, corn (maize), wheat, linseed, potato and tagetes.

As shown in Table 1, one embodiment of the invention is a transgenic plant transformed with an expression cassette comprising an isolated polynucleotide encoding a methionine sulfoxide reductase family protein. Methionine sulfoxide reductases (MSRs) catalyze the thioredoxin-dependent reduction of methionine sulfoxide (MetSO) to the correct methionine residue. Methionine is highly susceptible to oxidative damage, and methionine oxidation results in modification of the activity and conformation of many proteins.

There are two types of MSRs, type A and type B; however, these two types are unrelated in both sequence and structure. The MSRB enzyme selectively catalytically reduces the MetSO R enantiomer. MSRB type proteins contain four conserved cysteine residues in two CxxC motifs, where x can be any amino acid. These CxxC motifs are potentially involved in zinc fixation.

There are described examples from several plant species where environmental stress conditions result in increased reactive oxygen species (ROS) levels and resulting oxidative damage leads to modification in MSR gene expression. MSRs themselves are good candidates for direct antioxidants since cyclic oxidation and reduction of methionine residues could function as an efficient pathway to remove ROS in cells. In eukaryotes, senescence and a host of diseases are triggered by methionine oxidation resulting in the disruption of protein structure and function. The substrates of MSR proteins are largely unknown. To date, the first plant MSR substrate to have been identified is the small, plastidic heat shock protein Hsp21. Hsp21 contains a conserved N-terminal region that is highly enriched in methionine residues. This methinine region must be maintained in the reduced form in order to maintain the chaperone-like activity of Hsp21.

The transgenic plant of this embodiment may comprise any polynucleotide encoding a methionine sulfoxide reductase family protein. Preferably, the transgenic plant of this embodiment comprises a polynucleotide encoding a SelR domain having a sequence comprising amino acids 77 to 199 of SEQ ID NO:2; amino acids 79 to 200 of SEQ ID NO: 4; amino acids 91 to 213 of SEQ ID NO: 6; amino acids 79 to 200 of SEQ ID NO: 8; amino acids 80 to 201 of SEQ ID NO: 10. More preferably, the transgenic plant of this embodiment comprises a polynucleotide encoding a methionine sulfoxide reductase family protein having a sequence comprising amino acids 1 to 205 of SEQ ID NO:2; amino acids 1 to 204 of SEQ ID NO: 4; amino acids 1 to 214 of SEQ ID NO: 6; amino acids 1 to 202 of SEQ ID NO: 8; amino acids 1 to 206 of SEQ ID NO: 10.

In another embodiment, the invention provides a transgenic plant transformed with an expression cassette comprising an isolated polynucleotide encoding a homeodomain leucine zipper protein. Homeodomain leucine zipper (HDZip) proteins belong to a family of transcription factors that interact as dimers via a leucine zipper domain and bind DNA in a sequence specific manner via their homeodomains. Based upon sequence, the HDZip family proteins are divided into four classes. The Class I HDZip proteins are suggested to regulate plant response to ABA and may have regulatory roles related to ABA signalling. The Class I HDZip protein members can form heterodimers in vitro; therefore, this class may constitute an interacting network of proteins that mediates responses to environmental stimuli and/or integrates signals to regulate similar sets of target genes.

The transgenic plant of this embodiment may comprise any polynucleotide encoding a homeodomain leucine zipper protein. Preferably, the transgenic plant of this embodiment comprises a polynucleotide encoding a homeobox domain having a sequence comprising amino acids 62 to 116 of SEQ ID NO:12; amino acids 83 to 137 of SEQ ID NO: 14; amino acids 76 to 130 of SEQ ID NO: 16 or a homeobox associated leucine zipper domain having a sequence comprising amino acids 117 to 161 of SEQ ID NO: 12; amino acids 138 to 182 of SEQ ID NO: 14; amino acids 131 to 175 of SEQ ID NO: 16. More preferably, the transgenic plant of this embodiment comprises a polynucleotide encoding a homeodomain leucine zipper protein having a sequence comprising amino acids 1 to 310 of SEQ ID NO:12; amino acids 1 to 331 of SEQ ID NO: 14; amino acids 1 to 340 of SEQ ID NO: 16.

In another embodiment, the invention provides a transgenic plant transformed with an expression cassette comprising an isolated polynucleotide encoding a A20 and AN1 domain containing zinc finger protein. The A20 and AN1 domain containing zinc finger proteins are found in all eukaryotes. These proteins are characterized by the presence of an A20 zinc finger domain containing multiple $Cysteine_2$/$Cysteine_2$ finger motifs and an AN1 zinc finger domain. The AN1 domain is usually found in proteins containing the A20 zinc finger domain. The function of these proteins is well characterized in animal systems, but little is known about the function of these proteins in plants.

The rice OsiSAP1 protein was identified as the first plant protein having both A20 and AN1 zinc finger domains. This protein was found to be associated with multiple stresses. The OsiSAP1 gene is induced in response to environmental stresses such as cold, salt, drought, submergence, wounding, and heavy metals. An ortholog from bean is also known to be inducible when eliciter treated and in response to wounding. When overexpressed in tobacco, OsiSAP1 engenders abiotic stress tolerance. OsiSAP1 does not have a typical nuclear localization signal and thus is believed to function via the zinc finger domains for protein-protein interaction.

The transgenic plant of this embodiment may comprise any polynucleotide encoding a zinc finger protein containing an A20 domain in combination with an AN1 domain. Preferably, the transgenic plant of this embodiment comprises a polynucleotide encoding an A20-like zinc finger having a sequence comprising amino acids 15 to 39 of SEQ ID NO:18; amino acids 13 to 37 of SEQ ID NO: 20; amino acids 15 to 39 of SEQ ID NO: 22; amino acids 14 to 38 of SEQ ID NO: 24; amino acids 14 to 38 of SEQ ID NO: 26; amino acids 40 to 64 of SEQ ID NO: 28; amino acids 15 to 39 of SEQ ID NO: 30; amino acids 19 to 43 of SEQ ID NO: 32; amino acids 13 to 37 of SEQ ID NO: 34; amino acids 19 to 43 of SEQ ID NO: 36; amino acids 18 to 42 of SEQ ID NO: 38; amino acids 15 to 39 of SEQ ID NO: 40; amino acids 15 to 39 of SEQ ID NO: 42; amino acids 19 to 43 of SEQ ID NO: 44 and an AN1-like zinc finger domain having a sequence comprising amino acids 118 to 158 of SEQ ID NO: 18; amino acids 128 to 168 of SEQ ID NO: 20; amino acids 95 to 135 of SEQ ID NO: 22; amino acids 112 to 152 of SEQ ID NO: 24; amino acids 115 to 155 of SEQ ID NO: 26; amino acids 179 to 219 of SEQ ID NO: 28; amino acids 110 to 150 of SEQ ID NO: 30; amino acids 105 to 145 of SEQ ID NO: 32; amino acids 105 to 145 of SEQ ID NO: 34; amino acids 111 to 151 of SEQ ID NO: 36; amino acids 102 to 142 of SEQ ID NO: 38; amino acids 113 to 153 of SEQ ID NO: 40; amino acids 115 to 155 of SEQ ID NO: 42; amino acids 106 to 146 of SEQ ID NO: 44. More preferably, the transgenic plant of this embodiment comprises a polynucleotide encoding a A20 and AN1 domain containing zinc finger protein having a sequence comprising amino acids 1 to 177 of SEQ ID NO:18; amino acids 1 to 187 of SEQ ID NO: 20; amino acids 1 to 154 of SEQ ID NO: 22; amino acids 1 to 171 of SEQ ID NO: 24; amino acids 1 to 174 of SEQ ID NO: 26; amino acids 1 to 239 of SEQ ID NO: 28; amino acids 1 to 169 of SEQ ID NO: 30; amino acids 1 to 164 of SEQ ID NO: 32; amino acids 1 to 164 of SEQ ID NO: 34; amino acids 1 to 170 of SEQ ID NO: 36; amino acids 1 to 161 of SEQ ID NO: 38; amino acids 1 to 172 of SEQ ID NO: 40; amino acids 1 to 174 of SEQ ID NO: 42, amino acids 1 to 165 of SEQ ID NO: 44.

The invention further provides a seed produced by a transgenic plant expressing polynucleotide listed in Table 1, wherein the seed contains the polynucleotide, and wherein the plant is true breeding for increased growth and/or yield under normal or stress conditions and/or increased tolerance to an environmental stress as compared to a wild type variety of the plant. The invention also provides a product produced by or from the transgenic plants expressing the polynucleotide, their plant parts, or their seeds. The product can be obtained using various methods well known in the art. As used herein, the word "product" includes, but not limited to, a foodstuff, feedstuff, a food supplement, feed supplement, cosmetic or pharmaceutical. Foodstuffs are regarded as compositions used for nutrition or for supplementing nutrition. Animal feedstuffs and animal feed supplements, in particular, are regarded as foodstuffs. The invention further provides an agricultural product produced by any of the transgenic plants, plant parts, and plant seeds. Agricultural products include, but are not limited to, plant extracts, proteins, amino acids, carbohydrates, fats, oils, polymers, vitamins, and the like.

In a preferred embodiment, an isolated polynucleotide of the invention comprises a polynucleotide having a sequence selected from the group consisting of the polynucleotide sequences listed in Table 1. These polynucleotides may comprise sequences of the coding region, as well as 5' untranslated sequences and 3' untranslated sequences.

A polynucleotide of the invention can be isolated using standard molecular biology techniques and the sequence information provided herein. Synthetic oligonucleotide primers for polymerase chain reaction amplification can be designed based upon the nucleotide sequence shown in Table 1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to the nucleotide sequences listed in Table 1 can be prepared by standard synthetic techniques, e.g., using an automated DNA synthesizer.

"Homologs" are defined herein as two nucleic acids or polypeptides that have similar, or substantially identical, nucleotide or amino acid sequences, respectively. Homologs include allelic variants, analogs, and orthologs, as defined below. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. The term homolog further encompasses nucleic acid molecules that differ from one of the nucleotide sequences shown in Table 1 due to degeneracy of the genetic code and thus encode the same polypeptide. As used herein, a "naturally occurring" nucleic acid molecule refers to an RNA or DNA molecule having a nucleotide sequence that occurs in nature (e.g., encodes a natural polypeptide).

To determine the percent sequence identity of two amino acid sequences (e.g., one of the polypeptide sequences of Table 1 and a homolog thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence then the molecules are identical at that position. The same type of comparison can be made between two nucleic acid sequences.

Preferably, the isolated amino acid homologs, analogs, and orthologs of the polypeptides of the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence identified in Table 1. In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in Table 1.

The percent sequence identity between two nucleic acid or polypeptide sequences may be determined using, for example, the Vector NTI 9.0 (PC) software package (Invitrogen, 1600 Faraday Ave., Carlsbad, Calif. 92008). When Vector NTI is used, a gap opening penalty of 15 and a gap extension penalty of 6.66 may be used for determining the percent identity of two nucleic acids and a gap opening penalty of 10 and a gap extension penalty of 0.1 may be used for determining the percent identity of two polypeptides. All other Vector NTI parameters may be set at the default settings. For purposes of a multiple alignment (Clustal W algorithm) using Vector NTI, the gap opening penalty is 10, and the gap extension penalty is 0.05 with blosum62 matrix. Alternatively, Align 2.0 (Myers and Miller (1989) CABIOS 4, 11-17) may be used, with all parameters set to default settings. It is to be understood that for the purposes of determining sequence identity when comparing a DNA sequence to an RNA sequence, a thymidine nucleotide is equivalent to a uracil nucleotide.

Nucleic acid molecules corresponding to homologs, analogs, and orthologs of the polypeptides listed in Table 1 can be isolated based on their identity to said polypeptides, using the polynucleotides encoding the respective polypeptides or primers based thereon, as hybridization probes according to standard hybridization techniques under stringent hybridization conditions. As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10× Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; well known in the art (see, for example, Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology Hybridization with Nucleic Acid Probes, Part I, Chapter 2, Elsevier, N.Y., 1993). Preferably, an isolated nucleic acid molecule of the invention that hybridizes under stringent or highly stringent conditions to a nucleotide sequence listed in Table 1 corresponds to a naturally occurring nucleic acid molecule.

There are a variety of methods that can be used to produce libraries of potential homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

Additionally, optimized nucleic acids can be created. Preferably, an optimized nucleic acid encodes a polypeptide that has a function similar to those of the polypeptides listed in Table 1 and/or modulates a plant's growth and/or yield under normal and/or water-limited conditions and/or tolerance to an environmental stress, and more preferably increases a plant's growth and/or yield under normal and/or water-limited conditions and/or tolerance to an environmental stress upon its overexpression in the plant. As used herein, "optimized" refers to a nucleic acid that is genetically engineered to increase its expression in a given plant or animal. To provide plant optimized nucleic acids, the DNA sequence of the gene can be modified to: 1) comprise codons preferred by highly expressed plant genes; 2) comprise an A+T content in nucleotide base composition to that substantially found in plants; 3) form a plant initiation sequence; 4) to eliminate sequences that cause destabilization, inappropriate polyadenylation, degradation and termination of RNA, or that form secondary structure hairpins or RNA splice sites; or 5) elimination of antisense open reading frames. Increased expression of nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

An isolated polynucleotide of the invention can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots, whereas the XTA codon is avoided in both monocots and dicots. Optimized nucleic acids of this invention also preferably have CG and TA doublet avoidance indices closely approximating those of the chosen host plant. More preferably, these indices deviate from that of the host by no more than about 10-15%.

The invention further provides an isolated recombinant expression vector comprising a polynucleotide as described above, wherein expression of the vector in a host cell results in the plant's increased growth and/or yield under normal or water-limited conditions and/or increased tolerance to environmental stress as compared to a wild type variety of the host cell. The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in a bacterial or plant host cell when the vector is introduced into the host cell). The term "regulatory sequence" is intended to include promoters, enhancers, and other expression control elements (e.g., polyadenylation signals). Such regulatory sequences are well known in the art. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides encoded by nucleic acids as described herein.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J 3:2723-2730), the super promoter (U.S. Pat. No. 5,955,646), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssu-RUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoters from tobacco, *Arabidopsis*, and maize are inducible by infection with a pathogen; and the Adh1 promoter is induced by hypoxia and cold stress. Plant gene expression can also be facilitated via an inducible promoter (For a review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2: 397-404), and an ethanol inducible promoter (PCT Application No. WO 93/21334).

In one preferred embodiment of the present invention, the inducible promoter is a stress-inducible promoter. For the purposes of the invention, stress-inducible promoters are preferentially active under one or more of the following stresses: sub-optimal conditions associated with salinity, drought, nitrogen, temperature, metal, chemical, pathogenic, and oxidative stresses. Stress inducible promoters include, but are not limited to, Cor78 (Chak et al., 2000, Planta 210: 875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115:569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rha1 (Terryn et al., 1993, Plant Cell 5:1761-9; Terryn et al., 1992, FEBS Lett. 299(3):287-90), ARSK1 (Atkinson et al., 1997, GenBank Accession #L22302, and PCT Application No. WO 97/20057), PtxA (Plesch et al., GenBank Accession #X67427), SbHRGP3 (Ahn et al., 1996, Plant Cell 8:1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue-preferred and organ-preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, petal-preferred, sepal-preferred, pedicel-preferred, silique-preferred, stem-preferred, root-preferred promoters, and the like. Seed-preferred promoters are preferentially expressed during seed development and/or germination. For example, seed-preferred promoters can be embryo-preferred, endosperm-preferred, and seed coat-preferred (See Thompson et al., 1989, BioEssays 10:108). Examples of seed-preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3): 459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

In a preferred embodiment of the present invention, the polynucleotides listed in Table 1 are expressed in plant cells from higher plants (e.g., the spermatophytes, such as crop plants). A polynucleotide may be "introduced" into a plant cell by any means, including transfection, transformation or transduction, electroporation, particle bombardment, agroinfection, and the like. Suitable methods for transforming or transfecting plant cells are disclosed, for example, using particle bombardment as set forth in U.S. Pat. Nos. 4,945,050; 5,036,006; 5,100,792; 5,302,523; 5,464,765; 5,120,657; 6,084,154; and the like. More preferably, the transgenic corn seed of the invention may be made using *Agrobacterium* transformation, as described in U.S. Pat. Nos. 5,591,616; 5,731,179; 5,981,840; 5,990,387; 6,162,965; 6,420,630, U.S. patent application publication number 2002/0104132, and the like. Transformation of soybean can be performed using for example a technique described in European Patent No. EP 0424047, U.S. Pat. No. 5,322,783, European Patent No. EP 0397 687, U.S. Pat. No. 5,376,543, or U.S. Pat. No. 5,169,770. A specific example of wheat transformation can be found in PCT Application No. WO 93/07256. Cotton may be transformed using methods disclosed in U.S. Pat. Nos. 5,004,863; 5,159,135; 5,846,797, and the like. Rice may be transformed using methods disclosed in U.S. Pat. Nos. 4,666,844; 5,350,688; 6,153,813; 6,333,449; 6,288,312; 6,365,807; 6,329,571, and the like. Other plant transformation methods are disclosed, for example, in U.S. Pat. Nos. 5,932,782; 6,153,811; 6,140,553; 5,969,213; 6,020,539, and the like. Any plant transformation method suitable for inserting a transgene into a particular plant may be used in accordance with the invention.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and may be transiently expressed or transiently active.

Another aspect of the invention pertains to an isolated polypeptide having a sequence selected from the group consisting of the polypeptide sequences listed in Table 1. An "isolated" or "purified" polypeptide is free of some of the cellular material when produced by recombinant DNA techniques, or chemical precursors or other chemicals when chemically synthesized. The language "substantially free of cellular material" includes preparations of a polypeptide in which the polypeptide is separated from some of the cellular components of the cells in which it is naturally or recombinantly produced. In one embodiment, the language "substantially free of cellular material" includes preparations of a polypeptide of the invention having less than about 30% (by dry weight) of contaminating polypeptides, more preferably less than about 20% of contaminating polypeptides, still more preferably less than about 10% of contaminating polypeptides, and most preferably less than about 5% contaminating polypeptides.

The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities are abundant and well known to one skilled in the art.

The invention is also embodied in a method of producing a transgenic plant comprising at least one polynucleotide listed in Table 1, wherein expression of the polynucleotide in the plant results in the plant's increased growth and/or yield under normal or water-limited conditions and/or increased tolerance to an environmental stress as compared to a wild type variety of the plant comprising the steps of: (a) introducing into a plant cell an expression vector comprising at least one polynucleotide listed in Table 1, and (b) generating from the plant cell a transgenic plant that expresses the polynucleotide, wherein expression of the polynucleotide in the transgenic plant results in the plant's increased growth and/or yield under normal or water-limited conditions and/or increased tolerance to environmental stress as compared to a wild type variety of the plant. The plant cell may be, but is not limited to, a protoplast, gamete producing cell, and a cell that regenerates into a whole plant. As used herein, the term "transgenic" refers to any plant, plant cell, callus, plant tissue, or plant part, that contains at least one recombinant polynucleotide listed in Table 1. In many cases, the recombinant polynucleotide is stably integrated into a chromosome or stable extra-chromosomal element, so that it is passed on to successive generations.

The present invention also provides a method of increasing a plant's growth and/or yield under normal or water-limited conditions and/or increasing a plant's tolerance to an environmental stress comprising the steps of increasing the expression of at least one polynucleotide listed in Table 1 in the plant. Expression of a protein can be increased by any method known to those of skill in the art.

The effect of the genetic modification on plant growth and/or yield and/or stress tolerance can be assessed by growing the modified plant under normal and. or less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, metabolite composition, etc., using methods known to those of skill in biotechnology.

The invention is further illustrated by the following examples, which are not to be construed in any way as imposing limitations upon the scope thereof.

EXAMPLE 1

Cloning of Full-Length cDNAs

The full-length DNA sequence of the *Physcomitrella patens* EST65 methionine sulfoxide reductase family protein (SEQ ID NO:43) was blasted against proprietary databases of canola, soybean, rice, maize, linseed, sunflower, barley, and wheat cDNAS at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. One homolog from canola, two homologs from rice, one homolog from soybean, and one homolog from wheat were identified. The degrees of amino acid identity and similarity of these sequences to the respective closest known public sequences are indicated in Tables 2 through 6 (Align 2.0).

TABLE 2

Comparison of BN51364980 (SEQ ID NO: 2) to known methionine sulfoxide reductases

| Public Database Accession # | Species | Sequence Identity (%) |
|---|---|---|
| NP_564640 | *Arabidopsis thaliana* | 82.00% |
| AAM65202 | *A. thaliana* | 66.70% |
| BAD35399 | *O. sativa* | 56.10% |
| NP_001057620 | *O. sativa* | 55.80% |
| ZP_01592095 | *Geobacter lovleyi* SZ | 42.40% |

TABLE 3

Comparison of OS34096188 (SEQ ID NO: 4) to known methionine sulfoxide reductases

| Public Database Accession # | Species | Sequence Identity (%) |
|---|---|---|
| ABE84787 | *Medicago truncatula* | 72.60% |
| NP_567639 | *A. thaliana* | 61.90% |
| AAM62876 | *A. thaliana* | 61.00% |
| NP_567271 | *A. thaliana* | 58.70% |
| EAY98001 | *O. sativa* | 57.80% |

TABLE 4

Comparison of OS32583643 (SEQ ID NO: 6) to known methionine sulfoxide reductases

| Public Database Accession # | Species | Sequence Identity (%) |
|---|---|---|
| NP_001057620 | *O. sativa* | 99.10% |
| BAD35399 | *O. sativa* | 74.80% |
| NP_564640 | *A. thaliana* | 59.60% |
| AAM65202 | *A. thaliana* | 53.70% |
| YP_846684 | *Syntrophobacter fumaroxidans* MPOB | 44.20% |

TABLE 5

Comparison of GM53626178 (SEQ ID NO: 8) to known methionine sulfoxide reductases

| Public Database Accession # | Species | Sequence Identity (%) |
|---|---|---|
| ABE84787 | M. truncatula | 72.80% |
| NP_567639 | A. thaliana | 60.90% |
| AAM62876 | A. thaliana | 60.90% |
| EAY98001 | O. sativa | 59.10% |
| AAO72582 | O. sativa | 57.60% |

TABLE 6

Comparison of TA56540264 (SEQ ID NO: 10) to known methionine sulfoxide reductases

| Public Database Accession # | Species | Sequence Identity (%) |
|---|---|---|
| EAY98001 | O. sativa | 72.90% |
| NP_001055501 | O. sativa | 69.50% |
| ABE84787 | M. truncatula | 65.50% |
| NP_567639 | A. thaliana | 60.60% |
| AAM62876 | A. thaliana | 59.60% |

The full-length DNA sequence of the *P. patens* EST12 homeodomain leucine zipper protein (SEQ ID NO:44) was blasted against proprietary databases of canola, soybean, rice, maize, linseed, sunflower, barley, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. One homolog from canola, one homolog from soybean, and one homolog from wheat were identified. The degrees of amino acid identity and similarity of these sequences to the respective closest known public sequence are indicated in Tables 7 through 9 (Align 2.0).

TABLE 7

Comparison of BN45206322 (SEQ ID NO: 12) to known homeodomain leucine zipper proteins

| Public Database Accession # | Species | Sequence Identity (%) |
|---|---|---|
| AAR04932 | B. napus | 95.20% |
| AAF73482 | Brassica rapa | 91.30% |
| AAD41726 | A. thaliana | 81.20% |
| NP_195716 | A. thaliana | 69.90% |
| AAK96762 | A. thaliana | 69.60% |

TABLE 8

Comparison of GM48923793 (SEQ ID NO: 14) to known homeodomain leucine zipper proteins

| Public Database Accession # | Species | Sequence Identity (%) |
|---|---|---|
| AAX98670 | G. e max | 56.00% |
| AAK84886 | Phaseolus vulgaris | 51.60% |
| CAA64417 | Solanum lycopersicum | 47.40% |
| BAA05624 | Daucus carota | 46.70% |
| AAF01765 | G. max | 44.00% |

TABLE 9

Comparison of TA55969932 (SEQ ID NO: 16) to known homeodomain leucine zipper proteins

| Public Database Accession # | Species | Sequence Identity (%) |
|---|---|---|
| NP_001048008 | O. sativa | 74.00% |
| EAY87390 | O. sativa | 73.80% |
| NP_001061807 | O. sativa | 49.90% |
| AAD37698 | O. sativa | 49.60% |
| AAS83417 | O. sativa | 46.30% |

The full-length DNA sequence of the *P. patens* EST307 A20 and AN1 domain containing zinc finger protein (SEQ ID NO:45) was blasted against proprietary databases of canola, soybean, rice, maize, linseed, sunflower, barley, and wheat cDNAS at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Two homologs from canola, one homolog from barley, two homologs from corn, two homologs from linseed, three homolog from soybean, three homologs from rice, and one homolog from wheat were identified. The degrees of amino acid identity and similarity of these sequences to the respective closest known public sequences are indicated in Tables 10 through 22 (Align 2.0).

TABLE 10

Comparison of BN47310186 (SEQ ID NO: 18) to known A20 and AN1 domain containing zinc finger proteins

| Public Database Accession # | Species | Sequence Identity (%) |
|---|---|---|
| NP_564585 | A. thaliana | 88.70% |
| AAN71995 | A. thaliana | 88.10% |
| ABL67658 | Citrus cv. Shiranuhi | 59.40% |
| AAQ84334 | O. sativa | 56.00% |
| AAD38146 | Prunus armeniaca | 55.20% |

TABLE 11

Comparison of BN51359456 (SEQ ID NO: 20) to known A20 and AN1 domain containing zinc finger proteins

| Public Database Accession # | Species | Sequence Identity (%) |
|---|---|---|
| NP_190848 | A. thaliana | 71.60% |
| AAK68811 | A. thaliana | 71.10% |
| NP_565844 | A. thaliana | 66.00% |
| ABE93196 | M. truncatula | 51.10% |
| AAN71995 | A. thaliana | 47.10% |

TABLE 12

Comparison of HV62552639 (SEQ ID NO: 22) to known A20 and AN1 domain containing zinc finger proteins

| Public Database Accession # | Species | Sequence Identity (%) |
|---|---|---|
| NP_001055132 | O. sativa | 70.10% |
| AAR96005 | Musa acuminata | 51.80% |
| AAA33773 | P. vulgaris | 42.60% |
| EAZ09556 | O. sativa | 40.80% |
| EAZ45178 | O. sativa | 39.40% |

TABLE 13

Comparison of ZM61995511 (SEQ ID NO: 24) to known
A20 and AN1 domain containing zinc finger proteins

| Public Database Accession # | Species | Sequence Identity (%) |
|---|---|---|
| AAQ84334 | O. sativa | 79.50% |
| AAX14637 | Z. mays | 77.00% |
| EAZ01657 | O. sativa | 71.70% |
| ABL67658 | Citrus cv. Shiranuhi | 69.50% |
| NP_001046186 | O. sativa | 65.90% |

TABLE 14

Comparison of LU61567101 (SEQ ID NO: 26) to known A20
and AN1 domain containing zinc finger proteins

| Public Database Accession # | Species | Sequence Identity (%) |
|---|---|---|
| CAE73100 | Caenorhabditis briggsae | 29.30% |
| NP_190848 | A. thaliana | 29.20% |
| XP_001357850 | Drosophila pseudoobscura | 29.20% |
| EAY92150 | O. sativa | 29.10% |
| ABL97956 | B. rapa | 28.90% |

TABLE 15

Comparison of LU61893412 (SEQ ID NO: 28) to known
A20 and AN1 domain containing zinc finger proteins

| Public Database Accession # | Species | Sequence Identity (%) |
|---|---|---|
| ABL67658 | Citrus cv. Shiranuhi | 67.40% |
| AAD38146 | P. armeniaca | 64.60% |
| AAQ84334 | O. sativa | 61.70% |
| ABN08135 | M. truncatula | 61.50% |
| AAN71995 | A. thaliana | 61.00% |

TABLE 16

Comparison of OS39781852 (SEQ ID NO: 30) to known
A20 and AN1 domain containing zinc finger proteins

| Public Database Accession # | Species | Sequence Identity (%) |
|---|---|---|
| EAZ45178 | O. sativa | 99.40% |
| EAZ09556 | O. sativa | 99.40% |
| NP_001063521 | O. sativa | 65.90% |
| ABI23728 | Chrysanthemum x morifolium | 58.80% |
| AAA33773 | P. vulgaris | 47.30% |

TABLE 17

Comparison of OS34701560 (SEQ ID NO: 32) to known
A20 and AN1 domain containing zinc finger proteins

| Public Database Accession # | Species | Sequence Identity (%) |
|---|---|---|
| NP_565844 | A. thaliana | 58.80% |
| ABE93196 | M. truncatula | 56.40% |
| NP_190848 | A. thaliana | 55.60% |
| AAK68811 | A. thaliana | 55.60% |
| ABL67658 | Citrus cv. Shiranuhi | 48.30% |

TABLE 18

Comparison of OS36821256 (SEQ ID NO: 34) to known
A20 and AN1 domain containing zinc finger proteins

| Public Database Accession # | Species | Sequence Identity (%) |
|---|---|---|
| EAZ45178 | O. sativa | 63.00% |
| EAZ09556 | O. sativa | 63.00% |
| ABI23728 | Chrysanthemum x morifolium | 51.10% |
| AAA33773 | P. vulgaris | 43.40% |
| AAX14637 | Z. mays | 43.30% |

TABLE 19

Comparison of GM51659494 (SEQ ID NO: 36) to known
A20 and AN1 domain containing zinc finger proteins

| Public Database Accession # | Species | Sequence Identity (%) |
|---|---|---|
| AAA33773 | P. vulgaris | 58.00% |
| EAZ09556 | O. sativa | 54.20% |
| EAZ45178 | O. sativa | 54.20% |
| NP_566429 | A. thaliana | 51.50% |
| ABI23728 | Chrysanthemum x morifolium | 44.40% |

TABLE 20

Comparison of GM49780101 (SEQ ID NO: 38) to known
A20 and AN1 domain containing zinc finger proteins

| Public Database Accession # | Species | Sequence Identity (%) |
|---|---|---|
| ABN08135 | M. truncatula | 76.70% |
| ABL67658 | Citrus cv. Shiranuhi | 66.30% |
| AAD38146 | P. armeniaca | 64.60% |
| AAQ84334 | O. sativa | 64.40% |
| AAX14637 | Z. mays | 61.90% |

TABLE 21

Comparison of GM59637305 (SEQ ID NO: 40) to known
A20 and AN1 domain containing zinc finger proteins

| Public Database Accession # | Species | Sequence Identity (%) |
|---|---|---|
| AAD38146 | P. armeniaca | 69.30% |
| ABL67658 | Citrus cv. Shiranuhi | 68.60% |
| AAQ84334 | O. sativa | 65.90% |
| AAX14637 | Z. mays | 64.00% |
| NP_564585 | A. thaliana | 63.70% |

TABLE 22

Comparison of TA55974113 (SEQ ID NO: 42) to known
A20 and AN1 domain containing zinc finger proteins

| Public Database Accession # | Species | Sequence Identity (%) |
|---|---|---|
| EAZ09556 | O. sativa | 73.20% |
| EAZ45178 | O. sativa | 72.60% |
| ABI23728 | Chrysanthemum x morifolium | 54.20% |
| NP_001063521 | O. sativa | 49.00% |
| AAA33773 | P. vulgaris | 46.10% |

EXAMPLE 2

Water Stress-Tolerant *Arabidopsis* Plants

The polynucleotides of Table 1 are ligated into a binary vector containing a selectable marker. The resulting recombinant vector contains the corresponding gene in the sense orientation under a constitutive promoter. The recombinant vectors are transformed into an *Agrobacterium tumefaciens* strain according to standard conditions. *A. thaliana* ecotype Col-0 or C24 are grown and transformed according to standard conditions. T1 and T2 plants are screened for resistance to the selection agent conferred by the selectable marker gene. T3 seeds are used in greenhouse or growth chamber experiments.

Approximately 3-5 days prior to planting, seeds are refrigerated for stratification. Seeds are then planted, fertilizer is applied and humidity is maintained using transparent domes. For the "biomass" assay, plants are grown in a greenhouse at 22° C. with photoperiod of 16 hours light/8 hours dark and watered twice a week. For the "cycling drought" assay, plants are grown in a growth chamber at 22° C. with 55% relative humidity with photoperiod was set at 16 h light/8 h dark and watered on days 0, 18, and 25 after sowing.

At 19 and 22 days, plant area, leaf area, biomass, color distribution, color intensity, and growth rate for each plant are measured using a commercially available imaging system. Biomass is calculated as the total plant leaf area at the last measuring time point. Growth rate is calculated as the plant leaf area at the last measuring time point minus the plant leaf area at the first measuring time point divided by the plant leaf area at the first measuring time point. Health index is calculated as the dark green leaf area divided by the total plant leaf area. Table 23 presents the biomass, growth rate, and health index for independent transformation events (lines) of transgenic plants overexpressing polynucleotides represented as SEQ ID NOs:5, 7, and 13. The percent change of a line compared to pooled wild-type controls was calculated, and the significant (p) value was calculated using a t-test. An event was called positive if percent change was greater than 0 and p<0.1, not significant (NS) if p>0.1 regardless of percent change, and negative if percent change was less than 0 and p<0.1.

TABLE 23

| Gene ID | Result catagory | Number of events called in each result category per assay | | |
|---|---|---|---|---|
| | | Biomass | Growth Rate | Health Index |
| OS32583643 | Positive | 1 | 2 | 2 |
| SEQ ID NO: 5 | NS | 8 | 5 | 6 |
| | negative | 1 | 3 | 2 |
| GM53626178 | Positive | 6 | 2 | 1 |
| SEQ ID NO: 7 | NS | 3 | 6 | 7 |
| | negative | 1 | 2 | 2 |
| GM48923793 | Positive | 3 | 1 | 4 |
| SEQ ID NO: 13 | NS | 2 | 2 | 4 |
| | negative | 5 | 7 | 2 |

EXAMPLE 3

Nitrogen Stress Tolerant *Arabidopsis* Plants

The polynucleotides of Table 1 are ligated into a binary vector containing a selectable marker. The resulting recombinant vector contains the corresponding gene in the sense orientation under a constitutive promoter. The recombinant vectors are transformed into an *A. tumefaciens* strain according to standard conditions. *A. thaliana* ecotype Col-0 or C24 are grown and transformed according to standard conditions. T1 and T2 plants are screened for resistance to the selection agent conferred by the selectable marker gene.

Plants are grown in flats using a substrate that contains no organic components. Each flat is wet with water before seedlings resistant to the selection agent are transplanted onto substrate. Plants are grown in a growth chamber set to 22° C. with a 55% relative humidity with photoperiod set at 16 h light/8 h dark. A controlled low or high nitrogen nutrient solution is added to waterings on Days 12, 15, 22 and 29. Watering without nutrient solution occurs on Days 18, 25, and 32. Images of all plants in a tray are taken on days 26, 30, and 33 using a commercially available imaging system. At each imaging time point, biomass and plant phenotypes for each plant are measured including plant area, leaf area, biomass, color distribution, color intensity, and growth rate.

EXAMPLE 4

Stress-Tolerant Rapeseed/Canola Plants

Canola cotyledonary petioles of 4 day-old young seedlings are used as explants for tissue culture and transformed according to EP1566443. The commercial cultivar Westar (Agriculture Canada) is the standard variety used for transformation, but other varieties can be used. *A. tumefaciens* GV3101:pMP90RK containing a binary vector is used for canola transformation. The standard binary vector used for transformation is pSUN (WO02/00900), but many different binary vector systems have been described for plant transformation (e.g. An, G. in *Agrobacterium* Protocols, Methods in Molecular Biology vol 44, pp 47-62, Gartland K M A and M R Davey eds. Humana Press, Totowa, N.J.). A plant gene expression cassette comprising a selection marker gene and a plant promoter regulating the transcription of the cDNA encoding the polynucleotide is employed. Various selection marker genes can be used including the mutated acetohydroxy acid synthase (AHAS) gene disclosed in U.S. Pat. Nos. 5,767,366 and 6,225,105. A suitable promoter is used to regulate the trait gene to provide constitutive, developmental, tissue or environmental regulation of gene transcription.

Canola seeds are surface-sterilized in 70% ethanol for 2 min, incubated for 15 min in 55° C. warm tap water and then in 1.5% sodium hypochlorite for 10 minutes, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 pMol/m$^2$s, 16 hours light). The cotyledon petiole explants with the cotyledon attached are excised from the in vitro seedlings, and inoculated with *Agrobacterium* by dipping the cut end of the petiole explant into the bacterial suspension. The explants are then cultured for 3 days on MS medium including vitamins containing 3.75 mg/l BAP, 3% sucrose, 0.5 g/l MES, pH 5.2, 0.5 mg/l GA3, 0.8% Oxoidagar at 24° C., 16 hours of light. After three days of co-cultivation with *Agrobacterium*, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants start to develop shoots, they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP, 0.1 mg/l IBA, 300 mg/l timentin and selection agent).

Samples from both in vitro and greenhouse material of the primary transgenic plants (T0) are analyzed by qPCR using Tag Man probes to confirm the presence of T-DNA and to determine the number of T-DNA integrations.

Seed is produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their stress tolerance, for example, in assays similar to those described in Examples 2 and 3, and for yield, both in the greenhouse and in field studies.

EXAMPLE 5

Screening for Stress-Tolerant Rice Plants

Transgenic rice plants comprising a polynucleotide of Table 1 are generated using known methods. Approximately 15 to 20 independent transformants (T0) are generated. The primary transformants are transferred from tissue culture chambers to a greenhouse for growing and harvest of T1 seeds. Five events of the T1 progeny segregated 3:1 for presence/absence of the transgene are retained. For each of these events, 10 T1 seedlings containing the transgene (hetero- and homozygotes), and 10 T1 seedlings lacking the transgene (nullizygotes) are selected by visual marker screening. The selected T1 plants are transferred to a greenhouse. Each plant receives a unique barcode label to link unambiguously the phenotyping data to the corresponding plant. The selected T1 plants are grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes are grown side-by-side at random positions. From the stage of sowing until the stage of maturity, the plants are passed several times through a digital imaging cabinet. At each time point digital, images (2048×1536 pixels, 16 million colours) of each plant are taken from at least 6 different angles.

The data obtained in the first experiment with T1 plants are confirmed in a second experiment with T2 plants. Lines that have the correct expression pattern are selected for further analysis. Seed batches from the positive plants (both hetero- and homozygotes) in T1 are screened by monitoring marker expression. For each chosen event, the heterozygote seed batches are then retained for T2 evaluation. Within each seed batch, an equal number of positive and negative plants are grown in the greenhouse for evaluation.

Transgenic plants are screened for their improved growth and/or yield and/or stress tolerance, for example, using assays similar to those described in Examples 2 and 3, and for yield, both in the greenhouse and in field studies.

EXAMPLE 6

Stress-Tolerant Soybean Plants

The polynucleotides of Table 1 are transformed into soybean using the methods described in commonly owned copending international application number WO 2005/121345, the contents of which are incorporated herein by reference.

The transgenic plants generated are then screened for their improved growth under water-limited conditions and/or drought, salt, and/or cold tolerance, for example, using assays similar to those described in Examples 2 and 3, and for yield, both in the greenhouse and in field studies.

EXAMPLE 7

Stress-Tolerant Wheat Plants

The polynucleotides of Table 1 are transformed into wheat using the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved growth and/or yield under water-limited conditions and/or stress tolerance, for example, in assays similar to those described in Examples 2 and 3, and for yield, both in the greenhouse and in field studies.

EXAMPLE 8

Stress-Tolerant Corn Plants

The polynucleotides of Table 1 are transformed into immature embryos of corn using *Agrobacterium*. After imbibition, embryos are transferred to medium without selection agent. Seven to ten days later, embryos are transferred to medium containing selection agent and grown for 4 weeks (two 2-week transfers) to obtain transformed callus cells. Plant regeneration is initiated by transferring resistant calli to medium supplemented with selection agent and grown under light at 25-27° C. for two to three weeks. Regenerated shoots are then transferred to rooting box with medium containing selection agent. Plantlets with roots are transferred to potting mixture in small pots in the greenhouse and after acclimatization are then transplanted to larger pots and maintained in greenhouse till maturity.

Each of these plants is uniquely labeled, sampled and analyzed for transgene copy number. Transgene positive and negative plants are marked and paired with similar sizes for transplanting together to large pots. This provides a uniform and competitive environment for the transgene positive and negative plants. The large pots are watered to a certain percentage of the field water capacity of the soil depending on the severity of water-stress desired. The soil water level is maintained by watering every other day. Plant growth and physiology traits such as height, stem diameter, leaf rolling, plant wilting, leaf extension rate, leaf water status, chlorophyll content and photosynthesis rate are measured during the growth period. After a period of growth, the above ground portion of the plants is harvested, and the fresh weight and dry weight of each plant are taken. A comparison of the drought tolerance phenotype between the transgene positive and negative plants is then made.

The pots are covered with caps that permit the seedlings to grow through but minimize water loss. Each pot is weighed periodically and water added to maintain the initial water content. At the end of the experiment, the fresh and dry weight of each plant is measured, the water consumed by each plant is calculated and WUE of each plant is computed. Plant growth and physiology traits such as WUE, height, stem diameter, leaf rolling, plant wilting, leaf extension rate, leaf water status, chlorophyll content and photosynthesis rate are measured during the experiment. A comparison of WUE phenotype between the transgene positive and negative plants is then made.

These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Water is then withheld. Plant growth and physiology traits such as height, stem diameter, leaf rolling, plant wilting, leaf extension rate, leaf water status, chlorophyll content and photosynthesis rate are measured as stress intensity increases. A comparison of the dessication tolerance phenotype between transgene positive and negative plants is then made.

Segregating transgenic corn seeds for a transformation event are planted in small pots for testing in a cycling drought assay. These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Plants are then repeatedly watered to saturation at a fixed interval of time. This water/drought cycle is repeated for the duration of the experiment. Plant growth and physiology traits such as height, stem diameter, leaf rolling, leaf extension rate, leaf water status, chlorophyll content and photosynthesis rate are measured during the growth period. At the end of the experiment, the plants are harvested for above-ground fresh and dry weight. A comparison of the cycling drought tolerance phenotype between transgene positive and negative plants is then made.

In order to test segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Each plot is sown with seed segregating for the presence of a single transgenic insertion event. A Taqman transgene copy number assay is used on leaf samples to differentiate the transgenics from null-segregant control plants. Plants that have been genotyped in this manner are also scored for a range of phenotypes related to drought-tolerance, growth and yield. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plants are used as the replicate unit per event.

In order to test non-segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Trial layout is designed to pair a plot containing a non-segregating transgenic event with an adjacent plot of null-segregant controls. A null segregant is progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

To perform multi-location testing of transgenic corn for drought tolerance and yield, five to twenty locations encompassing major corn growing regions are selected. These are widely distributed to provide a range of expected crop water availabilities based on average temperature, humidity, precipitation and soil type. Crop water availability is not modified beyond standard agronomic practices. Trial layout is designed to pair a plot containing a non-segregating transgenic event with an adjacent plot of null-segregant controls. A range of phenotypes related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

APPENDIX cDNA sequence of BN51364980 from canola (SEQ ID NO: 1):

```
atggcttcttctagttgtttcaccattcagtcacgtttcgtctcagcgag
aacaaagctcgattcaatctccaaaccgagtctctccggattcgcttgtc
gttctcttacaaaacccagaaacttgaatctctctgttcttcttcggtgt
tccatgggttcctttaactcttctcagaaatcagacaacgtccaagaagc
tgcaaagagtgactttgcttcaataagtgaaggtgagtggaagaaacggc
taacaccagaacagtattacatcaccagacagaagggaacagagagagct
ttcactggtgagtattggaatacaaagaccccaggagtatacaaatgtat
ctgttgcgacacgccactgtttgactcatcaacaaagcttgatagtggaa
ccgggtggccatcgtattaccaacctattggaaacaatgtgaagtcaaag
ctggacctctctatcatcttcatgcctagacaagaagttatctgtgctgt
ttgtaacgccatcttggtcatgtcttcgatgacggtccacgaccaaccg
gaaaacgatattgcctcaacagtgctgctctgaaacttgagtcattggag
agaacaagagaatga
```

The BN51364980 cDNA is translated into the following amino acid sequence (SEQ ID NO:2):

```
masssscftiqsrfvsartkldsiskpslsgfacrsltkprnlnlsvllrc
smgsfnssqksdnvqeaaksdfasisegewkkrltpeqyyitrqkgtera
ftgeywntktpgvykciccdtplfdsstkldsgtgwpsyyqpignnvksk
ldlsiifmprqevicavcnahlghvfddgprptgkryclnsaalkleslertre
``` cDNA sequence of OS34096188 from rice (SEQ ID NO:3):

```
atgggcttcaatattctgagaaccacttccatctccactcctatctcttc
ctccaaatccaaacccatttctcaactcttcttcgttcttctccttcca
ccattttcccccaaagtccgttactccaccactcttttcgtttctgcc
accccttcttcactctccatcccaagcttggttttcgtggtgggattgt
ggccatggccgcacctggctctctccgcaaatccgaggaagagtggcgcg
caattctctcccctgaacagtttcggatcctcaggcaaaagggcaccgag
ttccctggaacaggagagtatgacaagttctatgaagagggagtttacaa
ctgtgctggttgtgggactccactctacaggtccataacaaaattcaatt
ctggttgtggctggccagccttctatgaggggattcccggagccataaat
cgcaatccggatcctgatgggatgaggacagaaataacgtgtgctgcttg
tgggggacatctaggtcacgtcttaaggagaaggattccaacaccca
ctaacgaacgccattgtgtcaatagcatttcgctgaaatttgcgccagcc
aattcttattcttaa
```

The OS34096188 cDNA is translated into the following amino acid sequence (SEQ ID NO:4):

```
mgfnilrttsistpissskskpifstllrsspstifppksvtpttlfvsa
tpffftlhpklgfrggivamaapgslrkseeewrailspeqfrilrqkgte
fpgtgeydkfyeegvyncagcgtplyrsitkfnsgcgwpafyegipgain
rnpdpdgmrteitcaacgghlghvfkgegfptptnerhcvnsislkfapa
nsys
``` cDNA sequence of OS32583643 from rice (SEQ ID NO:5):

```
atggccatgcggcaatacgcggctgctaccgctgcctcctccagtttcag
agcacgtccacgggcgcgcccctcctgcctcccagccgccgccctgccct
tggcgccttgctgtggtgtggcgtggagccgtgctagctacaggcgagcc
tccgttcgtgccatgggtgccgcttcatcgtcttcgtcgtcgtcgtc
gtctccgtcgccgcagggtcaagcccaagcccaagcccaaggtaaaccga
actacagtacatctctgactgatgaggagtggaggaagcgcctgacaaaa
gatcagtattacattactcggcagaagggcacagaaagagcatttactgg
ggaatactggaacaccaaaaccccgggcatctaccattgtgtctgctgtg
acacccctcttttgagtcatcgaccaaatttgatagtggtactgggtgg
ccgtcatattatcaacccattggagataatgtaaagtgcaagcttgatat
gtccatcatattcatgcctcggactgaggtgctgtgtgctgtctgtgacg
ctcatctggggcacgtgtttgatgatgggccacgaccaacagggaaaga
tactgtatcaatagcgcatctctcaagctgaagaagacccagtag
```

The 0S32583643 cDNA is translated into the following amino acid sequence (SEQ ID NO:6):

```
mamrqyaaataasssfrarprarpsclpaaalplapccgvawsrasyrra
svramgaassssssssssspspqggqaqaqaqgkpnystsltdeewrkrltk
dqyyitrqkgteraftgeywntktpgiyhcvccdtplfesstkfdsgtgw
psyyqpigdnvkckldmsiifmprtevlcavcdahlghvfddgprptgkr
ycinsaslklkktq
``` cDNA sequence of GM53626178 from soybean (SEQ ID NO:7):

```
atgggattgagtattctgagaagcacttccatttccactcctatctcttc
ctccaaatccaaacccatttctcaactcttgttcgttcatctttcgcct
ccatttccccacaaagtgtgttactccaccactcttttcgtttctgcc
accccttcttcaccgcctcacccaagcgcggctttcgtggtgggattgt
ggccatggccgccgctggctcgctccgcaaatcagaggaagagtggcgcg
cagttctctcccctgaacagtttcgtattctcaggcaaaagggcaccgag
ttccctggaacaggagagtatgacaagttctttgatgagggagtttacaa
ctgtgctggttgtgggacacctctctacaggtccttaacaaaattcaatt
ctggttgtggctggccagccttctatgaggggattcctggagccataaat
```

```
cgcaatccggaccctgatgggatgaggacagaaataacgtgtgctgcttg tgggggacatctaggtcacgtcttttaaaggagaaggattctccaacgccca ctaacgaacgccattgtgtcaatagcatttcactgaaatttgcgccagcc aattcttaa
```

The GM53626178 cDNA is translated into the following amino acid sequence (SEQ ID NO:8):

```
mglsilrstsistpissskskpifstlvrssfasisptkcvtpttlfvsa tpfftaspkrgfrggivamaaagslrkseeewravlspeqfrilrqkgte fpgtgeydkffdegvyncagcgtplyrsltkfnsgcgwpafyegipgain rnpdpdgmrteitcaacgghlghvfkgegfptptnerhcvnsisikfapa ns
``` cDNA sequence of TA56540264 from wheat (SEQ ID NO:9):

```
atggcgtcgcccacgcccacccggccacgcggcccctctcatcgctccc gtccctcctcctcgcccgctcctcctccgccgccaccgccgccgcgtcgt ccgcccgccccgcctccctctccctctcgtgctcgcggtcgcgggcgcgg gcctactgcccagccggacgacggttgccgggcgccgtggtggctatgtc gtcggcggcgcccacgccggggcccgtgcagaagtcggaggaggagtggg aggccgtcctcacgccggagcagttccgcatcctccgccgcaagggcacc gagtatcctggaacaggtgaatatgacaagttcttcagtgagggtattta cggatgtgctggctgtggaaccccttgtacaaatcatctacgaagttca actcagggtgtggttggccagcattctatgaaggatttcctggagccata aaacggacggcggatcctgatggggaggcgaattgagatcacatgtgctgc ttgtgaaggacatctggggcatgtgttcaaagggggaggggttcaacacgc cgactgatgagcgacactgcgtcaacagtatctcactcaagttcgttccg gcctctgaagaggctagttga
```

The TA56540264 cDNA is translated into the following amino acid sequence (SEQ ID NO:10):

```
masphahpatrplsslpslllarsssaataaassarpaslslscsrsrar aycpagrrlpgavvamssaaptpgpvqkseeeweavltpeqfrilrrkgt eypgtgeydkffsegiygcagcgtplyksstkfnsgcgwpafyegfpgai krtadpdgrrieitcaaceghlghvfkgegfntptderhcvnsislkfvp aseeas
``` cDNA sequence of BN45206322 from canola (SEQ ID NO:11):

```
atgatgaagagattaagcagttcagattcagtgggtggtctcatctcttt atgtcccactacttccacagatcagccgaatccaagaagatgcgggagag aatttcagtcgatgctcgaaggttacgaggaggaagaagaagccata accgaggaaagaggacaaaccggtttagccgagaagaagagacggttaaa cattaaccaagttaaagccttggagaaaaatttcgagttagagaacaagc ttgagcctgagaggaaagtgaagttagctcaagaacttggtctccaacct cgtcaagtagctgtttggtttcagaaccgccgtgcgcggtggaagacaaa acagcttgagaaagattacggtgttctcaaaacgcaatacgattctctcc gccataactttgattccctccgccgtgaaaatgaatctcttcttcaagag atcggtaaactaaaagctaagcttaacggagaagaagaaggagatgatgt tgatgaagaagagaacaacttggcgacgatggagagtgatgtttccgtca aggaagaagaagtttcgttgccggagcagatcacagagccgccgtcttct cctccgcagcttctagagcattccgacagtttcaattaccggagtttcac cgacctccgcgaccttcttccgttaaaggccgcggcttcctccgtcgccg ccgctggatcgtcggacagtagcgattcgagcgccgtgttgaacgaggaa agtagctctaacgttacggcggctccggcgacggttccggcggcagttt cttgcagtttgtgaaaatggagcagacggaggatcacgacgactttctga gtggagaagaagcgtgcgggtttttctccgatgaacagccaccgtctctg cactggtattccaccgttgatcagtggaactga
```

The BN45206322 cDNA is translated into the following amino acid sequence (SEQ ID NO:12):

```
mmkrlsssdsvgglislcpttstdqpnprrcgrefqsmlegyeeeeeeai teergqtglaekkrrlninqvkaleknfelenkleperkvklaqelglqp rqvavwfqnrrarwktkqlekdygvlktqydslrhnfdslrrenesllqe igklkaklngeeegddvdeeennlatmesdvsvkeeevslpeqiteppss ppqllehsdsfnyrsftdlrdllplkaaassvaaagssdssdssavlnee sssnvtaapatvpggsflqfvkmeqtedhddflsgeeacgffsdeqppsl hwystvdqwn
``` cDNA sequence of GM48923793 from soybean (SEQ ID NO:13):

```
atggcgggtagtggaagtgccttttccaacatcactagctttcttcgcac ccaacaaccctcttctcaacctctcgattcttctctcttcctctctgcac cttcctctgctcctttcctcggttcgagatccatgatgagttttgatgga gaaggagggaagggtgtaacggctccttcttccgcgcgtttgacatgga cgacaatggggatgagtgcatggacgagtactttcatcaacccgagaaga agcgacgtctctctgcgagccaggttcagtttctagagaagagcttcgag gaggagaacaagcttgaacccgagagaaagaccaaactagccaaagacct tggtttgcagccacggcaagttgctatttggttccagaaccgtagagctc ggtggaagaacaaacagctggagaaggattacgagactctgcatgcaagt tttgagagtctcaagtccaactatgactgtcttctcaaggagaaagacaa gttaaaagctgaggtggcgagcctcactgagaaggtgcttgcaagaggga aacaagaggggcacatgaagcaggctgaaagtgaaagtgaagaaacaaaa ggattattgcatttgcaggaacaggaaccaccccagaggcttttactgca atcagtttcggaggggagaaggatccaaagtctcttctgtcgttggggtt
```

-continued gtaaacaggaagatatcagttcagcaaggagtgacattttggattcagat agtccacattacaccgatggagttcactctgcgctgctagagcatggtga ttcttcttatgtgtttgagcctgatcaatcagatatgtcacaagatgaag aagataaccctcagcaagagtctctaccccttcgtacctctttcccaaactt gaagaagatgtggattactccgacccacctgaaagttcttgtaattttgg atttcctgaggaagatcatgtcctttggacctgggcttactactaa The GM48923793 cDNA is translated into the following amino acid sequence (SEQ ID NO:14):

magsgsafsnitsflrtqqpssqpldsslflsapssapflgsrsmmsfdg eggkgcngsffrafdmddngdecmdeyfhqpekkrrlsasqvqflekste eenkleperktklakdlglqprqvaiwfqnrrarwknkqlekdyetlhas feslksnydcllkekdklkaevasltekvlargkqeghmkqaeseseetk gllhlqeqeppqrlllqsvsegegskvssvvggckqedissarsdildsd sphytdgvhsallehgdssyvfepdqsdmsqdeednlskslypsylfpkl eedvdysdppesscnfgfpeedhvlwtwayy cDNA sequence of TA55969932 from wheat (SEQ ID NO:15):

atggagcccggccggctcatcttcaacacgtcgggctccggcaacggaca gatgctcttcatggactgcggcgcgggcggcatcgccggcgcggccggca tgttccatcgagggtgagaccggtcctcggcggcatggaagaagggcgc ggcgtgaagcggccccttcttcacctcgccggatgacatgctggaggagga gtactacgacgagcagctcccggagaagaagcggcgcctcacgccggagc aggtccacctgctggagaggagcttcgaggaggagaacaagctggagccg gagaggaagacggagctggcccgcaagctcgggctgcagccacggcaggt ggccgtctggttccagaaccgccgcgcccggtggaagacaaagacgctgg agcgcgacttcgaccgcctcaaggcgtccttcgacgccctccgcgccgac cacgacgcgctcctccaggacaaccaccggctccggtcacaggtggtaac gttgaccgagaagatgcaagataaggaggcgccggaaggcagcttcgtg cagccgccgacgcctcggagccggagcaggcggcggcggaggcgaaggct tccttggccgacgccgaggagcaggccgcggcagcggaggcgttcgaggt ggtgcagcagcagctgcacgtgaaggacgaggagaggctgagcccggga gcggcggagcgcggtgctggacgcgagggacgcgctgctcgggagcgga tgcggcctcgccggcgtggtggacagcagcgtggactcgtactgcttccc gggggggcgccggcggcgacgagtaccacgagtgcgtggtgggcccgtgg cgggcggcatccagtcggaggaggacgacggcgcgggcagcgacgagggc tgcagctactacccgacgacgccgccgtcttcttcgccgccgcgcaagg gcacggccaccatcgcacggacgacgacgatcagcaggacgacggccagat cagctactggatgtggaactag The TA55969932 cDNA is translated into the following amino acid sequence (SEQ ID NO:16):

mepgrlifntsgsgngqmlfmdcgaggiagaagmfhrgvrpvlggmeegr gvkrpfftspddmleeeyydeqlpekkrrltpeqvhllersfeeenklep erktelarklglqprqvavwfqnrrarwktktlerdfdrlkasfdalrad hdallqdnhrlrsqvvtltekmqdkeapegsfgaaadasepeqaaaeaka sladaeeqaaaaeafevvqqqlhvkdeerlspgsggsavldardallgsg cglagvvdssvdsycfpggaggdeyhecvvgpvaggiqseeddgagsdeg csyypddaavffaaaqghghhrtddddqqddgqisywmwn cDNA sequence of BN47310186 from canola (SEQ ID NO:17):

atggaccacgacaaaacaggatgccaaagcccacctgaaggtcccaagct atgcatcaacaactgcggtttcttcggaagcgctgccacaatgaacatgt gttccaagtgtcacaaggctatcctgtttcaacaggaacaggggctagg tttgcatctgcagtgtctggtggtacatcatcatccagcaacatcttaaa ggaaacctttgctgctaccgcgctggttgatgctgaaaccaaatccgttg agccggtggctgtctctgtacagccatcttctgtccaagttgccgcagag gtagtagctccagaagccgctgcagcaaaactaaaggaaggaccaagccg atgtgctacttgcaataaacgggttggtctgactggattcaaatgtcgct gtggtgaccttctctgcgggacgcaccgttatgcagacatacacaactgc tccttcaattaccatgccgctgcgcaagaagctatagctaaagcaaaccc ggttgtgaaggcagagaagcttgacaaaatctga The BN47310186 cDNA is translated into the following amino acid sequence (SEQ ID NO:18):

mdhdktgcqsppegpklcinncgffgsaatmnmcskchkailfqqeqgar fasavsggtsssssnilketfaatalvdaetksvepvavsvqpssvqvaae vvapeaaaaklkegpsrcatcnkrvgltgfkcrcgdlfcgthryadihnc sfnyhaaaqeaiakanpvvkaekldki cDNA sequence of BN51359456 from canola (SEQ ID NO:19):

atggcggaagagcatcgatgccagacgccggaaggccaccgtctctgtgc taacaactgcggcttcctcggcagctccgccaccatgaatctatgctcca actgctacggcgatctctgccttaagcaacagcaagcttccatgaaatcc accgtcgaatcctctctctccgccgtatctcctccgtcgtcagagatcgg ctctatgcaatccaccgttgaatcctctctctccgacgtatctcctccat caccggagaccattttccatctcctctccaatgatccagcctctcgttcga aacccatcagctgaattggaggtaacggcgacgaagacggtgactccgcc gccgagcagcagcagaaacggccgaatcggtgcacgacgtgtaggaaac gggtcgggttgaccgggttcaagtgccggtgcgggacgacttttttgcggg gctcacaggtacccggaggtccatggatgcaccttcgatttcaaatcggc -continued cggtcgcgaagagatcgccaaggcgaacccactcgtcaaagcggcgaagc ttcagaagatttga The BN51359456 cDNA is translated into the following amino acid sequence (SEQ ID NO:20):

maeehrcqtpeghrlcanncgflgssatmnlcsncygdlclkqqqasmks tvesslsavsppsseigsmqstvesslsdvsppspetisisspmiqplvr npsaelevtatktvtpppeqqqkrpnrcttcrkrvgltgfkcrcgttfcg ahrypevhgctfdfksagreeiakanplvkaaklqki cDNA sequence of HV62552639 from barley (SEQ ID NO:21):

atggcccaggagagttgtgatctcaacaaggacgaggccgagatcctgaa gccatcctcctccacaccttcgcctccttcgccagccacaccaccaccac caaccgctcaaataccagaaccacaacctccacactcaccaccacaacca ccggcagctcaattcttgtccaggccctgcgaggttgttcccatagagac ttccaaaaagaggaaacatgctgatgcggtgtcaatggccattgtggttg agccattgtcgtctgtgctgttcgttaaccgttgcaacgtgtgccgcaag agagttggtttgaccgggttccgttgccggtgtgagaagctcttttgtcc gcgccaccggcattcagaaagccacgactgctcatttgattataaaactg tgggtcgggaggagattgcccgggcaaaccctctgatcagggctgccaag atcattaggatatga The HV62552639 cDNA is translated into the following amino acid sequence (SEQ ID NO:22):

maqescdlnkdeaeilkpsssstpsppspatppppptaqipepqpphsppqp paaqflsrpcevvpietskkrkhadavsmaivveplssvlfvnrcnvcrk rvgltgfrcrceklfcprhrhseshdcsfdyktvgreeiaranpliraak iiri cDNA sequence of ZM61995511 from corn (SEQ ID NO:23):

atggaacacaaggaggcgggctgccagcagccggagggcccaatcctatg catcaataactgcggcttcttcggcagtgctgcgacgatgaacatgtgct ccaagtgccacaaggagatgataacgaagcaggagcaggcccagctggct gcctcccccatcgatagcattgtcaatggcggtgacggcgggaaaggacc tgtaattgctgcatctgtaaatgtggcagttcctcaagttgagcagaaga ctattgttgtgcagcccatgcttgtagctgaaaccagcgaggctgctgct gtaatccccaaggccaaggaaggcccagaccggtgcgcggcctgcaggaa gcgtgttgggctgacgggatttagctgccgatgcgggaacatgtactgtt cggtgcaccgctactccgacaaacatgactgtcagttcgactatcggact gcagcaagggacgcgattgccaaggccaatcctgtggtgagggcggaaa gctcgacaagatctga The ZM61995511 cDNA is translated into the following amino acid sequence (SEQ ID NO:24):

mehkeagcqqpegpilcinncgffgsaatmnmcskchkemitkqeqaqla aspidsivnggdggkgpviaasvnvavpqveqktivvqpmlvaetseaaa vipkakegpdrcaacrkrvgltgfscrcgnmycsvhrysdkhdcqfdyrt aardaiakanpvvraekldki cDNA sequence of LU61567101 from linseed (SEQ ID NO:25):

atggctccttcaccttgcgtccacggctgcacggccaattgccccgctg ccactcttacggacaccccatcttcgggaactcagatctcgccgctggcg gcagcgatacgtccacgtcggtgtttggaaaagtaggatccgtcgtgatt cagtcgcctgcgaagaatcacgcgttcggccaagcttgtggcccggtttt tccctcgagctcctcccctttccgccgcatcaagttcggccccaaagatg gcgaggggaaaggaccgctgaagccgatcgaaagcagccgtcgaagaag cgtccgttctgcttctctcccgacgagacgattgacgcgacggttcctcc gtccaccaaaccgttcggttcgttccgttccgtctgtgtcacggacgccg acgaggccaggttgaaggcgaaccgcgagttcttcgctccggtatcccgc aaacgtggcttcgatccgactgacatgaccttcggtaacgccgccgccgc tgcggctaatgcgagggaggaagcgaagaagtggtgcggcagttgcaaga agcgcgtggggctgttagggttcaagtgcaggtgtacgaagttcttctgt gggaagcatcggtatcctgaggagcatggttgtacgttcgatcatgtggc gttcggaggcggattatcgagaaacagaatcctgttctcgagaccgaca agctggtggacagaatctga The LU61567101 cDNA is translated into the following amino acid sequence (SEQ ID NO:26):

mapspcvhgctancprchsyghpifgnsdlaaggsdtstsvfgkvgsvvi qspaknhafgqacgpvfpssspfrrikfgpkdgegkgplkpiekqpskk rpfcfspdetidatvppstkpfgsfrsvcvtdadearlkanreffapvsr krgfdptdmtfgnaaaaaanareeakkwcgsckkrvgllgfkcrctkffc gkhrypeehgctfdhvafgrriiekqnpvletdklvdri cDNA sequence of LU61893412 from linseed (SEQ ID NO:27):

atggaccatgacgaggcaggctgccaggctccttccgatcatcctattct gtgcgttaacaattgcggcttcttcggaagtgctgccaccatgaacatgt gctcaaagtgccacaaggatacgatgctaaaccaagagcaatccaagctt gctgcttcatcggcagcaagtatcctcaacggatcgtcgatgagcctcgg aagggaactcgttattgctgctaagaccaattcggtagaacccaagacca tctccgtccaaccatcttctgcttcaagtgctgaagagagtatcgaaatg aagctgccaaaagaagggcccagtaggtgcaacacttgcaacaaacgtgt cggtttgaccggattcaaatgtcggtgcgagaacatgttctgcgcaaacc -continued atcgctactcggacaagcacaattgcccctttgattaccgcactgctggc cgtgaagctatctcaaaggccaatcctttggtgaaggcggagaagctcga caaaatctga The LU61893412 cDNA is translated into the following amino acid sequence (SEQ ID NO:28):

mdhdeagcqapsdhpilcvnncgffgsaatmnmcskchkdtmlnqeqskl aassaasilngssmslgrelviaaktnsvepktisvqpssassaeesiem klpkegpsrcntcnkrvgltgfkcrcenmfcanhrysdkhncpfdyrtag reaiskanplvkaekldki cDNA sequence of OS39781852 from rice (SEQ ID NO:29):

atggcgcagcgcgacaagaaggatcaggagccgacggagctcagggcgcc ggagatcacgctgtgcgccaacagctgcggattcccgggcaacccggcca cgcagaacctctgccagaactgcttcttggcggccacggcgtccacctcg tcgccgtcttctttgtcgtcaccggtgctcgacaagcagccgccgaggcc ggcggcgccgctggttgagcctcaggctcctctcccaccgcctgtggagg agatggcctccgcgctcgcgacggcgccggcgccggtcgccaagacgtcg gcggtgaaccggtgctccaggtgccggaagcgtgtcggcctcaccgggtt ccggtgccggtgcggccacctgttctgcggcgagcaccggtactccgacc gccacggctgcagctacgactacaagtcggcggcgagggacgccatcgcc agggacaacccggtggtgcgcgcggccaagatcgttaggttctga The OS39781852 cDNA is translated into the following amino acid sequence (SEQ ID NO:30):

maqrdkkdqeptelrapeitlcanscgfpgnpatqnlcqncflaatasts spsslsspvldkqpprpaaplvepqaplpppveemasalatapapvakts avnrcsrcrkrvgltgfrcrcghlfcgehrysdrhgcsydyksaardaia rdnpvvraakivrf cDNA sequence of OS34701560 from rice (SEQ ID NO:31):

atggccgaagaacaccgatgccaagctcccgaaggtcacagactctgctc caacaactgcggtttctttggtagcccgccaccatgaatctctgttcca aatgctacagagacatccgtttgaaggaagaagaacaagccaaaaccaaa tccacaatcgaaaccgctctttcaggatcttcctccgccaccgtcaccgc aaccgccgtcgttgcctcctccgtggaatcccttcggcgccggttgaat ccctccctcaaccaccggtgctgatttcgccggatatagccgcaccggtt caggcgaaccggtgcggcgcgtgtaggaagcgcgtgggttgacagggtt caagtgcaggtgcggaacaacgttttgtgggagccacaggtaccccgaga aacacgcgtgtggcttcgatttcaaggcggtggggagagaggagatagca cgggcgaatcccgtgatcaaaggcgagaagctacggaggatttaa The OS34701560 cDNA is translated into the following amino acid sequence (SEQ ID NO:32):

maeehrcqapeghrlcsnncgffgspatmnlcskcyrdirlkeeeqaktk stietalsgsssatvtatavvassvespsapveslpqppvlispdiaapv qanrcgacrkrvgltgfkcrcgtffcgshrypekhacgfdfkavgreeia ranpvikgeklrri cDNA sequence of OS36821256 from rice (SEQ ID NO:33):

atggcgcagagggagaagaaggtggaggagccgacggagctgagggcgcc ggagatgacgctctgcgccaacagctgcgggttcccgggcaacccggcga ccaacaacctctgccagaactgcttcttggctgcctcggcgtcttcttct tcttcttccgccgctgcctcgccgtcgacgacgtcgttgccggtgtttcc ggtggtggagaagccgaggcaggccgtacagtcgtcggcggcggcggcgg tggcgctggtggttgagcggccgacggcggggccggtggagtcgtcgtcg aaggcgtcgaggtcgtcgtcggtcaaccgatgccacagctgccggaggcg ggtgggcctgaccgggttccggtgccgctgcggcgagctctactgcggcg cgcaccggtactccgaccgccacgactgcagcttcgactacaagtcggcg gcgagggacgccatcgccagggagaacccgtcgtccgcgccgccaagat cgttaggttctaa The OS36821256 cDNA is translated into the following amino acid sequence (SEQ ID NO:34):

maqrekkveeptelrapemtlcanscgfpgnpatnnlcqncflaasasss sssaaaspsttslpvfpvvekprqavqssaaaavalvverptagpvesss kasrsssvnrchscrrrvgltgfrcrcgelycgahrysdrhdcsfdyksa ardaiarenpvvraakivrf cDNA sequence of GM51659494 from soybean (SEQ ID NO:35):

atggctcagaaaaccgagaagaagaaaccgacttcaaagttccggaaac gattacgctttgcgtcaacaactgcggcgtcaccggaaaccctgccacga ataacatgtgccagaagtgcttcactgcctctaccgccaccacttccggc gccggaggtgccggaatagcttctccggcgaccagatccggcgtctccgc gcgtcctcagaagagatcttttcctgaagagccctcgccggtggcggatc ctccttcttcggaccagacgacgccgtcggaggcgaagcgcgtggtcaac cgctgctccggatgccggcggaaggtcggactcaccggattccggtgccg gtgcggcgagctcttctgcgccgagcaccggtactccgaccgccacgact gcagctatgactacaaagccgccggaagagaagccatcgcgagggagaat ccggtgatcagagctgcgaagatcgtcaaagtctga The GM51659494 cDNA is translated into the following amino acid sequence (SEQ ID NO:36):

maqktekeetdfkvpetitlcvnncgvtgnpatnnmcqkcftastattsg
aggagiaspatrsgvsarpqkrsfpeepspvadppssdqttpseakrvvn
rcsgcrrkvgltgfrcrcgelfcaehrysdrhdcsydykaagreaiaren
pviraakivkv cDNA sequence of GM49780101 from soybean (SEQ ID NO:37):

atggagcctcatgatgagactggatgccaggctcctgaacgcccattct
ttgcattaataattgtggcttctttggaagagcagctaccatgaacatgt
gttccaagtgttacaaggacatgctgttgaagcaggagcaggacaaattt
gcagcatcatccgttgaaaacattgtgaatggcagttccaatggcaatgg
aaagcaggctgtggctactggtgctgttgctgtacaagttgaagctgtgg
aggtcaagattgtctgtgctcagagttctgtggattcgtcctccggtgat
agtttggagatgaaagccaagactggtcccagtagatgtgctacatgccg
gaaacgtgttggtttaactggtttcagctgcaaatgtggcaacctcttct
gtgcaatgcatcgctattctgataaacatgattgcccttttgattatagg
actgttggtcaggatgccatagctaaagccaacccataattaaggcaga
taagctcgacaaaatctag The GM49780101 cDNA is translated into the following amino acid sequence (SEQ ID NO:38):

mephdetgcqaperpilcinncgffgraatmnmcskcykdmllkqeqdkf
aassvenivngssngngkqavatgavavqveavevkivcaqssvdsssgd
slemkaktgpsrcatcrkrvgltgfsckcgnlfcamhrysdkhdcpfdyr
tvgqdaiakanpiikadkldki cDNA sequence of GM59637305 from soybean (SEQ ID NO:39):

atggaccatgacaagactgggtgccaagctcctcctgaaggtcctatatt
gtgcatcaacaactgtgggttttttggaagtgcagctaccatgaacatgt
gttctaaatgccacaaagacatattgctgaaacaggagcaggccaagctt
gcagcatcatccattgggaatattatgaatgggtcatcaagcagcactga
aaaggaacctgttgttgctgctgctgctaatattgatatcccagttattc
cagtagagcctaaaactgtctctgtgcaacctttatttggttcaggtcca
gaggggagtgttgaggcaaagccgaaggatggaccaaaacgttcagcag
ctgcaacaagcgagttggtttgacagggtttaattgtcgatgtggtgacc
ttttttgtgctgtacatcgctactcgacaagcataattgcccatttgat
taccgcactgccgctcaagatgctatagctaaagcaaacccagttgtcaa
ggctgaaaagcttgataagatctaa The GM59637305 cDNA is translated into the following amino acid sequence (SEQ ID NO:40):

mdhdktgcqappegpilcinncgffgsaatmnmcskchkdillkqeqakl
aassignimngssssstekepvvaaaanidipvipvepktvsvqplfgsgp
egsveakpkdgpkrcsscnkrvgltgfncrcgdlflcctslldkhncpfd
yrtaaqdaiakanpvvkaekldki cDNA sequence of TA55974113 from wheat (SEQ ID NO:41):

atggcgcagcgggatcacaagcaggaggagcccacggagctgcgggcgcc
ggagatcacgctctgcgccaacagctgcggcttcccgggcaacccggcca
cgcagaacctctgccagaactgcttcttggccggcccggcgtccacgtcg
ccgtcttcctcctcctcctcctcctcttctctgccgggcgtgtccgcgcc
gaccccgtcatcgacaggccgaggccggcgccgttggaggcggagctgg
cacgccccgccgtcgaccttgctccggcgacggaggcgaagccggcgagg
acgtcggtgaaccggtgctccagctgccggaagcgcgtggggctgacggg
gttccggtgccggtgcggcgacatgttctgcggcgagcaccggtactcgg
accggcacgggtgcagctacgactacaaggccgccgcagggacgccatc
gccagggacaacccccgtcgtgcgcgccgccaagatcgtcaggttctga The TA55974113 cDNA is translated into the following amino acid sequence (SEQ ID NO:42):

maqrdhkqeeptelrapeitlcanscgfpgnpatqnlcqncflagpasts
pssssssssslpgvsaptpvidrprpapleaelarpavdlapateakpar
tsvnrcsscrkrvgltgfrcrcgdmfcgehrysdrhgcsydykaaardai
ardnpvvraakivrf The EST65 amino acid sequence (SEQ ID NO:43):

mvaesvlvcrssvvgaglqsfvgegakresagpgrsvflgaqvqkmgagm
sarsdvrpaavpkasgdvseqtdyktfsdeewkkrlsqqqfyvarkkgte
rpftgeywntktagtylcvccktplfssktkfdsgtgwpsyydtigdnvk
shmdwsipfmprtevvcavcdahlghvfddgprptgkrycinsaaidlka
ekqeern The EST12 amino acid sequence (SEQ ID NO:44):

mvvpslpafggqnamlrrnidnntdtlisllqgscsprvsmqqvprsses
lenmmgacgqklpyfssfdgpsveeqedvdegidefahhvekkrrlsleq
vrslernfevenklepеrkmqlakelglrprqvavwfqnrrarwktkqle
hdyetlkkaydrlkadfeavtldtnalkaevsrlkgisnddvkpaefvqg
kcdttshpaspaqsersdivssrnrttptihvdpvapeeagahltmssds
nssevmdadsprtshtsasrstlstsvvqpdeglgvaqyphfspenfvgp
nmpeicadqslasqvkleeihsfnpdqtflllpnwwdwa The EST307 amino acid sequence (SEQ ID NO:45):

matervsqettsqapegpvmcknlcgffgsqatmglcskcyretvmqakm
talaeqatqaaqatsataaavqppapvhetkltcevertmivphqsssyq
qdlvtpaaaapqavkssiaapsrpepnrcgscrkrvgltgfkcrcgnlyc
alhrysdkhtctydykaagqeaiakanplvvaekvvkf

The invention claimed is:

1. A transgenic plant transformed with an expression cassette comprising an isolated polynucleotide encoding a polypeptide comprising SEQ ID NO:14.

2. A method of producing a transgenic plant comprising the steps of:
(a) introducing into a plant cell an expression vector comprising a polynucleotide [selected from the group consisting of: (i) a polynucleotide comprising SEQ ID NO:13, and (ii) a polynucleotide] encoding a polypeptide comprising SEQ ID NO:14; and
(b) generating from the plant cell a transgenic plant that expresses the polynucleotide, wherein expression of the polynucleotide in the transgenic plant results in increased growth or yield of the plant under normal or water-limited conditions or increased tolerance to environmental stress as compared to a wild type variety of the plant.

* * * * *

```
                         SEQUENCE LISTING

<160> NUMBER OF SEQ ID NOS: 45

<210> SEQ ID NO 1
<211> LENGTH: 615
<212> TYPE: DNA
<213> ORGANISM: Brassica napus
<220> FEATURE:
<221> NAME/KEY: CDS
<222> LOCATION: (1)..(615)
<223> OTHER INFORMATION: methionine sulfoxide reductase family protein
      (BN51364980)

<400> SEQUENCE: 1 atg gct tct tct agt tgt ttc acc att cag tca cgt ttc gtc tca gcg      48
Met Ala Ser Ser Ser Cys Phe Thr Ile Gln Ser Arg Phe Val Ser Ala
1               5                   10                  15 aga aca aag ctc gat tca atc tcc aaa ccg agt ctc tcc gga ttc gct      96
Arg Thr Lys Leu Asp Ser Ile Ser Lys Pro Ser Leu Ser Gly Phe Ala
            20                  25                  30 tgt cgt tct ctt aca aaa ccc aga aac ttg aat ctc tct gtt ctt ctt     144
Cys Arg Ser Leu Thr Lys Pro Arg Asn Leu Asn Leu Ser Val Leu Leu
        35                  40                  45 cgg tgt tcc atg ggt tcc ttt aac tct tct cag aaa tca gac aac gtc     192
Arg Cys Ser Met Gly Ser Phe Asn Ser Ser Gln Lys Ser Asp Asn Val
    50                  55                  60 caa gaa gct gca aag agt gac ttt gct tca ata agt gaa ggt gag tgg     240
Gln Glu Ala Ala Lys Ser Asp Phe Ala Ser Ile Ser Glu Gly Glu Trp
65                  70                  75                  80 aag aaa cgg cta aca cca gaa cag tat tac atc acc aga cag aag gga     288
Lys Lys Arg Leu Thr Pro Glu Gln Tyr Tyr Ile Thr Arg Gln Lys Gly
                85                  90                  95 aca gag aga gct ttc act ggt gag tat tgg aat aca aag acc cca gga     336
Thr Glu Arg Ala Phe Thr Gly Glu Tyr Trp Asn Thr Lys Thr Pro Gly
            100                 105                 110 gta tac aaa tgt atc tgt tgc gac acg cca ctg ttt gac tca tca aca     384
Val Tyr Lys Cys Ile Cys Cys Asp Thr Pro Leu Phe Asp Ser Ser Thr
        115                 120                 125 aag ctt gat agt gga acc ggg tgg cca tcg tat tac caa cct att gga     432
Lys Leu Asp Ser Gly Thr Gly Trp Pro Ser Tyr Tyr Gln Pro Ile Gly
    130                 135                 140 aac aat gtg aag tca aag ctg gac ctc tct atc atc ttc atg cct aga     480
Asn Asn Val Lys Ser Lys Leu Asp Leu Ser Ile Ile Phe Met Pro Arg
145                 150                 155                 160 caa gaa gtt atc tgt gct gtt tgt aac gcc cat ctt ggt cat gtc ttc     528
Gln Glu Val Ile Cys Ala Val Cys Asn Ala His Leu Gly His Val Phe
                165                 170                 175 gat gac ggt cca cga cca acc gga aaa cga tat tgc ctc aac agt gct     576
Asp Asp Gly Pro Arg Pro Thr Gly Lys Arg Tyr Cys Leu Asn Ser Ala
            180                 185                 190 gct ctg aaa ctt gag tca ttg gag aga aca aga gaa tga                 615
Ala Leu Lys Leu Glu Ser Leu Glu Arg Thr Arg Glu
        195                 200

<210> SEQ ID NO 2
```

<211> LENGTH: 204
<212> TYPE: PRT
<213> ORGANISM: Brassica napus

<400> SEQUENCE: 2

| Met | Ala | Ser | Ser | Ser | Cys | Phe | Thr | Ile | Gln | Ser | Arg | Phe | Val | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Thr | Lys | Leu | Asp | Ser | Ile | Ser | Lys | Pro | Ser | Leu | Ser | Gly | Phe | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Cys | Arg | Ser | Leu | Thr | Lys | Pro | Arg | Asn | Leu | Asn | Leu | Ser | Val | Leu | Leu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Cys | Ser | Met | Gly | Ser | Phe | Asn | Ser | Ser | Gln | Lys | Ser | Asp | Asn | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Glu | Ala | Ala | Lys | Ser | Asp | Phe | Ala | Ser | Ile | Ser | Glu | Gly | Glu | Trp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Lys | Arg | Leu | Thr | Pro | Glu | Gln | Tyr | Tyr | Ile | Thr | Arg | Gln | Lys | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Glu | Arg | Ala | Phe | Thr | Gly | Glu | Tyr | Trp | Asn | Thr | Lys | Thr | Pro | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Tyr | Lys | Cys | Ile | Cys | Cys | Asp | Thr | Pro | Leu | Phe | Asp | Ser | Ser | Thr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Lys | Leu | Asp | Ser | Gly | Thr | Gly | Trp | Pro | Ser | Tyr | Tyr | Gln | Pro | Ile | Gly |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Asn | Asn | Val | Lys | Ser | Lys | Leu | Asp | Leu | Ser | Ile | Ile | Phe | Met | Pro | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gln | Glu | Val | Ile | Cys | Ala | Val | Cys | Asn | Ala | His | Leu | Gly | His | Val | Phe |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Asp | Gly | Pro | Arg | Pro | Thr | Gly | Lys | Arg | Tyr | Cys | Leu | Asn | Ser | Ala |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ala | Leu | Lys | Leu | Glu | Ser | Leu | Glu | Arg | Thr | Arg | Glu |
|-----|-----|-----|-----|-----|-----|-----|-----|-----|-----|-----|-----|
|     |     | 195 |     |     |     |     | 200 |     |     |     |     |

<210> SEQ ID NO 3
<211> LENGTH: 615
<212> TYPE: DNA
<213> ORGANISM: Oryza sativa
<220> FEATURE:
<221> NAME/KEY: CDS
<222> LOCATION: (1)..(615)
<223> OTHER INFORMATION: methionine sulfoxide reductase family protein
      (OS34096188)

<400> SEQUENCE: 3

| atg | ggc | ttc | aat | att | ctg | aga | acc | act | tcc | atc | tcc | act | cct | atc | tct | 48 |
|-----|-----|-----|-----|-----|-----|-----|-----|-----|-----|-----|-----|-----|-----|-----|-----|-----|
| Met | Gly | Phe | Asn | Ile | Leu | Arg | Thr | Thr | Ser | Ile | Ser | Thr | Pro | Ile | Ser |   |
| 1   |     |     |     | 5   |     |     |     |     | 10  |     |     |     |     | 15  |     |   |

| tcc | tcc | aaa | tcc | aaa | ccc | att | ttc | tca | act | ctt | ctt | cgt | tct | tct | cct | 96 |
|-----|-----|-----|-----|-----|-----|-----|-----|-----|-----|-----|-----|-----|-----|-----|-----|-----|
| Ser | Ser | Lys | Ser | Lys | Pro | Ile | Phe | Ser | Thr | Leu | Leu | Arg | Ser | Ser | Pro |   |
|     |     |     | 20  |     |     |     |     | 25  |     |     |     |     | 30  |     |     |   |

| tcc | acc | att | ttc | ccc | cca | aag | tcc | gtt | act | ccc | acc | act | ctt | ttc | gtt | 144 |
|-----|-----|-----|-----|-----|-----|-----|-----|-----|-----|-----|-----|-----|-----|-----|-----|-----|
| Ser | Thr | Ile | Phe | Pro | Pro | Lys | Ser | Val | Thr | Pro | Thr | Thr | Leu | Phe | Val |   |
|     |     | 35  |     |     |     |     | 40  |     |     |     |     | 45  |     |     |     |   |

| tct | gcc | acc | ccc | ttc | ttc | act | ctc | cat | ccc | aag | ctt | ggt | ttt | cgt | ggt | 192 |
|-----|-----|-----|-----|-----|-----|-----|-----|-----|-----|-----|-----|-----|-----|-----|-----|-----|
| Ser | Ala | Thr | Pro | Phe | Phe | Thr | Leu | His | Pro | Lys | Leu | Gly | Phe | Arg | Gly |   |
|     | 50  |     |     |     |     | 55  |     |     |     |     | 60  |     |     |     |     |   |

| ggg | att | gtg | gcc | atg | gcc | gca | cct | ggc | tct | ctc | cgc | aaa | tcc | gag | gaa | 240 |
|-----|-----|-----|-----|-----|-----|-----|-----|-----|-----|-----|-----|-----|-----|-----|-----|-----|
| Gly | Ile | Val | Ala | Met | Ala | Ala | Pro | Gly | Ser | Leu | Arg | Lys | Ser | Glu | Glu |   |
| 65  |     |     |     |     | 70  |     |     |     |     | 75  |     |     |     |     | 80  |   |

| gag | tgg | cgc | gca | att | ctc | tcc | cct | gaa | cag | ttt | cgg | atc | ctc | agg | caa | 288 |
|-----|-----|-----|-----|-----|-----|-----|-----|-----|-----|-----|-----|-----|-----|-----|-----|-----|
| Glu | Trp | Arg | Ala | Ile | Leu | Ser | Pro | Glu | Gln | Phe | Arg | Ile | Leu | Arg | Gln |   |

```
aag ggc acc gag ttc cct gga aca gga gag tat gac aag ttc tat gaa    336
Lys Gly Thr Glu Phe Pro Gly Thr Gly Glu Tyr Asp Lys Phe Tyr Glu
            100                 105                 110 gag gga gtt tac aac tgt gct ggt tgt ggg act cca ctc tac agg tcc    384
Glu Gly Val Tyr Asn Cys Ala Gly Cys Gly Thr Pro Leu Tyr Arg Ser
            115                 120                 125 ata aca aaa ttc aat tct ggt tgt ggc tgg cca gcc ttc tat gag ggg    432
Ile Thr Lys Phe Asn Ser Gly Cys Gly Trp Pro Ala Phe Tyr Glu Gly
        130                 135                 140 att ccc gga gcc ata aat cgc aat ccg gat cct gat ggg atg agg aca    480
Ile Pro Gly Ala Ile Asn Arg Asn Pro Asp Pro Asp Gly Met Arg Thr
145                 150                 155                 160 gaa ata acg tgt gct gct tgt ggg gga cat cta ggt cac gtc ttt aaa    528
Glu Ile Thr Cys Ala Ala Cys Gly Gly His Leu Gly His Val Phe Lys
                165                 170                 175 gga gaa gga ttt cca aca ccc act aac gaa cgc cat tgt gtc aat agc    576
Gly Glu Gly Phe Pro Thr Pro Thr Asn Glu Arg His Cys Val Asn Ser
            180                 185                 190 att tcg ctg aaa ttt gcg cca gcc aat tct tat tct taa                615
Ile Ser Leu Lys Phe Ala Pro Ala Asn Ser Tyr Ser
        195                 200

<210> SEQ ID NO 4
<211> LENGTH: 204
<212> TYPE: PRT
<213> ORGANISM: Oryza sativa

<400> SEQUENCE: 4

Met Gly Phe Asn Ile Leu Arg Thr Thr Ser Ile Ser Thr Pro Ile Ser
1               5                   10                  15

Ser Ser Lys Ser Lys Pro Ile Phe Ser Thr Leu Leu Arg Ser Ser Pro
            20                  25                  30

Ser Thr Ile Phe Pro Pro Lys Ser Val Thr Pro Thr Thr Leu Phe Val
        35                  40                  45

Ser Ala Thr Pro Phe Phe Thr Leu His Pro Lys Leu Gly Phe Arg Gly
    50                  55                  60

Gly Ile Val Ala Met Ala Ala Pro Gly Ser Leu Arg Lys Ser Glu Glu
65                  70                  75                  80

Glu Trp Arg Ala Ile Leu Ser Pro Glu Gln Phe Arg Ile Leu Arg Gln
                85                  90                  95

Lys Gly Thr Glu Phe Pro Gly Thr Gly Glu Tyr Asp Lys Phe Tyr Glu
            100                 105                 110

Glu Gly Val Tyr Asn Cys Ala Gly Cys Gly Thr Pro Leu Tyr Arg Ser
        115                 120                 125

Ile Thr Lys Phe Asn Ser Gly Cys Gly Trp Pro Ala Phe Tyr Glu Gly
    130                 135                 140

Ile Pro Gly Ala Ile Asn Arg Asn Pro Asp Pro Asp Gly Met Arg Thr
145                 150                 155                 160

Glu Ile Thr Cys Ala Ala Cys Gly Gly His Leu Gly His Val Phe Lys
                165                 170                 175

Gly Glu Gly Phe Pro Thr Pro Thr Asn Glu Arg His Cys Val Asn Ser
            180                 185                 190

Ile Ser Leu Lys Phe Ala Pro Ala Asn Ser Tyr Ser
        195                 200

<210> SEQ ID NO 5
<211> LENGTH: 645
```

```
<212> TYPE: DNA
<213> ORGANISM: Oryza sativa
<220> FEATURE:
<221> NAME/KEY: CDS
<222> LOCATION: (1)..(645)
<223> OTHER INFORMATION: methionine sulfoxide reductase family protein
      (OS32583643)

<400> SEQUENCE: 5 atg gcc atg cgg caa tac gcg gct gct acc gct gcc tcc tcc agt ttc        48
Met Ala Met Arg Gln Tyr Ala Ala Ala Thr Ala Ala Ser Ser Ser Phe
1               5                   10                  15 aga gca cgt cca cgg gcg cgc ccc tcc tgc ctc cca gcc gcc gcc ctg        96
Arg Ala Arg Pro Arg Ala Arg Pro Ser Cys Leu Pro Ala Ala Ala Leu
                20                  25                  30 ccc ttg gcg cct tgc tgt ggt gtg gcg tgg agc cgt gct agc tac agg       144
Pro Leu Ala Pro Cys Cys Gly Val Ala Trp Ser Arg Ala Ser Tyr Arg
            35                  40                  45 cga gcc tcc gtt cgt gcc atg ggt gcc gct tca tcg tct tcg tcg tcg       192
Arg Ala Ser Val Arg Ala Met Gly Ala Ala Ser Ser Ser Ser Ser Ser
        50                  55                  60 tcg tcg tcg tct ccg tcg ccg cag ggt caa gcc caa gcc caa gcc caa       240
Ser Ser Ser Ser Pro Ser Pro Gln Gly Gln Ala Gln Ala Gln Ala Gln
65                  70                  75                  80 ggt aaa ccg aac tac agt aca tct ctg act gat gag gag tgg agg aag       288
Gly Lys Pro Asn Tyr Ser Thr Ser Leu Thr Asp Glu Glu Trp Arg Lys
                85                  90                  95 cgc ctg aca aaa gat cag tat tac att act cgg cag aag ggc aca gaa       336
Arg Leu Thr Lys Asp Gln Tyr Tyr Ile Thr Arg Gln Lys Gly Thr Glu
                100                 105                 110 aga gca ttt act ggg gaa tac tgg aac acc aaa acc ccg ggc atc tac       384
Arg Ala Phe Thr Gly Glu Tyr Trp Asn Thr Lys Thr Pro Gly Ile Tyr
            115                 120                 125 cat tgt gtc tgc tgt gac acc cct ctt ttt gag tca tcg acc aaa ttt       432
His Cys Val Cys Cys Asp Thr Pro Leu Phe Glu Ser Ser Thr Lys Phe
        130                 135                 140 gat agt ggt act ggg tgg ccg tca tat tat caa ccc att gga gat aat       480
Asp Ser Gly Thr Gly Trp Pro Ser Tyr Tyr Gln Pro Ile Gly Asp Asn
145                 150                 155                 160 gta aag tgc aag ctt gat atg tcc ata ata ttc atg cct cgg act gag       528
Val Lys Cys Lys Leu Asp Met Ser Ile Ile Phe Met Pro Arg Thr Glu
                165                 170                 175 gtg ctg tgt gct gtc tgt gac gct cat ctg ggg cac gtg ttt gat gat       576
Val Leu Cys Ala Val Cys Asp Ala His Leu Gly His Val Phe Asp Asp
                180                 185                 190 ggg cca cga cca aca ggg aaa aga tac tgt atc aat agc gca tct ctc       624
Gly Pro Arg Pro Thr Gly Lys Arg Tyr Cys Ile Asn Ser Ala Ser Leu
            195                 200                 205 aag ctg aag aag acc cag tag                                           645
Lys Leu Lys Lys Thr Gln
            210

<210> SEQ ID NO 6
<211> LENGTH: 214
<212> TYPE: PRT
<213> ORGANISM: Oryza sativa

<400> SEQUENCE: 6

Met Ala Met Arg Gln Tyr Ala Ala Ala Thr Ala Ala Ser Ser Ser Phe
1               5                   10                  15

Arg Ala Arg Pro Arg Ala Arg Pro Ser Cys Leu Pro Ala Ala Ala Leu
                20                  25                  30
```

```
Pro Leu Ala Pro Cys Cys Gly Val Ala Trp Ser Arg Ala Ser Tyr Arg
        35                  40                  45

Arg Ala Ser Val Arg Ala Met Gly Ala Ala Ser Ser Ser Ser Ser Ser
 50                  55                  60

Ser Ser Ser Ser Pro Ser Pro Gln Gly Gln Ala Gln Ala Gln Ala Gln
 65                  70                  75                  80

Gly Lys Pro Asn Tyr Ser Thr Ser Leu Thr Asp Glu Glu Trp Arg Lys
                 85                  90                  95

Arg Leu Thr Lys Asp Gln Tyr Tyr Ile Thr Arg Gln Lys Gly Thr Glu
            100                 105                 110

Arg Ala Phe Thr Gly Glu Tyr Trp Asn Thr Lys Thr Pro Gly Ile Tyr
        115                 120                 125

His Cys Val Cys Cys Asp Thr Pro Leu Phe Glu Ser Ser Thr Lys Phe
130                 135                 140

Asp Ser Gly Thr Gly Trp Pro Ser Tyr Tyr Gln Pro Ile Gly Asp Asn
145                 150                 155                 160

Val Lys Cys Lys Leu Asp Met Ser Ile Ile Phe Met Pro Arg Thr Glu
                165                 170                 175

Val Leu Cys Ala Val Cys Asp Ala His Leu Gly His Val Phe Asp Asp
            180                 185                 190

Gly Pro Arg Pro Thr Gly Lys Arg Tyr Cys Ile Asn Ser Ala Ser Leu
        195                 200                 205

Lys Leu Lys Lys Thr Gln
        210
```

<210> SEQ ID NO 7
<211> LENGTH: 609
<212> TYPE: DNA
<213> ORGANISM: Glycine max
<220> FEATURE:
<221> NAME/KEY: CDS
<222> LOCATION: (1)..(609)
<223> OTHER INFORMATION: methionine sulfoxide reductase family protein (GM53626178)

<400> SEQUENCE: 7

```
atg gga ttg agt att ctg aga agc act tcc att tcc act cct atc tct      48
Met Gly Leu Ser Ile Leu Arg Ser Thr Ser Ile Ser Thr Pro Ile Ser
 1               5                  10                  15 tcc tcc aaa tcc aaa ccc att ttc tca act ctt gtt cgt tca tct ttc      96
Ser Ser Lys Ser Lys Pro Ile Phe Ser Thr Leu Val Arg Ser Ser Phe
                20                  25                  30 gcc tcc att tcc ccc aca aag tgt gtt act ccc acc act ctt ttc gtt     144
Ala Ser Ile Ser Pro Thr Lys Cys Val Thr Pro Thr Thr Leu Phe Val
            35                  40                  45 tct gcc acc ccc ttc ttc acc gcc tca ccc aag cgc ggc ttt cgt ggt     192
Ser Ala Thr Pro Phe Phe Thr Ala Ser Pro Lys Arg Gly Phe Arg Gly
 50                  55                  60 ggg att gtg gcc atg gcc gcc gct ggc tcg ctc cgc aaa tca gag gaa     240
Gly Ile Val Ala Met Ala Ala Ala Gly Ser Leu Arg Lys Ser Glu Glu
 65                  70                  75                  80 gag tgg cgc gca gtt ctc tcc cct gaa cag ttt cgt att ctc agg caa     288
Glu Trp Arg Ala Val Leu Ser Pro Glu Gln Phe Arg Ile Leu Arg Gln
                 85                  90                  95 aag ggc acc gag ttc cct gga aca gga gag tat gac aag ttc ttt gat     336
Lys Gly Thr Glu Phe Pro Gly Thr Gly Glu Tyr Asp Lys Phe Phe Asp
            100                 105                 110 gag gga gtt tac aac tgt gct ggt tgt ggg aca cct ctc tac agg tcc     384
Glu Gly Val Tyr Asn Cys Ala Gly Cys Gly Thr Pro Leu Tyr Arg Ser
        115                 120                 125
```

```
tta aca aaa ttc aat tct ggt tgt ggc tgg cca gcc ttc tat gag ggg      432
Leu Thr Lys Phe Asn Ser Gly Cys Gly Trp Pro Ala Phe Tyr Glu Gly
        130                 135                 140 att cct gga gcc ata aat cgc aat ccg gac cct gat ggg atg agg aca      480
Ile Pro Gly Ala Ile Asn Arg Asn Pro Asp Pro Asp Gly Met Arg Thr
145                 150                 155                 160 gaa ata acg tgt gct gct tgt ggg gga cat cta ggt cac gtc ttt aaa      528
Glu Ile Thr Cys Ala Ala Cys Gly Gly His Leu Gly His Val Phe Lys
                165                 170                 175 gga gaa gga ttt cca acg ccc act aac gaa cgc cat tgt gtc aat agc      576
Gly Glu Gly Phe Pro Thr Pro Thr Asn Glu Arg His Cys Val Asn Ser
            180                 185                 190 att tca ctg aaa ttt gcg cca gcc aat tct taa                          609
Ile Ser Leu Lys Phe Ala Pro Ala Asn Ser
        195                 200
```

<210> SEQ ID NO 8
<211> LENGTH: 202
<212> TYPE: PRT
<213> ORGANISM: Glycine max

<400> SEQUENCE: 8

```
Met Gly Leu Ser Ile Leu Arg Ser Thr Ser Ile Ser Thr Pro Ile Ser
1               5                   10                  15

Ser Ser Lys Ser Lys Pro Ile Phe Ser Thr Leu Val Arg Ser Ser Phe
            20                  25                  30

Ala Ser Ile Ser Pro Thr Lys Cys Val Thr Pro Thr Leu Phe Val
        35                  40                  45

Ser Ala Thr Pro Phe Phe Thr Ala Ser Pro Lys Arg Gly Phe Arg Gly
    50                  55                  60

Gly Ile Val Ala Met Ala Ala Gly Ser Leu Arg Lys Ser Glu Glu
65                  70                  75                  80

Glu Trp Arg Ala Val Leu Ser Pro Glu Gln Phe Arg Ile Leu Arg Gln
                85                  90                  95

Lys Gly Thr Glu Phe Pro Gly Thr Gly Glu Tyr Asp Lys Phe Asp
            100                 105                 110

Glu Gly Val Tyr Asn Cys Ala Gly Cys Gly Thr Pro Leu Tyr Arg Ser
        115                 120                 125

Leu Thr Lys Phe Asn Ser Gly Cys Gly Trp Pro Ala Phe Tyr Glu Gly
    130                 135                 140

Ile Pro Gly Ala Ile Asn Arg Asn Pro Asp Pro Asp Gly Met Arg Thr
145                 150                 155                 160

Glu Ile Thr Cys Ala Ala Cys Gly Gly His Leu Gly His Val Phe Lys
                165                 170                 175

Gly Glu Gly Phe Pro Thr Pro Thr Asn Glu Arg His Cys Val Asn Ser
            180                 185                 190

Ile Ser Leu Lys Phe Ala Pro Ala Asn Ser
        195                 200
```

<210> SEQ ID NO 9
<211> LENGTH: 621
<212> TYPE: DNA
<213> ORGANISM: Triticum aestivum
<220> FEATURE:
<221> NAME/KEY: CDS
<222> LOCATION: (1)..(621)
<223> OTHER INFORMATION: methionine sulfoxide reductase family protein
      (TA6540264)

<400> SEQUENCE: 9

```
atg gcg tcg ccc cac gcc cac ccg gcc acg cgg ccc ctc tca tcg ctc     48
Met Ala Ser Pro His Ala His Pro Ala Thr Arg Pro Leu Ser Ser Leu
1               5                   10                  15 ccg tcc ctc ctc ctc gcc cgc tcc tcc tcc gcc gcc acc gcc gcc gcg     96
Pro Ser Leu Leu Leu Ala Arg Ser Ser Ser Ala Ala Thr Ala Ala Ala
            20                  25                  30 tcg tcc gcc cgc ccc gcc tcc ctc tcc ctc tcg tgc tcg cgg tcg cgg    144
Ser Ser Ala Arg Pro Ala Ser Leu Ser Leu Ser Cys Ser Arg Ser Arg
        35                  40                  45 gcg cgg gcc tac tgc cca gcc gga cga cgg ttg ccg ggc gcc gtg gtg    192
Ala Arg Ala Tyr Cys Pro Ala Gly Arg Arg Leu Pro Gly Ala Val Val
    50                  55                  60 gct atg tcg tcg gcg gcg ccc acg ccg ggg ccc gtg cag aag tcg gag    240
Ala Met Ser Ser Ala Ala Pro Thr Pro Gly Pro Val Gln Lys Ser Glu
65              70                  75                  80 gag gag tgg gag gcc gtc ctc acg ccg gag cag ttc cgc atc ctc cgc    288
Glu Glu Trp Glu Ala Val Leu Thr Pro Glu Gln Phe Arg Ile Leu Arg
                85                  90                  95 cgc aag ggc acc gag tat cct gga aca ggt gaa tat gac aag ttc ttc    336
Arg Lys Gly Thr Glu Tyr Pro Gly Thr Gly Glu Tyr Asp Lys Phe Phe
            100                 105                 110 agt gag ggt att tac gga tgt gct ggc tgt gga acc ccc ttg tac aaa    384
Ser Glu Gly Ile Tyr Gly Cys Ala Gly Cys Gly Thr Pro Leu Tyr Lys
        115                 120                 125 tca tct acg aag ttc aac tca ggg tgt ggt tgg cca gca ttc tat gaa    432
Ser Ser Thr Lys Phe Asn Ser Gly Cys Gly Trp Pro Ala Phe Tyr Glu
    130                 135                 140 gga ttt cct gga gcc ata aaa cgg acg gcg gat cct gat ggg agg cga    480
Gly Phe Pro Gly Ala Ile Lys Arg Thr Ala Asp Pro Asp Gly Arg Arg
145                 150                 155                 160 att gag atc aca tgt gct gct tgt gaa gga cat ctg ggg cat gtg ttc    528
Ile Glu Ile Thr Cys Ala Ala Cys Glu Gly His Leu Gly His Val Phe
                165                 170                 175 aaa ggg gag ggg ttc aac acg ccg act gat gag cga cac tgc gtc aac    576
Lys Gly Glu Gly Phe Asn Thr Pro Thr Asp Glu Arg His Cys Val Asn
            180                 185                 190 agt atc tca ctc aag ttc gtt ccg gcc tct gaa gag gct agt tga        621
Ser Ile Ser Leu Lys Phe Val Pro Ala Ser Glu Glu Ala Ser
        195                 200                 205
```

<210> SEQ ID NO 10
<211> LENGTH: 206
<212> TYPE: PRT
<213> ORGANISM: Triticum aestivum

<400> SEQUENCE: 10

```
Met Ala Ser Pro His Ala His Pro Ala Thr Arg Pro Leu Ser Ser Leu
1               5                   10                  15

Pro Ser Leu Leu Leu Ala Arg Ser Ser Ser Ala Ala Thr Ala Ala Ala
            20                  25                  30

Ser Ser Ala Arg Pro Ala Ser Leu Ser Leu Ser Cys Ser Arg Ser Arg
        35                  40                  45

Ala Arg Ala Tyr Cys Pro Ala Gly Arg Arg Leu Pro Gly Ala Val Val
    50                  55                  60

Ala Met Ser Ser Ala Ala Pro Thr Pro Gly Pro Val Gln Lys Ser Glu
65              70                  75                  80

Glu Glu Trp Glu Ala Val Leu Thr Pro Glu Gln Phe Arg Ile Leu Arg
                85                  90                  95

Arg Lys Gly Thr Glu Tyr Pro Gly Thr Gly Glu Tyr Asp Lys Phe Phe
```

```
                       100                 105                 110
        Ser Glu Gly Ile Tyr Gly Cys Ala Gly Cys Gly Thr Pro Leu Tyr Lys
                    115                 120                 125

Ser Ser Thr Lys Phe Asn Ser Gly Cys Gly Trp Pro Ala Phe Tyr Glu
                    130                 135                 140

Gly Phe Pro Gly Ala Ile Lys Arg Thr Ala Asp Pro Asp Gly Arg Arg
        145                 150                 155                 160

Ile Glu Ile Thr Cys Ala Ala Cys Glu Gly His Leu Gly His Val Phe
                        165                 170                 175

Lys Gly Glu Gly Phe Asn Thr Pro Thr Asp Glu Arg His Cys Val Asn
                    180                 185                 190

Ser Ile Ser Leu Lys Phe Val Pro Ala Ser Glu Glu Ala Ser
                    195                 200                 205

<210> SEQ ID NO 11
<211> LENGTH: 933
<212> TYPE: DNA
<213> ORGANISM: Brassica napus
<220> FEATURE:
<221> NAME/KEY: CDS
<222> LOCATION: (1)..(933)
<223> OTHER INFORMATION: homeodomain leucine zipper protein (BN45206322)

<400> SEQUENCE: 11 atg atg aag aga tta agc agt tca gat tca gtg ggt ggt ctc atc tct        48
Met Met Lys Arg Leu Ser Ser Ser Asp Ser Val Gly Gly Leu Ile Ser
1               5                   10                  15 tta tgt ccc act act tcc aca gat cag ccg aat cca aga aga tgc ggg        96
Leu Cys Pro Thr Thr Ser Thr Asp Gln Pro Asn Pro Arg Arg Cys Gly
            20                  25                  30 aga gaa ttt cag tcg atg ctc gaa ggt tac gag gag gaa gaa gaa gaa       144
Arg Glu Phe Gln Ser Met Leu Glu Gly Tyr Glu Glu Glu Glu Glu Glu
        35                  40                  45 gcc ata acc gag gaa aga gga caa acc ggt tta gcc gag aag aag aga       192
Ala Ile Thr Glu Glu Arg Gly Gln Thr Gly Leu Ala Glu Lys Lys Arg
    50                  55                  60 cgg tta aac att aac caa gtt aaa gcc ttg gag aaa aat ttc gag tta       240
Arg Leu Asn Ile Asn Gln Val Lys Ala Leu Glu Lys Asn Phe Glu Leu
65                  70                  75                  80 gag aac aag ctt gag cct gag agg aaa gtg aag tta gct caa gaa ctt       288
Glu Asn Lys Leu Glu Pro Glu Arg Lys Val Lys Leu Ala Gln Glu Leu
                85                  90                  95 ggt ctc caa cct cgt caa gta gct gtt tgg ttt cag aac cgc cgt gcg       336
Gly Leu Gln Pro Arg Gln Val Ala Val Trp Phe Gln Asn Arg Arg Ala
            100                 105                 110 cgg tgg aag aca aaa cag ctt gag aaa gat tac ggt gtt ctc aaa acg       384
Arg Trp Lys Thr Lys Gln Leu Glu Lys Asp Tyr Gly Val Leu Lys Thr
        115                 120                 125 caa tac gat tct ctc cgc cat aac ttt gat tcc ctc cgc cgt gaa aat       432
Gln Tyr Asp Ser Leu Arg His Asn Phe Asp Ser Leu Arg Arg Glu Asn
    130                 135                 140 gaa tct ctt ctt caa gag atc ggt aaa cta aaa gct aag ctt aac gga       480
Glu Ser Leu Leu Gln Glu Ile Gly Lys Leu Lys Ala Lys Leu Asn Gly
145                 150                 155                 160 gaa gaa gaa gga gat gat gtt gat gaa gaa gag aac aac ttg gcg acg       528
Glu Glu Glu Gly Asp Asp Val Asp Glu Glu Glu Asn Asn Leu Ala Thr
                165                 170                 175 atg gag agt gat gtt tcc gtc aag gaa gaa gaa gtt tcg ttg ccg gag       576
Met Glu Ser Asp Val Ser Val Lys Glu Glu Glu Val Ser Leu Pro Glu
            180                 185                 190
```

```
cag atc aca gag ccg ccg tct tct cct ccg cag ctt cta gag cat tcc    624
Gln Ile Thr Glu Pro Pro Ser Ser Pro Pro Gln Leu Leu Glu His Ser
        195                 200                 205 gac agt ttc aat tac cgg agt ttc acc gac ctc cgc gac ctt ctt ccg    672
Asp Ser Phe Asn Tyr Arg Ser Phe Thr Asp Leu Arg Asp Leu Leu Pro
210                 215                 220 tta aag gcc gcg gct tcc tcc gtc gcc gcc gct gga tcg tcg gac agt    720
Leu Lys Ala Ala Ala Ser Ser Val Ala Ala Ala Gly Ser Ser Asp Ser
225                 230                 235                 240 agc gat tcg agc gcc gtg ttg aac gag gaa agt agc tct aac gtt acg    768
Ser Asp Ser Ser Ala Val Leu Asn Glu Glu Ser Ser Ser Asn Val Thr
        245                 250                 255 gcg gct ccg gcg acg gtt ccc ggc ggc agt ttc ttg cag ttt gtg aaa    816
Ala Ala Pro Ala Thr Val Pro Gly Gly Ser Phe Leu Gln Phe Val Lys
        260                 265                 270 atg gag cag acg gag gat cac gac gac ttt ctg agt gga gaa gaa gcg    864
Met Glu Gln Thr Glu Asp His Asp Asp Phe Leu Ser Gly Glu Glu Ala
        275                 280                 285 tgc ggg ttt ttc tcc gat gaa cag cca ccg tct ctg cac tgg tat tcc    912
Cys Gly Phe Phe Ser Asp Glu Gln Pro Pro Ser Leu His Trp Tyr Ser
290                 295                 300 acc gtt gat cag tgg aac tga                                        933
Thr Val Asp Gln Trp Asn
305                 310

<210> SEQ ID NO 12
<211> LENGTH: 310
<212> TYPE: PRT
<213> ORGANISM: Brassica napus

<400> SEQUENCE: 12

Met Met Lys Arg Leu Ser Ser Ser Asp Ser Val Gly Gly Leu Ile Ser
1               5                   10                  15

Leu Cys Pro Thr Thr Ser Thr Asp Gln Pro Asn Pro Arg Arg Cys Gly
            20                  25                  30

Arg Glu Phe Gln Ser Met Leu Glu Gly Tyr Glu Glu Glu Glu Glu Glu
        35                  40                  45

Ala Ile Thr Glu Glu Arg Gly Gln Thr Gly Leu Ala Glu Lys Lys Arg
    50                  55                  60

Arg Leu Asn Ile Asn Gln Val Lys Ala Leu Glu Lys Asn Phe Glu Leu
65                  70                  75                  80

Glu Asn Lys Leu Glu Pro Glu Arg Lys Val Lys Leu Ala Gln Glu Leu
                85                  90                  95

Gly Leu Gln Pro Arg Gln Val Ala Val Trp Phe Gln Asn Arg Arg Ala
            100                 105                 110

Arg Trp Lys Thr Lys Gln Leu Glu Lys Asp Tyr Gly Val Leu Lys Thr
        115                 120                 125

Gln Tyr Asp Ser Leu Arg His Asn Phe Asp Ser Leu Arg Arg Glu Asn
    130                 135                 140

Glu Ser Leu Leu Gln Glu Ile Gly Lys Leu Lys Ala Lys Leu Asn Gly
145                 150                 155                 160

Glu Glu Glu Gly Asp Val Asp Glu Glu Asn Asn Leu Ala Thr
                165                 170                 175

Met Glu Ser Asp Val Ser Val Lys Glu Glu Val Ser Leu Pro Glu
            180                 185                 190

Gln Ile Thr Glu Pro Pro Ser Ser Pro Pro Gln Leu Leu Glu His Ser
        195                 200                 205

Asp Ser Phe Asn Tyr Arg Ser Phe Thr Asp Leu Arg Asp Leu Leu Pro
```

```
                    210                 215                 220
Leu Lys Ala Ala Ala Ser Ser Val Ala Ala Gly Ser Ser Asp Ser
225                 230                 235                 240

Ser Asp Ser Ser Ala Val Leu Asn Glu Glu Ser Ser Asn Val Thr
                245                 250                 255

Ala Ala Pro Ala Thr Val Pro Gly Gly Ser Phe Leu Gln Phe Val Lys
                260                 265                 270

Met Glu Gln Thr Glu Asp His Asp Asp Phe Leu Ser Gly Glu Ala
                275                 280                 285

Cys Gly Phe Phe Ser Asp Glu Gln Pro Pro Ser Leu His Trp Tyr Ser
                290                 295                 300

Thr Val Asp Gln Trp Asn
305                 310

<210> SEQ ID NO 13
<211> LENGTH: 996
<212> TYPE: DNA
<213> ORGANISM: Glycine max
<220> FEATURE:
<221> NAME/KEY: CDS
<222> LOCATION: (1)..(996)
<223> OTHER INFORMATION: homeodomain leucine zipper protein (GM48923793)

<400> SEQUENCE: 13 atg gcg ggt agt gga agt gcc ttt tcc aac atc act agc ttt ctt cgc       48
Met Ala Gly Ser Gly Ser Ala Phe Ser Asn Ile Thr Ser Phe Leu Arg
1               5                   10                  15 acc caa caa ccc tct tct caa cct ctc gat tct tct ctc ttc ctc tct       96
Thr Gln Gln Pro Ser Ser Gln Pro Leu Asp Ser Ser Leu Phe Leu Ser
                20                  25                  30 gca cct tcc tct gct cct ttc ctc ggt tcg aga tcc atg atg agt ttt      144
Ala Pro Ser Ser Ala Pro Phe Leu Gly Ser Arg Ser Met Met Ser Phe
            35                  40                  45 gat gga gaa gga ggg aag ggg tgt aac ggc tcc ttc ttc cgc gcg ttt      192
Asp Gly Glu Gly Gly Lys Gly Cys Asn Gly Ser Phe Phe Arg Ala Phe
        50                  55                  60 gac atg gac gac aat ggg gat gag tgc atg gac gag tac ttt cat caa      240
Asp Met Asp Asp Asn Gly Asp Glu Cys Met Asp Glu Tyr Phe His Gln
65                  70                  75                  80 ccc gag aag aag cga cgt ctc tct gcg agc cag gtt cag ttt cta gag      288
Pro Glu Lys Lys Arg Arg Leu Ser Ala Ser Gln Val Gln Phe Leu Glu
                85                  90                  95 aag agc ttc gag gag gag aac aag ctt gaa ccc gag aga aag acc aaa      336
Lys Ser Phe Glu Glu Glu Asn Lys Leu Glu Pro Glu Arg Lys Thr Lys
                100                 105                 110 cta gcc aaa gac ctt ggt ttg cag cca cgg caa gtt gct att tgg ttc      384
Leu Ala Lys Asp Leu Gly Leu Gln Pro Arg Gln Val Ala Ile Trp Phe
            115                 120                 125 cag aac cgt aga gct cgg tgg aag aac aaa cag ctg gag aag gat tac      432
Gln Asn Arg Arg Ala Arg Trp Lys Asn Lys Gln Leu Glu Lys Asp Tyr
        130                 135                 140 gag act ctg cat gca agt ttt gag agt ctc aag tcc aac tat gac tgt      480
Glu Thr Leu His Ala Ser Phe Glu Ser Leu Lys Ser Asn Tyr Asp Cys
145                 150                 155                 160 ctt ctc aag gag aaa gac aag tta aaa gct gag gtg gcg agc ctc act      528
Leu Leu Lys Glu Lys Asp Lys Leu Lys Ala Glu Val Ala Ser Leu Thr
                165                 170                 175 gag aag gtg ctt gca aga ggg aaa caa gag ggg cac atg aag cag gct      576
Glu Lys Val Leu Ala Arg Gly Lys Gln Glu Gly His Met Lys Gln Ala
                180                 185                 190
```

```
gaa agt gaa agt gaa gaa aca aaa gga tta ttg cat ttg cag gaa cag      624
Glu Ser Glu Ser Glu Glu Thr Lys Gly Leu Leu His Leu Gln Glu Gln
            195                 200                 205 gaa cca ccc cag agg ctt tta ctg caa tca gtt tcg gag gga gaa gga      672
Glu Pro Pro Gln Arg Leu Leu Leu Gln Ser Val Ser Glu Gly Glu Gly
        210                 215                 220 tcc aaa gtc tct tct gtc gtt ggg ggt tgt aaa cag gaa gat atc agt      720
Ser Lys Val Ser Ser Val Val Gly Gly Cys Lys Gln Glu Asp Ile Ser
225                 230                 235                 240 tca gca agg agt gac att ttg gat tca gat agt cca cat tac acc gat      768
Ser Ala Arg Ser Asp Ile Leu Asp Ser Asp Ser Pro His Tyr Thr Asp
                245                 250                 255 gga gtt cac tct gcg ctg cta gag cat ggt gat tct tct tat gtg ttt      816
Gly Val His Ser Ala Leu Leu Glu His Gly Asp Ser Ser Tyr Val Phe
            260                 265                 270 gag cct gat caa tca gat atg tca caa gat gaa gaa gat aac ctc agc      864
Glu Pro Asp Gln Ser Asp Met Ser Gln Asp Glu Glu Asp Asn Leu Ser
        275                 280                 285 aag agt ctc tac cct tcg tac ctc ttt ccc aaa ctt gaa gaa gat gtg      912
Lys Ser Leu Tyr Pro Ser Tyr Leu Phe Pro Lys Leu Glu Glu Asp Val
                295                 300 gat tac tcc gac cca cct gaa agt tct tgt aat ttt gga ttt cct gag      960
Asp Tyr Ser Asp Pro Pro Glu Ser Ser Cys Asn Phe Gly Phe Pro Glu
305                 310                 315                 320 gaa gat cat gtc ctt tgg acc tgg gct tac tac taa                      996
Glu Asp His Val Leu Trp Thr Trp Ala Tyr Tyr
                325                 330

<210> SEQ ID NO 14
<211> LENGTH: 331
<212> TYPE: PRT
<213> ORGANISM: Glycine max

<400> SEQUENCE: 14

Met Ala Gly Ser Gly Ser Ala Phe Ser Asn Ile Thr Ser Phe Leu Arg
1               5                   10                  15

Thr Gln Gln Pro Ser Ser Gln Pro Leu Asp Ser Ser Leu Phe Leu Ser
            20                  25                  30

Ala Pro Ser Ser Ala Pro Phe Leu Gly Ser Arg Ser Met Met Ser Phe
        35                  40                  45

Asp Gly Glu Gly Gly Lys Gly Cys Asn Gly Ser Phe Phe Arg Ala Phe
    50                  55                  60

Asp Met Asp Asp Asn Gly Asp Glu Cys Met Asp Glu Tyr Phe His Gln
65                  70                  75                  80

Pro Glu Lys Lys Arg Arg Leu Ser Ala Ser Gln Val Gln Phe Leu Glu
                85                  90                  95

Lys Ser Phe Glu Glu Glu Asn Lys Leu Glu Pro Glu Arg Lys Thr Lys
            100                 105                 110

Leu Ala Lys Asp Leu Gly Leu Gln Pro Arg Gln Val Ala Ile Trp Phe
        115                 120                 125

Gln Asn Arg Arg Ala Arg Trp Lys Asn Lys Gln Leu Glu Lys Asp Tyr
    130                 135                 140

Glu Thr Leu His Ala Ser Phe Glu Ser Leu Lys Ser Asn Tyr Asp Cys
145                 150                 155                 160

Leu Leu Lys Glu Lys Asp Lys Leu Lys Ala Glu Val Ala Ser Leu Thr
                165                 170                 175

Glu Lys Val Leu Ala Arg Gly Lys Gln Glu Gly His Met Lys Gln Ala
            180                 185                 190
```

-continued

```
Glu Ser Glu Ser Glu Glu Thr Lys Gly Leu Leu His Leu Gln Glu Gln
        195                 200                 205

Glu Pro Pro Gln Arg Leu Leu Leu Gln Ser Val Ser Glu Gly Glu Gly
    210                 215                 220

Ser Lys Val Ser Val Val Gly Gly Cys Lys Gln Glu Asp Ile Ser
225                 230                 235                 240

Ser Ala Arg Ser Asp Ile Leu Asp Ser Asp Ser Pro His Tyr Thr Asp
                245                 250                 255

Gly Val His Ser Ala Leu Leu Glu His Gly Asp Ser Ser Tyr Val Phe
                260                 265                 270

Glu Pro Asp Gln Ser Asp Met Ser Gln Asp Glu Glu Asp Asn Leu Ser
                275                 280                 285

Lys Ser Leu Tyr Pro Ser Tyr Leu Phe Pro Lys Leu Glu Glu Asp Val
        290                 295                 300

Asp Tyr Ser Asp Pro Pro Glu Ser Ser Cys Asn Phe Gly Phe Pro Glu
305                 310                 315                 320

Glu Asp His Val Leu Trp Thr Trp Ala Tyr Tyr
                325                 330

<210> SEQ ID NO 15
<211> LENGTH: 1023
<212> TYPE: DNA
<213> ORGANISM: Triticum aestivum
<220> FEATURE:
<221> NAME/KEY: CDS
<222> LOCATION: (1)..(1023)
<223> OTHER INFORMATION: homeodomain leucine zipper protein (TA55969932)

<400> SEQUENCE: 15 atg gag ccc ggc cgg ctc atc ttc aac acg tcg ggc tcc ggc aac gga      48
Met Glu Pro Gly Arg Leu Ile Phe Asn Thr Ser Gly Ser Gly Asn Gly
1               5                   10                  15 cag atg ctc ttc atg gac tgc ggc gcg ggc ggc atc gcc ggc gcg gcc      96
Gln Met Leu Phe Met Asp Cys Gly Ala Gly Gly Ile Ala Gly Ala Ala
            20                  25                  30 ggc atg ttc cat cga ggg gtg aga ccg gtc ctc ggc ggc atg gaa gaa     144
Gly Met Phe His Arg Gly Val Arg Pro Val Leu Gly Gly Met Glu Glu
        35                  40                  45 ggg cgc ggc gtg aag cgg ccc ttc ttc acc tcg ccg gat gac atg ctg     192
Gly Arg Gly Val Lys Arg Pro Phe Phe Thr Ser Pro Asp Asp Met Leu
    50                  55                  60 gag gag gag tac tac gac gag cag ctc ccg gag aag aag cgg cgc ctc     240
Glu Glu Glu Tyr Tyr Asp Glu Gln Leu Pro Glu Lys Lys Arg Arg Leu
65                  70                  75                  80 acg ccg gag cag gtc cac ctg ctg gag agg agc ttc gag gag gag aac     288
Thr Pro Glu Gln Val His Leu Leu Glu Arg Ser Phe Glu Glu Glu Asn
                85                  90                  95 aag ctg gag ccg gag agg aag acg gag ctg gcc cgc aag ctc ggg ctg     336
Lys Leu Glu Pro Glu Arg Lys Thr Glu Leu Ala Arg Lys Leu Gly Leu
            100                 105                 110 cag cca cgg cag gtg gcc gtc tgg ttc cag aac cgc cgc gcc cgg tgg     384
Gln Pro Arg Gln Val Ala Val Trp Phe Gln Asn Arg Arg Ala Arg Trp
        115                 120                 125 aag aca aag acg ctg gag cgc gac ttc gac cgc ctc aag gcg tcc ttc     432
Lys Thr Lys Thr Leu Glu Arg Asp Phe Asp Arg Leu Lys Ala Ser Phe
    130                 135                 140 gac gcc ctc cgc gcc gac cac gac gcg ctc ctc cag gac aac cac cgg     480
Asp Ala Leu Arg Ala Asp His Asp Ala Leu Leu Gln Asp Asn His Arg
145                 150                 155                 160 ctc cgg tca cag gtg gta acg ttg acc gag aag atg caa gat aag gag     528
```

```
Leu Arg Ser Gln Val Val Thr Leu Thr Glu Lys Met Gln Asp Lys Glu
                165                 170                 175 gcg ccg gaa ggc agc ttc ggt gca gcc gcc gac gcc tcg gag ccg gag      576
Ala Pro Glu Gly Ser Phe Gly Ala Ala Ala Asp Ala Ser Glu Pro Glu
            180                 185                 190 cag gcg gcg gcg gag gcg aag gct tcc ttg gcc gac gcc gag gag cag      624
Gln Ala Ala Ala Glu Ala Lys Ala Ser Leu Ala Asp Ala Glu Glu Gln
        195                 200                 205 gcc gcg gca gcg gag gcg ttc gag gtg gtg cag cag cag ctg cac gtg      672
Ala Ala Ala Ala Glu Ala Phe Glu Val Val Gln Gln Gln Leu His Val
    210                 215                 220 aag gac gag gag agg ctg agc ccg ggg agc ggc ggg agc gcg gtg ctg      720
Lys Asp Glu Glu Arg Leu Ser Pro Gly Ser Gly Gly Ser Ala Val Leu
225                 230                 235                 240 gac gcg agg gac gcg ctg ctc ggg agc gga tgc ggc ctc gcc ggc gtg      768
Asp Ala Arg Asp Ala Leu Leu Gly Ser Gly Cys Gly Leu Ala Gly Val
                245                 250                 255 gtg gac agc agc gtg gac tcg tac tgc ttc ccg ggg ggc gcc ggc ggc      816
Val Asp Ser Ser Val Asp Ser Tyr Cys Phe Pro Gly Gly Ala Gly Gly
            260                 265                 270 gac gag tac cac gag tgc gtg gtg ggc ccc gtg gcg ggc ggc atc cag      864
Asp Glu Tyr His Glu Cys Val Val Gly Pro Val Ala Gly Gly Ile Gln
        275                 280                 285 tcg gag gag gac gac ggc gcg ggc agc gac gag ggc tgc agc tac tac      912
Ser Glu Glu Asp Asp Gly Ala Gly Ser Asp Glu Gly Cys Ser Tyr Tyr
    290                 295                 300 ccc gac gac gcc gcc gtc ttc ttc gcc gcc gcg caa ggg cac ggc cac      960
Pro Asp Asp Ala Ala Val Phe Phe Ala Ala Ala Gln Gly His Gly His
305                 310                 315                 320 cat cgc acg gac gac gac gat cag cag gac gac ggc cag atc agc tac     1008
His Arg Thr Asp Asp Asp Asp Gln Gln Asp Asp Gly Gln Ile Ser Tyr
                325                 330                 335 tgg atg tgg aac tag                                                 1023
Trp Met Trp Asn
            340

<210> SEQ ID NO 16
<211> LENGTH: 340
<212> TYPE: PRT
<213> ORGANISM: Triticum aestivum

<400> SEQUENCE: 16

Met Glu Pro Gly Arg Leu Ile Phe Asn Thr Ser Gly Ser Gly Asn Gly
1               5                   10                  15

Gln Met Leu Phe Met Asp Cys Gly Ala Gly Gly Ile Ala Gly Ala Ala
            20                  25                  30

Gly Met Phe His Arg Gly Val Arg Pro Val Leu Gly Gly Met Glu Glu
        35                  40                  45

Gly Arg Gly Val Lys Arg Pro Phe Phe Thr Ser Pro Asp Asp Met Leu
    50                  55                  60

Glu Glu Glu Tyr Tyr Asp Glu Gln Leu Pro Glu Lys Lys Arg Arg Leu
65                  70                  75                  80

Thr Pro Glu Gln Val His Leu Leu Glu Arg Ser Phe Glu Glu Glu Asn
                85                  90                  95

Lys Leu Glu Pro Glu Arg Lys Thr Glu Leu Ala Arg Lys Leu Gly Leu
            100                 105                 110

Gln Pro Arg Gln Val Ala Val Trp Phe Gln Asn Arg Arg Ala Arg Trp
        115                 120                 125

Lys Thr Lys Thr Leu Glu Arg Asp Phe Asp Arg Leu Lys Ala Ser Phe
```

-continued

```
                130                 135                 140
Asp Ala Leu Arg Ala Asp His Asp Ala Leu Leu Gln Asp Asn His Arg
145                 150                 155                 160

Leu Arg Ser Gln Val Val Thr Leu Thr Glu Lys Met Gln Asp Lys Glu
                165                 170                 175

Ala Pro Glu Gly Ser Phe Gly Ala Ala Asp Ala Ser Glu Pro Glu
            180                 185                 190

Gln Ala Ala Ala Glu Ala Lys Ala Ser Leu Ala Asp Ala Glu Glu Gln
                195                 200                 205

Ala Ala Ala Glu Ala Phe Glu Val Val Gln Gln Gln Leu His Val
    210                 215                 220

Lys Asp Glu Glu Arg Leu Ser Pro Gly Ser Gly Ser Ala Val Leu
225                 230                 235                 240

Asp Ala Arg Asp Ala Leu Leu Gly Ser Gly Cys Gly Leu Ala Gly Val
                245                 250                 255

Val Asp Ser Ser Val Asp Ser Tyr Cys Phe Pro Gly Gly Ala Gly Gly
            260                 265                 270

Asp Glu Tyr His Glu Cys Val Val Gly Pro Val Ala Gly Gly Ile Gln
                275                 280                 285

Ser Glu Glu Asp Asp Gly Ala Gly Ser Asp Glu Gly Cys Ser Tyr Tyr
            290                 295                 300

Pro Asp Asp Ala Ala Val Phe Phe Ala Ala Gln Gly His Gly His
305                 310                 315                 320

His Arg Thr Asp Asp Asp Gln Gln Asp Asp Gly Gln Ile Ser Tyr
                325                 330                 335

Trp Met Trp Asn
            340

<210> SEQ ID NO 17
<211> LENGTH: 534
<212> TYPE: DNA
<213> ORGANISM: Brassica napus
<220> FEATURE:
<221> NAME/KEY: CDS
<222> LOCATION: (1)..(534)
<223> OTHER INFORMATION: zinc finger protein containing an A20 domain
      and an AN1 domain (BN47310186)

<400> SEQUENCE: 17 atg gac cac gac aaa aca gga tgc caa agc cca cct gaa ggt ccc aag      48
Met Asp His Asp Lys Thr Gly Cys Gln Ser Pro Pro Glu Gly Pro Lys
1               5                   10                  15 cta tgc atc aac aac tgc ggt ttc ttc gga agc gct gcc aca atg aac      96
Leu Cys Ile Asn Asn Cys Gly Phe Phe Gly Ser Ala Ala Thr Met Asn
                20                  25                  30 atg tgt tcc aag tgt cac aag gct atc ctg ttt caa cag gaa cag ggg     144
Met Cys Ser Lys Cys His Lys Ala Ile Leu Phe Gln Gln Glu Gln Gly
            35                  40                  45 gct agg ttt gca tct gca gtg tct ggt ggt aca tca tca tcc agc aac     192
Ala Arg Phe Ala Ser Ala Val Ser Gly Gly Thr Ser Ser Ser Ser Asn
        50                  55                  60 atc tta aag gaa acc ttt gct gct acc gcg ctg gtt gat gct gaa acc     240
Ile Leu Lys Glu Thr Phe Ala Ala Thr Ala Leu Val Asp Ala Glu Thr
65                  70                  75                  80 aaa tcc gtt gag ccg gtg gct gtc tct gta cag cca tct tct gtc caa     288
Lys Ser Val Glu Pro Val Ala Val Ser Val Gln Pro Ser Ser Val Gln
                85                  90                  95 gtt gcc gca gag gta gta gct cca gaa gcc gct gca gca aaa cta aag     336
Val Ala Ala Glu Val Val Ala Pro Glu Ala Ala Ala Ala Lys Leu Lys
```

```
                100             105             110
gaa gga cca agc cga tgt gct act tgc aat aaa cgg gtt ggt ctg act      384
Glu Gly Pro Ser Arg Cys Ala Thr Cys Asn Lys Arg Val Gly Leu Thr
            115                 120                 125 gga ttc aaa tgt cgc tgt ggt gac ctc ttc tgc ggg acg cac cgt tat      432
Gly Phe Lys Cys Arg Cys Gly Asp Leu Phe Cys Gly Thr His Arg Tyr
        130                 135                 140 gca gac ata cac aac tgc tcc ttc aat tac cat gcc gct gcg caa gaa      480
Ala Asp Ile His Asn Cys Ser Phe Asn Tyr His Ala Ala Ala Gln Glu
145                 150                 155                 160 gct ata gct aaa gca aac ccg gtt gtg aag gca gag aag ctt gac aaa      528
Ala Ile Ala Lys Ala Asn Pro Val Val Lys Ala Glu Lys Leu Asp Lys
                165                 170                 175 atc tga                                                              534
Ile
```

<210> SEQ ID NO 18
<211> LENGTH: 177
<212> TYPE: PRT
<213> ORGANISM: Brassica napus

<400> SEQUENCE: 18

```
Met Asp His Asp Lys Thr Gly Cys Gln Ser Pro Glu Gly Pro Lys
1               5                   10                  15

Leu Cys Ile Asn Asn Cys Gly Phe Phe Gly Ser Ala Ala Thr Met Asn
            20                  25                  30

Met Cys Ser Lys Cys His Lys Ala Ile Leu Phe Gln Gln Glu Gln Gly
        35                  40                  45

Ala Arg Phe Ala Ser Ala Val Ser Gly Gly Thr Ser Ser Ser Ser Asn
    50                  55                  60

Ile Leu Lys Glu Thr Phe Ala Ala Thr Ala Leu Val Asp Ala Glu Thr
65                  70                  75                  80

Lys Ser Val Glu Pro Val Ala Val Ser Val Gln Pro Ser Ser Val Gln
                85                  90                  95

Val Ala Ala Glu Val Val Ala Pro Glu Ala Ala Ala Lys Leu Lys
                100                 105                 110

Glu Gly Pro Ser Arg Cys Ala Thr Cys Asn Lys Arg Val Gly Leu Thr
            115                 120                 125

Gly Phe Lys Cys Arg Cys Gly Asp Leu Phe Cys Gly Thr His Arg Tyr
        130                 135                 140

Ala Asp Ile His Asn Cys Ser Phe Asn Tyr His Ala Ala Ala Gln Glu
145                 150                 155                 160

Ala Ile Ala Lys Ala Asn Pro Val Val Lys Ala Glu Lys Leu Asp Lys
                165                 170                 175

Ile
```

<210> SEQ ID NO 19
<211> LENGTH: 564
<212> TYPE: DNA
<213> ORGANISM: Brassica napus
<220> FEATURE:
<221> NAME/KEY: CDS
<222> LOCATION: (1)..(564)
<223> OTHER INFORMATION: zinc finger protein containing an A20 domain
      and an AN1 domain (BN51359456)

<400> SEQUENCE: 19

```
atg gcg gaa gag cat cga tgc cag acg ccg gaa ggc cac cgt ctc tgt      48
Met Ala Glu Glu His Arg Cys Gln Thr Pro Glu Gly His Arg Leu Cys
1               5                   10                  15
```

```
gct aac aac tgc ggc ttc ctc ggc agc tcc gcc acc atg aat cta tgc      96
Ala Asn Asn Cys Gly Phe Leu Gly Ser Ser Ala Thr Met Asn Leu Cys
         20                  25                  30 tcc aac tgc tac ggc gat ctc tgc ctt aag caa cag caa gct tcc atg     144
Ser Asn Cys Tyr Gly Asp Leu Cys Leu Lys Gln Gln Gln Ala Ser Met
         35                  40                  45 aaa tcc acc gtc gaa tcc tct ctc tcc gcc gta tct cct ccg tcg tca     192
Lys Ser Thr Val Glu Ser Ser Leu Ser Ala Val Ser Pro Pro Ser Ser
 50                  55                  60 gag atc ggc tct atg caa tcc acc gtt gaa tcc tct ctc tcc gac gta     240
Glu Ile Gly Ser Met Gln Ser Thr Val Glu Ser Ser Leu Ser Asp Val
 65                  70                  75                  80 tct cct cca tca ccg gag acc att tcc atc tcc tct cca atg atc cag     288
Ser Pro Pro Ser Pro Glu Thr Ile Ser Ile Ser Ser Pro Met Ile Gln
                     85                  90                  95 cct ctc gtt cga aac cca tca gct gaa ttg gag gta acg gcg acg aag     336
Pro Leu Val Arg Asn Pro Ser Ala Glu Leu Glu Val Thr Ala Thr Lys
                100                 105                 110 acg gtg act ccg ccg ccg gag cag cag cag aaa cgg ccg aat cgg tgc     384
Thr Val Thr Pro Pro Pro Glu Gln Gln Gln Lys Arg Pro Asn Arg Cys
            115                 120                 125 acg acg tgt agg aaa cgg gtc ggg ttg acc ggg ttc aag tgc cgg tgc     432
Thr Thr Cys Arg Lys Arg Val Gly Leu Thr Gly Phe Lys Cys Arg Cys
        130                 135                 140 ggg acg act ttt tgc ggg gct cac agg tac ccg gag gtc cat gga tgc     480
Gly Thr Thr Phe Cys Gly Ala His Arg Tyr Pro Glu Val His Gly Cys
145                 150                 155                 160 acc ttc gat ttc aaa tcg gcc ggt cgc gaa gag atc gcc aag gcg aac     528
Thr Phe Asp Phe Lys Ser Ala Gly Arg Glu Glu Ile Ala Lys Ala Asn
                    165                 170                 175 cca ctc gtc aaa gcg gcg aag ctt cag aag att tga                     564
Pro Leu Val Lys Ala Ala Lys Leu Gln Lys Ile
                180                 185

<210> SEQ ID NO 20
<211> LENGTH: 187
<212> TYPE: PRT
<213> ORGANISM: Brassica napus

<400> SEQUENCE: 20

Met Ala Glu Glu His Arg Cys Gln Thr Pro Glu Gly His Arg Leu Cys
 1               5                  10                  15

Ala Asn Asn Cys Gly Phe Leu Gly Ser Ser Ala Thr Met Asn Leu Cys
             20                  25                  30

Ser Asn Cys Tyr Gly Asp Leu Cys Leu Lys Gln Gln Gln Ala Ser Met
         35                  40                  45

Lys Ser Thr Val Glu Ser Ser Leu Ser Ala Val Ser Pro Pro Ser Ser
 50                  55                  60

Glu Ile Gly Ser Met Gln Ser Thr Val Glu Ser Ser Leu Ser Asp Val
 65                  70                  75                  80

Ser Pro Pro Ser Pro Glu Thr Ile Ser Ile Ser Ser Pro Met Ile Gln
                 85                  90                  95

Pro Leu Val Arg Asn Pro Ser Ala Glu Leu Glu Val Thr Ala Thr Lys
                100                 105                 110

Thr Val Thr Pro Pro Pro Glu Gln Gln Gln Lys Arg Pro Asn Arg Cys
            115                 120                 125

Thr Thr Cys Arg Lys Arg Val Gly Leu Thr Gly Phe Lys Cys Arg Cys
        130                 135                 140
```

```
Gly Thr Thr Phe Cys Gly Ala His Arg Tyr Pro Glu Val His Gly Cys
145                 150                 155                 160

Thr Phe Asp Phe Lys Ser Ala Gly Arg Glu Glu Ile Ala Lys Ala Asn
                165                 170                 175

Pro Leu Val Lys Ala Ala Lys Leu Gln Lys Ile
            180                 185

<210> SEQ ID NO 21
<211> LENGTH: 465
<212> TYPE: DNA
<213> ORGANISM: Hordeum vulgare
<220> FEATURE:
<221> NAME/KEY: CDS
<222> LOCATION: (1)..(465)
<223> OTHER INFORMATION: zinc finger protein containing an A20 domain
      and an AN1 domain (HV62552639)

<400> SEQUENCE: 21 atg gcc cag gag agt tgt gat ctc aac aag gac gag gcc gag atc ctg      48
Met Ala Gln Glu Ser Cys Asp Leu Asn Lys Asp Glu Ala Glu Ile Leu
1               5                   10                  15 aag cca tcc tcc tcc aca cct tcg cct cct tcg cca gcc aca cca cca      96
Lys Pro Ser Ser Ser Thr Pro Ser Pro Pro Ser Pro Ala Thr Pro Pro
            20                  25                  30 cca cca acc gct caa ata cca gaa cca caa cct cca cac tca cca cca     144
Pro Pro Thr Ala Gln Ile Pro Glu Pro Gln Pro Pro His Ser Pro Pro
        35                  40                  45 caa cca ccg gca gct caa ttc ttg tcc agg ccc tgc gag gtt gtt ccc     192
Gln Pro Pro Ala Ala Gln Phe Leu Ser Arg Pro Cys Glu Val Val Pro
50                  55                  60 ata gag act tcc aaa aag agg aaa cat gct gat gcg gtg tca atg gcc     240
Ile Glu Thr Ser Lys Lys Arg Lys His Ala Asp Ala Val Ser Met Ala
65                  70                  75                  80 att gtg gtt gag cca ttg tcg tct gtg ctg ttc gtt aac cgt tgc aac     288
Ile Val Val Glu Pro Leu Ser Ser Val Leu Phe Val Asn Arg Cys Asn
                85                  90                  95 gtg tgc cgc aag aga gtt ggt ttg acc ggg ttc cgt tgc cgg tgt gag     336
Val Cys Arg Lys Arg Val Gly Leu Thr Gly Phe Arg Cys Arg Cys Glu
            100                 105                 110 aag ctc ttt tgt ccg cgc cac cgg cat tca gaa agc cac gac tgc tca     384
Lys Leu Phe Cys Pro Arg His Arg His Ser Glu Ser His Asp Cys Ser
        115                 120                 125 ttt gat tat aaa act gtg ggt cgg gag gag att gcc cgg gca aac cct     432
Phe Asp Tyr Lys Thr Val Gly Arg Glu Glu Ile Ala Arg Ala Asn Pro
130                 135                 140 ctg atc agg gct gcc aag atc att agg ata tga                         465
Leu Ile Arg Ala Ala Lys Ile Ile Arg Ile
145                 150

<210> SEQ ID NO 22
<211> LENGTH: 154
<212> TYPE: PRT
<213> ORGANISM: Hordeum vulgare

<400> SEQUENCE: 22

Met Ala Gln Glu Ser Cys Asp Leu Asn Lys Asp Glu Ala Glu Ile Leu
1               5                   10                  15

Lys Pro Ser Ser Ser Thr Pro Ser Pro Pro Ser Pro Ala Thr Pro Pro
            20                  25                  30

Pro Pro Thr Ala Gln Ile Pro Glu Pro Gln Pro Pro His Ser Pro Pro
        35                  40                  45

Gln Pro Pro Ala Ala Gln Phe Leu Ser Arg Pro Cys Glu Val Val Pro
```

-continued

```
                    50                  55                  60
Ile Glu Thr Ser Lys Lys Arg Lys His Ala Asp Ala Val Ser Met Ala
 65                  70                  75                  80

Ile Val Val Glu Pro Leu Ser Ser Val Leu Phe Val Asn Arg Cys Asn
                 85                  90                  95

Val Cys Arg Lys Arg Val Gly Leu Thr Gly Phe Arg Cys Arg Cys Glu
            100                 105                 110

Lys Leu Phe Cys Pro Arg His Arg His Ser Glu Ser His Asp Cys Ser
        115                 120                 125

Phe Asp Tyr Lys Thr Val Gly Arg Glu Glu Ile Ala Arg Ala Asn Pro
    130                 135                 140

Leu Ile Arg Ala Ala Lys Ile Ile Arg Ile
145                 150

<210> SEQ ID NO 23
<211> LENGTH: 516
<212> TYPE: DNA
<213> ORGANISM: Zea mays
<220> FEATURE:
<221> NAME/KEY: CDS
<222> LOCATION: (1)..(516)
<223> OTHER INFORMATION: zinc finger protein containing an A20 domain
      and an AN1 domain (ZM61995511)

<400> SEQUENCE: 23 atg gaa cac aag gag gcg ggc tgc cag cag ccg gag ggc cca atc cta      48
Met Glu His Lys Glu Ala Gly Cys Gln Gln Pro Glu Gly Pro Ile Leu
  1               5                  10                  15 tgc atc aat aac tgc ggc ttc ttc ggc agt gct gcg acg atg aac atg      96
Cys Ile Asn Asn Cys Gly Phe Phe Gly Ser Ala Ala Thr Met Asn Met
                 20                  25                  30 tgc tcc aag tgc cac aag gag atg ata acg aag cag gag cag gcc cag     144
Cys Ser Lys Cys His Lys Glu Met Ile Thr Lys Gln Glu Gln Ala Gln
             35                  40                  45 ctg gct gcc tcc ccc atc gat agc att gtc aat ggc ggt gac ggc ggg     192
Leu Ala Ala Ser Pro Ile Asp Ser Ile Val Asn Gly Gly Asp Gly Gly
         50                  55                  60 aaa gga cct gta att gct gca tct gta aat gtg gca gtt cct caa gtt     240
Lys Gly Pro Val Ile Ala Ala Ser Val Asn Val Ala Val Pro Gln Val
 65                  70                  75                  80 gag cag aag act att gtt gtg cag ccc atg ctt gta gct gaa acc agc     288
Glu Gln Lys Thr Ile Val Val Gln Pro Met Leu Val Ala Glu Thr Ser
                 85                  90                  95 gag gct gct gct gta atc ccc aag gcc aag gaa ggc cca gac cgg tgc     336
Glu Ala Ala Ala Val Ile Pro Lys Ala Lys Glu Gly Pro Asp Arg Cys
            100                 105                 110 gcg gcc tgc agg aag cgt gtt ggg ctg acg gga ttt agc tgc cga tgc     384
Ala Ala Cys Arg Lys Arg Val Gly Leu Thr Gly Phe Ser Cys Arg Cys
        115                 120                 125 ggg aac atg tac tgt tcg gtg cac cgc tac tcc gac aaa cat gac tgt     432
Gly Asn Met Tyr Cys Ser Val His Arg Tyr Ser Asp Lys His Asp Cys
    130                 135                 140 cag ttc gac tat cgg act gca gca agg gac gcg att gcc aag gcc aat     480
Gln Phe Asp Tyr Arg Thr Ala Ala Arg Asp Ala Ile Ala Lys Ala Asn
145                 150                 155                 160 cct gtg gtg agg gcg gag aag ctc gac aag atc tga                     516
Pro Val Val Arg Ala Glu Lys Leu Asp Lys Ile
                165                 170

<210> SEQ ID NO 24
<211> LENGTH: 171
```

```
<212> TYPE: PRT
<213> ORGANISM: Zea mays

<400> SEQUENCE: 24

Met Glu His Lys Glu Ala Gly Cys Gln Gln Pro Glu Gly Pro Ile Leu
1               5                   10                  15

Cys Ile Asn Asn Cys Gly Phe Phe Gly Ser Ala Ala Thr Met Asn Met
            20                  25                  30

Cys Ser Lys Cys His Lys Glu Met Ile Thr Lys Gln Glu Gln Ala Gln
        35                  40                  45

Leu Ala Ala Ser Pro Ile Asp Ser Ile Val Asn Gly Gly Asp Gly Gly
    50                  55                  60

Lys Gly Pro Val Ile Ala Ala Ser Val Asn Val Ala Val Pro Gln Val
65                  70                  75                  80

Glu Gln Lys Thr Ile Val Val Gln Pro Met Leu Val Ala Glu Thr Ser
                85                  90                  95

Glu Ala Ala Ala Val Ile Pro Lys Ala Lys Glu Gly Pro Asp Arg Cys
            100                 105                 110

Ala Ala Cys Arg Lys Arg Val Gly Leu Thr Gly Phe Ser Cys Arg Cys
        115                 120                 125

Gly Asn Met Tyr Cys Ser Val His Arg Tyr Ser Asp Lys His Asp Cys
    130                 135                 140

Gln Phe Asp Tyr Arg Thr Ala Ala Arg Asp Ala Ile Ala Lys Ala Asn
145                 150                 155                 160

Pro Val Val Arg Ala Glu Lys Leu Asp Lys Ile
                165                 170

<210> SEQ ID NO 25
<211> LENGTH: 720
<212> TYPE: DNA
<213> ORGANISM: Linum usitatissimum
<220> FEATURE:
<221> NAME/KEY: CDS
<222> LOCATION: (1)..(720)
<223> OTHER INFORMATION: zinc finger protein containing an A20 domain
      and an AN1 domain (LU61567101)

<400> SEQUENCE: 25 atg gct cct tca cct tgc gtc cac ggc tgc acg gcc aat tgc ccc cgc      48
Met Ala Pro Ser Pro Cys Val His Gly Cys Thr Ala Asn Cys Pro Arg
1               5                   10                  15 tgc cac tct tac gga cac ccc atc ttc ggg aac tca gat ctc gcc gct      96
Cys His Ser Tyr Gly His Pro Ile Phe Gly Asn Ser Asp Leu Ala Ala
            20                  25                  30 ggc ggc agc gat acg tcc acg tcg gtg ttt gga aaa gta gga tcc gtc     144
Gly Gly Ser Asp Thr Ser Thr Ser Val Phe Gly Lys Val Gly Ser Val
        35                  40                  45 gtg att cag tcg cct gcg aag aat cac gcg ttc ggc caa gct tgt ggc     192
Val Ile Gln Ser Pro Ala Lys Asn His Ala Phe Gly Gln Ala Cys Gly
    50                  55                  60 ccg gtt ttt ccc tcg agc tcc tcc cct ttc cgc cgc atc aag ttc ggc     240
Pro Val Phe Pro Ser Ser Ser Ser Pro Phe Arg Arg Ile Lys Phe Gly
65                  70                  75                  80 ccc aaa gat ggc gag ggg aaa gga ccg ctg aag ccg atc gag aag cag     288
Pro Lys Asp Gly Glu Gly Lys Gly Pro Leu Lys Pro Ile Glu Lys Gln
                85                  90                  95 ccg tcg aag aag cgt ccg ttc tgc ttc tct ccc gac gag acg att gac     336
Pro Ser Lys Lys Arg Pro Phe Cys Phe Ser Pro Asp Glu Thr Ile Asp
            100                 105                 110 gcg acg gtt cct ccg tcc acc aaa ccg ttc ggt tcg ttc cgt tcc gtc     384
Ala Thr Val Pro Pro Ser Thr Lys Pro Phe Gly Ser Phe Arg Ser Val
```

```
Ala Thr Val Pro Pro Ser Thr Lys Pro Phe Gly Ser Phe Arg Ser Val
        115                 120                 125 tgt gtc acg gac gcc gac gag gcc agg ttg aag gcg aac cgc gag ttc    432
Cys Val Thr Asp Ala Asp Glu Ala Arg Leu Lys Ala Asn Arg Glu Phe
130                 135                 140 ttc gct ccg gta tcc cgc aaa cgt ggc ttc gat ccg act gac atg acc    480
Phe Ala Pro Val Ser Arg Lys Arg Gly Phe Asp Pro Thr Asp Met Thr
145                 150                 155                 160 ttc ggt aac gcc gcc gcc gct gcg gct aat gcg agg gag gaa gcg aag    528
Phe Gly Asn Ala Ala Ala Ala Ala Asn Ala Arg Glu Glu Ala Lys
        165                 170                 175 aag tgg tgc ggc agt tgc aag aag cgc gtg ggg ctg tta ggg ttc aag    576
Lys Trp Cys Gly Ser Cys Lys Lys Arg Val Gly Leu Leu Gly Phe Lys
        180                 185                 190 tgc agg tgt acg aag ttc ttc tgt ggg aag cat cgg tat cct gag gag    624
Cys Arg Cys Thr Lys Phe Phe Cys Gly Lys His Arg Tyr Pro Glu Glu
        195                 200                 205 cat ggt tgt acg ttc gat cat gtg gcg ttc ggg agg cgg att atc gag    672
His Gly Cys Thr Phe Asp His Val Ala Phe Gly Arg Arg Ile Ile Glu
210                 215                 220 aaa cag aat cct gtt ctc gag acc gac aag ctg gtg gac aga atc tga    720
Lys Gln Asn Pro Val Leu Glu Thr Asp Lys Leu Val Asp Arg Ile
225                 230                 235

<210> SEQ ID NO 26
<211> LENGTH: 239
<212> TYPE: PRT
<213> ORGANISM: Linum usitatissimum

<400> SEQUENCE: 26

Met Ala Pro Ser Pro Cys Val His Gly Cys Thr Ala Asn Cys Pro Arg
1               5                   10                  15

Cys His Ser Tyr Gly His Pro Ile Phe Gly Asn Ser Asp Leu Ala Ala
            20                  25                  30

Gly Gly Ser Asp Thr Ser Thr Ser Val Phe Gly Lys Val Gly Ser Val
        35                  40                  45

Val Ile Gln Ser Pro Ala Lys Asn His Ala Phe Gly Gln Ala Cys Gly
50                  55                  60

Pro Val Phe Pro Ser Ser Ser Pro Phe Arg Arg Ile Lys Phe Gly
65              70                  75                  80

Pro Lys Asp Gly Glu Gly Lys Gly Pro Leu Lys Pro Ile Glu Lys Gln
                85                  90                  95

Pro Ser Lys Lys Arg Pro Phe Cys Phe Ser Pro Asp Glu Thr Ile Asp
            100                 105                 110

Ala Thr Val Pro Pro Ser Thr Lys Pro Phe Gly Ser Phe Arg Ser Val
        115                 120                 125

Cys Val Thr Asp Ala Asp Glu Ala Arg Leu Lys Ala Asn Arg Glu Phe
130                 135                 140

Phe Ala Pro Val Ser Arg Lys Arg Gly Phe Asp Pro Thr Asp Met Thr
145                 150                 155                 160

Phe Gly Asn Ala Ala Ala Ala Ala Asn Ala Arg Glu Glu Ala Lys
        165                 170                 175

Lys Trp Cys Gly Ser Cys Lys Lys Arg Val Gly Leu Leu Gly Phe Lys
        180                 185                 190

Cys Arg Cys Thr Lys Phe Phe Cys Gly Lys His Arg Tyr Pro Glu Glu
        195                 200                 205

His Gly Cys Thr Phe Asp His Val Ala Phe Gly Arg Arg Ile Ile Glu
210                 215                 220
```

```
Lys Gln Asn Pro Val Leu Glu Thr Asp Lys Leu Val Asp Arg Ile
225                 230                 235

<210> SEQ ID NO 27
<211> LENGTH: 510
<212> TYPE: DNA
<213> ORGANISM: Linum usitatissimum
<220> FEATURE:
<221> NAME/KEY: CDS
<222> LOCATION: (1)..(510)
<223> OTHER INFORMATION: zinc finger protein containing an A20 domain
      and an AN1 domain (LU61893412)

<400> SEQUENCE: 27 atg gac cat gac gag gca ggc tgc cag gct cct tcc gat cat cct att        48
Met Asp His Asp Glu Ala Gly Cys Gln Ala Pro Ser Asp His Pro Ile
1               5                   10                  15 ctg tgc gtt aac aat tgc ggc ttc ttc gga agt gct gcc acc atg aac        96
Leu Cys Val Asn Asn Cys Gly Phe Phe Gly Ser Ala Ala Thr Met Asn
            20                  25                  30 atg tgc tca aag tgc cac aag gat acg atg cta aac caa gag caa tcc       144
Met Cys Ser Lys Cys His Lys Asp Thr Met Leu Asn Gln Glu Gln Ser
        35                  40                  45 aag ctt gct gct tca tcg gca gca agt atc ctc aac gga tcg tcg atg       192
Lys Leu Ala Ala Ser Ser Ala Ala Ser Ile Leu Asn Gly Ser Ser Met
    50                  55                  60 agc ctc gga agg gaa ctc gtt att gct gct aag acc aat tcg gta gaa       240
Ser Leu Gly Arg Glu Leu Val Ile Ala Ala Lys Thr Asn Ser Val Glu
65                  70                  75                  80 ccc aag acc atc tcc gtc caa cca tct tct gct tca agt gct gaa gag       288
Pro Lys Thr Ile Ser Val Gln Pro Ser Ser Ala Ser Ser Ala Glu Glu
                85                  90                  95 agt atc gaa atg aag ctg cca aaa gaa ggg ccc agt agg tgc aac act       336
Ser Ile Glu Met Lys Leu Pro Lys Glu Gly Pro Ser Arg Cys Asn Thr
            100                 105                 110 tgc aac aaa cgt gtc ggt ttg acc gga ttc aaa tgt cgg tgc gag aac       384
Cys Asn Lys Arg Val Gly Leu Thr Gly Phe Lys Cys Arg Cys Glu Asn
        115                 120                 125 atg ttc tgc gca aac cat cgc tac tcg gac aag cac aat tgc ccc ttt       432
Met Phe Cys Ala Asn His Arg Tyr Ser Asp Lys His Asn Cys Pro Phe
    130                 135                 140 gat tac cgc act gct ggc cgt gaa gct atc tca aag gcc aat cct ttg       480
Asp Tyr Arg Thr Ala Gly Arg Glu Ala Ile Ser Lys Ala Asn Pro Leu
145                 150                 155                 160 gtg aag gcg gag aag ctc gac aaa atc tga                               510
Val Lys Ala Glu Lys Leu Asp Lys Ile
                165

<210> SEQ ID NO 28
<211> LENGTH: 169
<212> TYPE: PRT
<213> ORGANISM: Linum usitatissimum

<400> SEQUENCE: 28

Met Asp His Asp Glu Ala Gly Cys Gln Ala Pro Ser Asp His Pro Ile
1               5                   10                  15

Leu Cys Val Asn Asn Cys Gly Phe Phe Gly Ser Ala Ala Thr Met Asn
            20                  25                  30

Met Cys Ser Lys Cys His Lys Asp Thr Met Leu Asn Gln Glu Gln Ser
        35                  40                  45

Lys Leu Ala Ala Ser Ser Ala Ala Ser Ile Leu Asn Gly Ser Ser Met
    50                  55                  60
```

```
Ser Leu Gly Arg Glu Leu Val Ile Ala Ala Lys Thr Asn Ser Val Glu
 65                  70                  75                  80

Pro Lys Thr Ile Ser Val Gln Pro Ser Ser Ala Ser Ala Glu Glu
                 85                  90                  95

Ser Ile Glu Met Lys Leu Pro Lys Glu Gly Pro Ser Arg Cys Asn Thr
            100                 105                 110

Cys Asn Lys Arg Val Gly Leu Thr Gly Phe Lys Cys Arg Cys Glu Asn
        115                 120                 125

Met Phe Cys Ala Asn His Arg Tyr Ser Asp Lys His Asn Cys Pro Phe
    130                 135                 140

Asp Tyr Arg Thr Ala Gly Arg Glu Ala Ile Ser Lys Ala Asn Pro Leu
145                 150                 155                 160

Val Lys Ala Glu Lys Leu Asp Lys Ile
                165
```

<210> SEQ ID NO 29
<211> LENGTH: 495
<212> TYPE: DNA
<213> ORGANISM: Oryza sativa
<220> FEATURE:
<221> NAME/KEY: CDS
<222> LOCATION: (1)..(495)
<223> OTHER INFORMATION: zinc finger protein containing an A20 domain
      and an AN1 domain (OS39781852)

<400> SEQUENCE: 29

```
atg gcg cag cgc gac aag aag gat cag gag ccg acg gag ctc agg gcg      48
Met Ala Gln Arg Asp Lys Lys Asp Gln Glu Pro Thr Glu Leu Arg Ala
 1               5                  10                  15 ccg gag atc acg ctg tgc gcc aac agc tgc gga ttc ccg ggc aac ccg      96
Pro Glu Ile Thr Leu Cys Ala Asn Ser Cys Gly Phe Pro Gly Asn Pro
             20                  25                  30 gcc acg cag aac ctc tgc cag aac tgc ttc ttg gcg gcc acg gcg tcc     144
Ala Thr Gln Asn Leu Cys Gln Asn Cys Phe Leu Ala Ala Thr Ala Ser
         35                  40                  45 acc tcg tcg ccg tct tct ttg tcg tca ccg gtg ctc gac aag cag ccg     192
Thr Ser Ser Pro Ser Ser Leu Ser Ser Pro Val Leu Asp Lys Gln Pro
     50                  55                  60 ccg agg ccg gcg gcg ccg ctg gtt gag cct cag gct cct ctc cca ccg     240
Pro Arg Pro Ala Ala Pro Leu Val Glu Pro Gln Ala Pro Leu Pro Pro
 65                  70                  75                  80 cct gtg gag gag atg gcc tcc gcg ctc gcg acg gcg ccg gcg ccg gtc     288
Pro Val Glu Glu Met Ala Ser Ala Leu Ala Thr Ala Pro Ala Pro Val
                 85                  90                  95 gcc aag acg tcg gcg gtg aac cgg tgc tcc agg tgc cgg aag cgt gtc     336
Ala Lys Thr Ser Ala Val Asn Arg Cys Ser Arg Cys Arg Lys Arg Val
            100                 105                 110 ggc ctc acc ggg ttc cgg tgc cgg tgc ggc cac ctg ttc tgc ggc gag     384
Gly Leu Thr Gly Phe Arg Cys Arg Cys Gly His Leu Phe Cys Gly Glu
        115                 120                 125 cac cgg tac tcc gac cgc cac ggc tgc agc tac gac tac aag tcg gcg     432
His Arg Tyr Ser Asp Arg His Gly Cys Ser Tyr Asp Tyr Lys Ser Ala
    130                 135                 140 gcg agg gac gcc atc gcc agg gac aac ccg gtg gtg cgc gcg gcc aag     480
Ala Arg Asp Ala Ile Ala Arg Asp Asn Pro Val Val Arg Ala Ala Lys
145                 150                 155                 160 atc gtt agg ttc tga                                                  495
Ile Val Arg Phe
```

<210> SEQ ID NO 30

-continued

```
<211> LENGTH: 164
<212> TYPE: PRT
<213> ORGANISM: Oryza sativa

<400> SEQUENCE: 30

Met Ala Gln Arg Asp Lys Lys Asp Gln Glu Pro Thr Glu Leu Arg Ala
1               5                   10                  15

Pro Glu Ile Thr Leu Cys Ala Asn Ser Cys Gly Phe Pro Gly Asn Pro
            20                  25                  30

Ala Thr Gln Asn Leu Cys Gln Asn Cys Phe Leu Ala Ala Thr Ala Ser
        35                  40                  45

Thr Ser Ser Pro Ser Ser Leu Ser Pro Val Leu Asp Lys Gln Pro
    50                  55                  60

Pro Arg Pro Ala Ala Pro Leu Val Glu Pro Gln Ala Pro Leu Pro Pro
65                  70                  75                  80

Pro Val Glu Glu Met Ala Ser Ala Leu Ala Thr Ala Pro Ala Pro Val
                85                  90                  95

Ala Lys Thr Ser Ala Val Asn Arg Cys Ser Arg Cys Arg Lys Arg Val
            100                 105                 110

Gly Leu Thr Gly Phe Arg Cys Arg Cys Gly His Leu Phe Cys Gly Glu
        115                 120                 125

His Arg Tyr Ser Asp Arg His Gly Cys Ser Tyr Asp Tyr Lys Ser Ala
    130                 135                 140

Ala Arg Asp Ala Ile Ala Arg Asp Asn Pro Val Val Arg Ala Ala Lys
145                 150                 155                 160

Ile Val Arg Phe

<210> SEQ ID NO 31
<211> LENGTH: 495
<212> TYPE: DNA
<213> ORGANISM: Oryza sativa
<220> FEATURE:
<221> NAME/KEY: CDS
<222> LOCATION: (1)..(495)
<223> OTHER INFORMATION: zinc finger protein containing an A20 domain
      and an AN1 domain (OS34701560)

<400> SEQUENCE: 31 atg gcc gaa gaa cac cga tgc caa gct ccc gaa ggt cac aga ctc tgc        48
Met Ala Glu Glu His Arg Cys Gln Ala Pro Glu Gly His Arg Leu Cys
1               5                   10                  15 tcc aac aac tgc ggt ttc ttt ggt agc ccc gcc acc atg aat ctc tgt        96
Ser Asn Asn Cys Gly Phe Phe Gly Ser Pro Ala Thr Met Asn Leu Cys
            20                  25                  30 tcc aaa tgc tac aga gac atc cgt ttg aag gaa gaa gaa caa gcc aaa       144
Ser Lys Cys Tyr Arg Asp Ile Arg Leu Lys Glu Glu Glu Gln Ala Lys
        35                  40                  45 acc aaa tcc aca atc gaa acc gct ctt tca gga tct tcc tcc gcc acc       192
Thr Lys Ser Thr Ile Glu Thr Ala Leu Ser Gly Ser Ser Ser Ala Thr
    50                  55                  60 gtc acc gca acc gcc gtc gtt gcc tcc tcc gtg gaa tcc cct tcg gcg       240
Val Thr Ala Thr Ala Val Val Ala Ser Ser Val Glu Ser Pro Ser Ala
65                  70                  75                  80 ccg gtt gaa tcc ctc cct caa cca ccg gtg ctg att tcg ccg gat ata       288
Pro Val Glu Ser Leu Pro Gln Pro Pro Val Leu Ile Ser Pro Asp Ile
                85                  90                  95 gcc gca ccg gtt cag gcg aac cgg tgc ggc gcg tgt agg aag cgc gtg       336
Ala Ala Pro Val Gln Ala Asn Arg Cys Gly Ala Cys Arg Lys Arg Val
            100                 105                 110 ggg ttg aca ggg ttc aag tgc agg tgc gga aca acg ttt tgt ggg agc       384
Gly Leu Thr Gly Phe Lys Cys Arg Cys Gly Thr Thr Phe Cys Gly Ser
```

```
Gly Leu Thr Gly Phe Lys Cys Arg Cys Gly Thr Thr Phe Cys Gly Ser
        115                 120                 125 cac agg tac ccc gag aaa cac gcg tgt ggc ttc gat ttc aag gcg gtg        432
His Arg Tyr Pro Glu Lys His Ala Cys Gly Phe Asp Phe Lys Ala Val
        130                 135                 140 ggg aga gag gag ata gca cgg gcg aat ccc gtg atc aaa ggc gag aag        480
Gly Arg Glu Glu Ile Ala Arg Ala Asn Pro Val Ile Lys Gly Glu Lys
145                 150                 155                 160 cta cgg agg att taa                                                    495
Leu Arg Arg Ile <210> SEQ ID NO 32
<211> LENGTH: 164
<212> TYPE: PRT
<213> ORGANISM: Oryza sativa

<400> SEQUENCE: 32

Met Ala Glu Glu His Arg Cys Gln Ala Pro Glu Gly His Arg Leu Cys
1               5                   10                  15

Ser Asn Asn Cys Gly Phe Phe Gly Ser Pro Ala Thr Met Asn Leu Cys
                20                  25                  30

Ser Lys Cys Tyr Arg Asp Ile Arg Leu Lys Glu Glu Gln Ala Lys
        35                  40                  45

Thr Lys Ser Thr Ile Glu Thr Ala Leu Ser Gly Ser Ser Ala Thr
    50                  55                  60

Val Thr Ala Thr Ala Val Val Ala Ser Val Glu Ser Pro Ser Ala
65                  70                  75                  80

Pro Val Glu Ser Leu Pro Gln Pro Pro Val Leu Ile Ser Pro Asp Ile
                85                  90                  95

Ala Ala Pro Val Gln Ala Asn Arg Cys Gly Ala Cys Arg Lys Arg Val
            100                 105                 110

Gly Leu Thr Gly Phe Lys Cys Arg Cys Gly Thr Thr Phe Cys Gly Ser
        115                 120                 125

His Arg Tyr Pro Glu Lys His Ala Cys Gly Phe Asp Phe Lys Ala Val
        130                 135                 140

Gly Arg Glu Glu Ile Ala Arg Ala Asn Pro Val Ile Lys Gly Glu Lys
145                 150                 155                 160

Leu Arg Arg Ile

<210> SEQ ID NO 33
<211> LENGTH: 513
<212> TYPE: DNA
<213> ORGANISM: Oryza sativa
<220> FEATURE:
<221> NAME/KEY: CDS
<222> LOCATION: (1)..(513)
<223> OTHER INFORMATION: zinc finger protein containing an A20 domain
      and an AN1 domain (OS36821256)

<400> SEQUENCE: 33 atg gcg cag agg gag aag aag gtg gag gag ccg acg gag ctg agg gcg        48
Met Ala Gln Arg Glu Lys Lys Val Glu Glu Pro Thr Glu Leu Arg Ala
1               5                   10                  15 ccg gag atg acg ctc tgc gcc aac agc tgc ggg ttc ccg ggc aac ccg        96
Pro Glu Met Thr Leu Cys Ala Asn Ser Cys Gly Phe Pro Gly Asn Pro
                20                  25                  30 gcg acc aac aac ctc tgc cag aac tgc ttc ttg gct gcc tcg gcg tct        144
Ala Thr Asn Asn Leu Cys Gln Asn Cys Phe Leu Ala Ala Ser Ala Ser
        35                  40                  45 tct tct tct tct tcc gcc gct gcc tcg ccg tcg acg acg tcg ttg ccg        192
```

| | | | | | | | | | | | | | | | |
|---|---|---|---|---|---|---|---|---|---|---|---|---|---|---|---|
| Ser | Ser | Ser | Ser | Ser | Ala | Ala | Ala | Ser | Pro | Ser | Thr | Thr | Ser | Leu | Pro |
| | 50 | | | | | 55 | | | | | 60 | | | | |

```
gtg ttt ccg gtg gtg gag aag ccg agg cag gcc gta cag tcg tcg gcg      240
Val Phe Pro Val Val Glu Lys Pro Arg Gln Ala Val Gln Ser Ser Ala
 65              70                  75                  80 gcg gcg gcg gtg gcg ctg gtg gtt gag cgg ccg acg gcg ggg ccg gtg      288
Ala Ala Ala Val Ala Leu Val Val Glu Arg Pro Thr Ala Gly Pro Val
                 85                  90                  95 gag tcg tcg tcg aag gcg tcg agg tcg tcg gtc aac cga tgc cac          336
Glu Ser Ser Ser Lys Ala Ser Arg Ser Ser Val Asn Arg Cys His
            100                 105                 110 agc tgc cgg agg cgg gtg ggc ctg acc ggg ttc cgg tgc cgc tgc ggc      384
Ser Cys Arg Arg Arg Val Gly Leu Thr Gly Phe Arg Cys Arg Cys Gly
            115                 120                 125 gag ctc tac tgc ggc gcg cac cgg tac tcc gac cgc cac gac tgc agc      432
Glu Leu Tyr Cys Gly Ala His Arg Tyr Ser Asp Arg His Asp Cys Ser
130                 135                 140 ttc gac tac aag tcg gcg gcg agg gac gcc atc gcc agg gag aac ccc      480
Phe Asp Tyr Lys Ser Ala Ala Arg Asp Ala Ile Ala Arg Glu Asn Pro
145                 150                 155                 160 gtc gtc cgc gcc gcc aag atc gtt agg ttc taa                          513
Val Val Arg Ala Ala Lys Ile Val Arg Phe
                165                 170

<210> SEQ ID NO 34
<211> LENGTH: 170
<212> TYPE: PRT
<213> ORGANISM: Oryza sativa

<400> SEQUENCE: 34

Met Ala Gln Arg Glu Lys Lys Val Glu Glu Pro Thr Glu Leu Arg Ala
  1               5                  10                  15

Pro Glu Met Thr Leu Cys Ala Asn Ser Cys Gly Phe Pro Gly Asn Pro
                 20                  25                  30

Ala Thr Asn Asn Leu Cys Gln Asn Cys Phe Leu Ala Ala Ser Ala Ser
             35                  40                  45

Ser Ser Ser Ser Ser Ala Ala Ala Ser Pro Ser Thr Thr Ser Leu Pro
     50                  55                  60

Val Phe Pro Val Val Glu Lys Pro Arg Gln Ala Val Gln Ser Ser Ala
 65                  70                  75                  80

Ala Ala Ala Val Ala Leu Val Val Glu Arg Pro Thr Ala Gly Pro Val
                 85                  90                  95

Glu Ser Ser Ser Lys Ala Ser Arg Ser Ser Val Asn Arg Cys His
            100                 105                 110

Ser Cys Arg Arg Arg Val Gly Leu Thr Gly Phe Arg Cys Arg Cys Gly
            115                 120                 125

Glu Leu Tyr Cys Gly Ala His Arg Tyr Ser Asp Arg His Asp Cys Ser
130                 135                 140

Phe Asp Tyr Lys Ser Ala Ala Arg Asp Ala Ile Ala Arg Glu Asn Pro
145                 150                 155                 160

Val Val Arg Ala Ala Lys Ile Val Arg Phe
                165                 170

<210> SEQ ID NO 35
<211> LENGTH: 486
<212> TYPE: DNA
<213> ORGANISM: Glycine max
<220> FEATURE:
<221> NAME/KEY: CDS
<222> LOCATION: (1)..(486)
```

<223> OTHER INFORMATION: zinc finger protein containing an A20 domain
       and an AN1 domain (GM51659494)

<400> SEQUENCE: 35

```
atg gct cag aaa acc gag aaa gaa gaa acc gac ttc aaa gtt ccg gaa        48
Met Ala Gln Lys Thr Glu Lys Glu Glu Thr Asp Phe Lys Val Pro Glu
1               5                   10                  15 acg att acg ctt tgc gtc aac aac tgc ggc gtc acc gga aac cct gcc        96
Thr Ile Thr Leu Cys Val Asn Asn Cys Gly Val Thr Gly Asn Pro Ala
            20                  25                  30 acg aat aac atg tgc cag aag tgc ttc act gcc tct acc gcc acc act       144
Thr Asn Asn Met Cys Gln Lys Cys Phe Thr Ala Ser Thr Ala Thr Thr
        35                  40                  45 tcc ggc gcc gga ggt gcc gga ata gct tct ccg gcg acc aga tcc ggc       192
Ser Gly Ala Gly Gly Ala Gly Ile Ala Ser Pro Ala Thr Arg Ser Gly
50                  55                  60 gtc tcc gcg cgt cct cag aag aga tct ttt cct gaa gag ccc tcg ccg       240
Val Ser Ala Arg Pro Gln Lys Arg Ser Phe Pro Glu Glu Pro Ser Pro
65                  70                  75                  80 gtg gcg gat cct cct tct tcg gac cag acg acg ccg tcg gag gcg aag       288
Val Ala Asp Pro Pro Ser Ser Asp Gln Thr Thr Pro Ser Glu Ala Lys
                85                  90                  95 cgc gtg gtc aac cgc tgc tcc gga tgc cgg cgg aag gtc gga ctc acc       336
Arg Val Val Asn Arg Cys Ser Gly Cys Arg Arg Lys Val Gly Leu Thr
            100                 105                 110 gga ttc cgg tgc cgg tgc ggc gag ctc ttc tgc gcc gag cac cgg tac       384
Gly Phe Arg Cys Arg Cys Gly Glu Leu Phe Cys Ala Glu His Arg Tyr
        115                 120                 125 tcc gac cgc cac gac tgc agc tat gac tac aaa gcc gcc gga aga gaa       432
Ser Asp Arg His Asp Cys Ser Tyr Asp Tyr Lys Ala Ala Gly Arg Glu
130                 135                 140 gcc atc gcg agg gag aat ccg gtg atc aga gct gcg aag atc gtc aaa       480
Ala Ile Ala Arg Glu Asn Pro Val Ile Arg Ala Ala Lys Ile Val Lys
145                 150                 155                 160 gtc tga                                                                486
Val
```

<210> SEQ ID NO 36
<211> LENGTH: 161
<212> TYPE: PRT
<213> ORGANISM: Glycine max

<400> SEQUENCE: 36

```
Met Ala Gln Lys Thr Glu Lys Glu Glu Thr Asp Phe Lys Val Pro Glu
1               5                   10                  15

Thr Ile Thr Leu Cys Val Asn Asn Cys Gly Val Thr Gly Asn Pro Ala
            20                  25                  30

Thr Asn Asn Met Cys Gln Lys Cys Phe Thr Ala Ser Thr Ala Thr Thr
        35                  40                  45

Ser Gly Ala Gly Gly Ala Gly Ile Ala Ser Pro Ala Thr Arg Ser Gly
50                  55                  60

Val Ser Ala Arg Pro Gln Lys Arg Ser Phe Pro Glu Glu Pro Ser Pro
65                  70                  75                  80

Val Ala Asp Pro Pro Ser Ser Asp Gln Thr Thr Pro Ser Glu Ala Lys
                85                  90                  95

Arg Val Val Asn Arg Cys Ser Gly Cys Arg Arg Lys Val Gly Leu Thr
            100                 105                 110

Gly Phe Arg Cys Arg Cys Gly Glu Leu Phe Cys Ala Glu His Arg Tyr
        115                 120                 125
```

```
Ser Asp Arg His Asp Cys Ser Tyr Asp Tyr Lys Ala Ala Gly Arg Glu
        130                 135                 140

Ala Ile Ala Arg Glu Asn Pro Val Ile Arg Ala Ala Lys Ile Val Lys
145                 150                 155                 160

Val

<210> SEQ ID NO 37
<211> LENGTH: 519
<212> TYPE: DNA
<213> ORGANISM: Glycine max
<220> FEATURE:
<221> NAME/KEY: CDS
<222> LOCATION: (1)..(519)
<223> OTHER INFORMATION: zinc finger protein containing an A20 domain
      and an AN1 domain (GM49780101)

<400> SEQUENCE: 37 atg gag cct cat gat gag act gga tgc cag gct cct gaa cgc ccc att      48
Met Glu Pro His Asp Glu Thr Gly Cys Gln Ala Pro Glu Arg Pro Ile
1               5                   10                  15 ctt tgc att aat aat tgt ggc ttc ttt gga aga gca gct acc atg aac      96
Leu Cys Ile Asn Asn Cys Gly Phe Phe Gly Arg Ala Ala Thr Met Asn
            20                  25                  30 atg tgt tcc aag tgt tac aag gac atg ctg ttg aag cag gag cag gac     144
Met Cys Ser Lys Cys Tyr Lys Asp Met Leu Leu Lys Gln Glu Gln Asp
        35                  40                  45 aaa ttt gca gca tca tcc gtt gaa aac att gtg aat ggc agt tcc aat     192
Lys Phe Ala Ala Ser Ser Val Glu Asn Ile Val Asn Gly Ser Ser Asn
    50                  55                  60 ggc aat gga aag cag gct gtg gct act ggt gct gtt gct gta caa gtt     240
Gly Asn Gly Lys Gln Ala Val Ala Thr Gly Ala Val Ala Val Gln Val
65                  70                  75                  80 gaa gct gtg gag gtc aag att gtc tgt gct cag agt tct gtg gat tcg     288
Glu Ala Val Glu Val Lys Ile Val Cys Ala Gln Ser Ser Val Asp Ser
                85                  90                  95 tcc tcc ggt gat agt ttg gag atg aaa gcc aag act ggt ccc agt aga     336
Ser Ser Gly Asp Ser Leu Glu Met Lys Ala Lys Thr Gly Pro Ser Arg
            100                 105                 110 tgt gct aca tgc cgg aaa cgt gtt ggt tta act ggt ttc agc tgc aaa     384
Cys Ala Thr Cys Arg Lys Arg Val Gly Leu Thr Gly Phe Ser Cys Lys
        115                 120                 125 tgt ggc aac ctc ttc tgt gca atg cat cgc tat tct gat aaa cat gat     432
Cys Gly Asn Leu Phe Cys Ala Met His Arg Tyr Ser Asp Lys His Asp
    130                 135                 140 tgc cct ttt gat tat agg act gtt ggt cag gat gcc ata gct aaa gcc     480
Cys Pro Phe Asp Tyr Arg Thr Val Gly Gln Asp Ala Ile Ala Lys Ala
145                 150                 155                 160 aac ccc ata att aag gca gat aag ctc gac aaa atc tag                  519
Asn Pro Ile Ile Lys Ala Asp Lys Leu Asp Lys Ile
                165                 170

<210> SEQ ID NO 38
<211> LENGTH: 172
<212> TYPE: PRT
<213> ORGANISM: Glycine max

<400> SEQUENCE: 38

Met Glu Pro His Asp Glu Thr Gly Cys Gln Ala Pro Glu Arg Pro Ile
1               5                   10                  15

Leu Cys Ile Asn Asn Cys Gly Phe Phe Gly Arg Ala Ala Thr Met Asn
            20                  25                  30

Met Cys Ser Lys Cys Tyr Lys Asp Met Leu Leu Lys Gln Glu Gln Asp
```

```
                    35                  40                  45
Lys Phe Ala Ala Ser Ser Val Glu Asn Ile Val Asn Gly Ser Ser Asn
                50                  55                  60

Gly Asn Gly Lys Gln Ala Val Ala Thr Gly Ala Val Ala Val Gln Val
 65                  70                  75                  80

Glu Ala Val Glu Val Lys Ile Val Cys Ala Gln Ser Ser Val Asp Ser
                    85                  90                  95

Ser Ser Gly Asp Ser Leu Glu Met Lys Ala Lys Thr Gly Pro Ser Arg
                100                 105                 110

Cys Ala Thr Cys Arg Lys Arg Val Gly Leu Thr Gly Phe Ser Cys Lys
                115                 120                 125

Cys Gly Asn Leu Phe Cys Ala Met His Arg Tyr Ser Asp Lys His Asp
                130                 135                 140

Cys Pro Phe Asp Tyr Arg Thr Val Gly Gln Asp Ala Ile Ala Lys Ala
145                 150                 155                 160

Asn Pro Ile Ile Lys Ala Asp Lys Leu Asp Lys Ile
                165                 170
```

<210> SEQ ID NO 39
<211> LENGTH: 525
<212> TYPE: DNA
<213> ORGANISM: Glycine max
<220> FEATURE:
<221> NAME/KEY: CDS
<222> LOCATION: (1)..(525)
<223> OTHER INFORMATION: zinc finger protein containing an A20 domain
      and an AN1 domain (GM59637305)

<400> SEQUENCE: 39

```
atg gac cat gac aag act ggg tgc caa gct cct cct gaa ggt cct ata    48
Met Asp His Asp Lys Thr Gly Cys Gln Ala Pro Pro Glu Gly Pro Ile
1               5                  10                  15 ttg tgc atc aac aac tgt ggg ttt ttt gga agt gca gct acc atg aac    96
Leu Cys Ile Asn Asn Cys Gly Phe Phe Gly Ser Ala Ala Thr Met Asn
            20                  25                  30 atg tgt tct aaa tgc cac aaa gac ata ttg ctg aaa cag gag cag gcc   144
Met Cys Ser Lys Cys His Lys Asp Ile Leu Leu Lys Gln Glu Gln Ala
        35                  40                  45 aag ctt gca gca tca tcc att ggg aat att atg aat ggg tca tca agc   192
Lys Leu Ala Ala Ser Ser Ile Gly Asn Ile Met Asn Gly Ser Ser Ser
    50                  55                  60 agc act gaa aag gaa cct gtt gtt gct gct gct gct aat att gat atc   240
Ser Thr Glu Lys Glu Pro Val Val Ala Ala Ala Ala Asn Ile Asp Ile
 65                  70                  75                  80 cca gtt att cca gta gag cct aaa act gtc tct gtg caa cct tta ttt   288
Pro Val Ile Pro Val Glu Pro Lys Thr Val Ser Val Gln Pro Leu Phe
                    85                  90                  95 ggt tca ggt cca gag ggg agt gtt gag gca aag ccg aag gat gga cca   336
Gly Ser Gly Pro Glu Gly Ser Val Glu Ala Lys Pro Lys Asp Gly Pro
                100                 105                 110 aaa cgt tgc agc agc tgc aac aag cga gtt ggt ttg aca ggg ttt aat   384
Lys Arg Cys Ser Ser Cys Asn Lys Arg Val Gly Leu Thr Gly Phe Asn
                115                 120                 125 tgt cga tgt ggt gac ctt ttt ttg tgc tgt aca tcg cta ctc gac aag   432
Cys Arg Cys Gly Asp Leu Phe Leu Cys Cys Thr Ser Leu Leu Asp Lys
                130                 135                 140 cat aat tgc cca ttt gat tac cgc act gcc gct caa gat gct ata gct   480
His Asn Cys Pro Phe Asp Tyr Arg Thr Ala Ala Gln Asp Ala Ile Ala
145                 150                 155                 160 aaa gca aac cca gtt gtc aag gct gaa aag ctt gat aag atc taa       525
Lys Ala Asn Pro Val Val Lys Ala Glu Lys Leu Asp Lys Ile
                165                 170
```

```
Lys Ala Asn Pro Val Val Lys Ala Glu Lys Leu Asp Lys Ile
            165                 170
```

<210> SEQ ID NO 40
<211> LENGTH: 174
<212> TYPE: PRT
<213> ORGANISM: Glycine max

<400> SEQUENCE: 40

```
Met Asp His Asp Lys Thr Gly Cys Gln Ala Pro Pro Glu Gly Pro Ile
1               5                   10                  15

Leu Cys Ile Asn Asn Cys Gly Phe Phe Gly Ser Ala Ala Thr Met Asn
            20                  25                  30

Met Cys Ser Lys Cys His Lys Asp Ile Leu Leu Lys Gln Glu Gln Ala
        35                  40                  45

Lys Leu Ala Ala Ser Ser Ile Gly Asn Ile Met Asn Gly Ser Ser Ser
    50                  55                  60

Ser Thr Glu Lys Glu Pro Val Val Ala Ala Ala Asn Ile Asp Ile
65                  70                  75                  80

Pro Val Ile Pro Val Glu Pro Lys Thr Val Ser Val Gln Pro Leu Phe
                85                  90                  95

Gly Ser Gly Pro Glu Gly Ser Val Glu Ala Lys Pro Lys Asp Gly Pro
            100                 105                 110

Lys Arg Cys Ser Ser Cys Asn Lys Arg Val Gly Leu Thr Gly Phe Asn
        115                 120                 125

Cys Arg Cys Gly Asp Leu Phe Leu Cys Cys Thr Ser Leu Leu Asp Lys
    130                 135                 140

His Asn Cys Pro Phe Asp Tyr Arg Thr Ala Ala Gln Asp Ala Ile Ala
145                 150                 155                 160

Lys Ala Asn Pro Val Val Lys Ala Glu Lys Leu Asp Lys Ile
            165                 170
```

<210> SEQ ID NO 41
<211> LENGTH: 498
<212> TYPE: DNA
<213> ORGANISM: Triticum aestivum
<220> FEATURE:
<221> NAME/KEY: CDS
<222> LOCATION: (1)..(498)
<223> OTHER INFORMATION: zinc finger protein containing an A20 domain
      and an AN1 domain (TA55974113)

<400> SEQUENCE: 41

```
atg gcg cag cgg gat cac aag cag gag gag ccc acg gag ctg cgg gcg      48
Met Ala Gln Arg Asp His Lys Gln Glu Glu Pro Thr Glu Leu Arg Ala
1               5                   10                  15 ccg gag atc acg ctc tgc gcc aac agc tgc ggc ttc ccg ggc aac ccg      96
Pro Glu Ile Thr Leu Cys Ala Asn Ser Cys Gly Phe Pro Gly Asn Pro
            20                  25                  30 gcc acg cag aac ctc tgc cag aac tgc ttc ttg gcc ggc ccg gcg tcc     144
Ala Thr Gln Asn Leu Cys Gln Asn Cys Phe Leu Ala Gly Pro Ala Ser
        35                  40                  45 acg tcg ccg tct tcc tcc tcc tcc tcc tct tct ctg ccg ggc gtg         192
Thr Ser Pro Ser Ser Ser Ser Ser Ser Ser Ser Leu Pro Gly Val
    50                  55                  60 tcc gcg ccg acc ccc gtc atc gac agg ccg agg ccg gcg ccg ttg gag     240
Ser Ala Pro Thr Pro Val Ile Asp Arg Pro Arg Pro Ala Pro Leu Glu
65                  70                  75                  80 gcg gag ctg gca cgc ccc gcc gtc gac ctt gct ccg gcg acg gag gcg     288
Ala Glu Leu Ala Arg Pro Ala Val Asp Leu Ala Pro Ala Thr Glu Ala
                85                  90                  95
```

```
aag ccg gcg agg acg tcg gtg aac cgg tgc tcc agc tgc cgg aag cgc        336
Lys Pro Ala Arg Thr Ser Val Asn Arg Cys Ser Ser Cys Arg Lys Arg
        100                 105                 110 gtg ggg ctg acg ggg ttc cgg tgc cgg tgc ggc gac atg ttc tgc ggc        384
Val Gly Leu Thr Gly Phe Arg Cys Arg Cys Gly Asp Met Phe Cys Gly
            115                 120                 125 gag cac cgg tac tcg gac cgg cac ggg tgc agc tac gac tac aag gcc        432
Glu His Arg Tyr Ser Asp Arg His Gly Cys Ser Tyr Asp Tyr Lys Ala
130                 135                 140 gcc gcc agg gac gcc atc gcc agg gac aac ccc gtc gtg cgc gcc gcc        480
Ala Ala Arg Asp Ala Ile Ala Arg Asp Asn Pro Val Val Arg Ala Ala
145                 150                 155                 160 aag atc gtc agg ttc tga                                                 498
Lys Ile Val Arg Phe
            165

<210> SEQ ID NO 42
<211> LENGTH: 165
<212> TYPE: PRT
<213> ORGANISM: Triticum aestivum

<400> SEQUENCE: 42

Met Ala Gln Arg Asp His Lys Gln Glu Glu Pro Thr Glu Leu Arg Ala
1               5                   10                  15

Pro Glu Ile Thr Leu Cys Ala Asn Ser Cys Gly Phe Pro Gly Asn Pro
            20                  25                  30

Ala Thr Gln Asn Leu Cys Gln Asn Cys Phe Leu Ala Gly Pro Ala Ser
        35                  40                  45

Thr Ser Pro Ser Ser Ser Ser Ser Ser Ser Leu Pro Gly Val
    50                  55                  60

Ser Ala Pro Thr Pro Val Ile Asp Arg Pro Arg Pro Ala Pro Leu Glu
65                  70                  75                  80

Ala Glu Leu Ala Arg Pro Ala Val Asp Leu Ala Pro Ala Thr Glu Ala
                85                  90                  95

Lys Pro Ala Arg Thr Ser Val Asn Arg Cys Ser Ser Cys Arg Lys Arg
            100                 105                 110

Val Gly Leu Thr Gly Phe Arg Cys Arg Cys Gly Asp Met Phe Cys Gly
        115                 120                 125

Glu His Arg Tyr Ser Asp Arg His Gly Cys Ser Tyr Asp Tyr Lys Ala
    130                 135                 140

Ala Ala Arg Asp Ala Ile Ala Arg Asp Asn Pro Val Val Arg Ala Ala
145                 150                 155                 160

Lys Ile Val Arg Phe
            165

<210> SEQ ID NO 43
<211> LENGTH: 207
<212> TYPE: PRT
<213> ORGANISM: Physcomitrella patens
<220> FEATURE:
<221> NAME/KEY: MISC_FEATURE
<222> LOCATION: (1)..(207)
<223> OTHER INFORMATION: methionine sulfoxide reductase family protein
      (EST65)

<400> SEQUENCE: 43

Met Val Ala Glu Ser Val Leu Val Cys Arg Ser Ser Val Val Gly Ala
1               5                   10                  15

Gly Leu Gln Ser Phe Val Gly Glu Gly Ala Lys Arg Glu Ser Ala Gly
            20                  25                  30
```

Pro Gly Arg Ser Val Phe Leu Gly Ala Gln Val Gln Lys Met Gly Ala
            35                  40                  45

Gly Met Ser Ala Arg Ser Asp Val Arg Pro Ala Ala Val Pro Lys Ala
 50                  55                  60

Ser Gly Asp Val Ser Glu Gln Thr Asp Tyr Lys Thr Phe Ser Asp Glu
 65                  70                  75                  80

Glu Trp Lys Lys Arg Leu Ser Gln Gln Gln Phe Tyr Val Ala Arg Lys
                 85                  90                  95

Lys Gly Thr Glu Arg Pro Phe Thr Gly Glu Tyr Trp Asn Thr Lys Thr
            100                 105                 110

Ala Gly Thr Tyr Leu Cys Val Cys Lys Thr Pro Leu Phe Ser Ser
            115                 120                 125

Lys Thr Lys Phe Asp Ser Gly Thr Gly Trp Pro Ser Tyr Tyr Asp Thr
            130                 135                 140

Ile Gly Asp Asn Val Lys Ser His Met Asp Trp Ser Ile Pro Phe Met
145                 150                 155                 160

Pro Arg Thr Glu Val Val Cys Ala Val Cys Asp Ala His Leu Gly His
                165                 170                 175

Val Phe Asp Asp Gly Pro Arg Pro Thr Gly Lys Arg Tyr Cys Ile Asn
                180                 185                 190

Ser Ala Ala Ile Asp Leu Lys Ala Glu Lys Gln Glu Glu Arg Asn
            195                 200                 205

<210> SEQ ID NO 44
<211> LENGTH: 339
<212> TYPE: PRT
<213> ORGANISM: Physcomitrella patens
<220> FEATURE:
<221> NAME/KEY: MISC_FEATURE
<222> LOCATION: (1)..(339)
<223> OTHER INFORMATION: homeodomain leucine zipper protein (EST12)

<400> SEQUENCE: 44

Met Val Val Pro Ser Leu Pro Ala Phe Gly Gly Gln Asn Ala Met Leu
 1               5                  10                  15

Arg Arg Asn Ile Asp Asn Asn Thr Asp Thr Leu Ile Ser Leu Leu Gln
             20                  25                  30

Gly Ser Cys Ser Pro Arg Val Ser Met Gln Gln Val Pro Arg Ser Ser
            35                  40                  45

Glu Ser Leu Glu Asn Met Met Gly Ala Cys Gly Gln Lys Leu Pro Tyr
 50                  55                  60

Phe Ser Ser Phe Asp Gly Pro Ser Val Glu Glu Gln Glu Asp Val Asp
 65                  70                  75                  80

Glu Gly Ile Asp Glu Phe Ala His His Val Lys Lys Arg Arg Leu
                 85                  90                  95

Ser Leu Glu Gln Val Arg Ser Leu Glu Arg Asn Phe Glu Val Glu Asn
            100                 105                 110

Lys Leu Glu Pro Glu Arg Lys Met Gln Leu Ala Lys Glu Leu Gly Leu
            115                 120                 125

Arg Pro Arg Gln Val Ala Val Trp Phe Gln Asn Arg Arg Ala Arg Trp
            130                 135                 140

Lys Thr Lys Gln Leu Glu His Asp Tyr Glu Thr Leu Lys Ala Tyr
145                 150                 155                 160

Asp Arg Leu Lys Ala Asp Phe Glu Ala Val Thr Leu Asp Thr Asn Ala
                165                 170                 175

Leu Lys Ala Glu Val Ser Arg Leu Lys Gly Ile Ser Asn Asp Asp Val

-continued

```
                180                 185                 190
Lys Pro Ala Glu Phe Val Gln Gly Lys Cys Asp Thr Thr Ser His Pro
                195                 200                 205

Ala Ser Pro Ala Gln Ser Glu Arg Ser Asp Ile Val Ser Ser Arg Asn
            210                 215                 220

Arg Thr Thr Pro Thr Ile His Val Asp Pro Val Ala Pro Glu Glu Ala
225                 230                 235                 240

Gly Ala His Leu Thr Met Ser Ser Asp Ser Asn Ser Ser Glu Val Met
                245                 250                 255

Asp Ala Asp Ser Pro Arg Thr Ser His Thr Ser Ala Ser Arg Ser Thr
            260                 265                 270

Leu Ser Thr Ser Val Val Gln Pro Asp Glu Gly Leu Gly Val Ala Gln
        275                 280                 285

Tyr Pro His Phe Ser Pro Glu Asn Phe Val Gly Pro Asn Met Pro Glu
        290                 295                 300

Ile Cys Ala Asp Gln Ser Leu Ala Ser Gln Val Lys Leu Glu Glu Ile
305                 310                 315                 320

His Ser Phe Asn Pro Asp Gln Thr Phe Leu Leu Leu Pro Asn Trp Trp
                325                 330                 335

Asp Trp Ala

<210> SEQ ID NO 45
<211> LENGTH: 188
<212> TYPE: PRT
<213> ORGANISM: Physcomitrella patens
<220> FEATURE:
<221> NAME/KEY: MISC_FEATURE
<222> LOCATION: (1)..(188)
<223> OTHER INFORMATION: zinc finger protein containing an A20 domain
      and an AN1 domain (EST307)

<400> SEQUENCE: 45

Met Ala Thr Glu Arg Val Ser Gln Glu Thr Thr Ser Gln Ala Pro Glu
1               5                   10                  15

Gly Pro Val Met Cys Lys Asn Leu Cys Gly Phe Phe Gly Ser Gln Ala
            20                  25                  30

Thr Met Gly Leu Cys Ser Lys Cys Tyr Arg Glu Thr Val Met Gln Ala
        35                  40                  45

Lys Met Thr Ala Leu Ala Glu Gln Ala Thr Gln Ala Ala Gln Ala Thr
    50                  55                  60

Ser Ala Thr Ala Ala Val Gln Pro Pro Ala Pro Val His Glu Thr
65                  70                  75                  80

Lys Leu Thr Cys Glu Val Glu Arg Thr Met Ile Val Pro His Gln Ser
                85                  90                  95

Ser Ser Tyr Gln Gln Asp Leu Val Thr Pro Ala Ala Ala Ala Pro Gln
            100                 105                 110

Ala Val Lys Ser Ser Ile Ala Ala Pro Ser Arg Pro Glu Pro Asn Arg
        115                 120                 125

Cys Gly Ser Cys Arg Lys Arg Val Gly Leu Thr Gly Phe Lys Cys Arg
130                 135                 140

Cys Gly Asn Leu Tyr Cys Ala Leu His Arg Tyr Ser Asp Lys His Thr
145                 150                 155                 160

Cys Thr Tyr Asp Tyr Lys Ala Ala Gly Gln Glu Ala Ile Ala Lys Ala
                165                 170                 175

Asn Pro Leu Val Val Ala Glu Lys Val Val Lys Phe
            180                 185
```